United States Patent [19]

Fujimoto et al.

[11] 3,996,244
[45] Dec. 7, 1976

[54] INSECTICIDAL ESTERS OF SUBSTITUTED FURAN METHANOL

[75] Inventors: Keimei Fujimoto, Kobe; Nobuo Ohno; Yoshitoshi Okuno, both of Toyonaka; Toshio Mizutani, Toyonaka; Isao Ohno, Minoo; Masachika Hirano, Toyonaka; Nobushige Itaya, Ikeda; Takashi Matsuo, Amagasaki, all of Japan

[73] Assignee: Sumitomo Chemical Company, Limited, Osaka, Japan

[22] Filed: July 11, 1973

[21] Appl. No.: 378,301

[30] Foreign Application Priority Data

July 11, 1972 Japan .............................. 47-69805
Apr. 19, 1973 Japan .............................. 48-44809

[52] U.S. Cl. ................. 260/332.2 A; 260/332.2 R; 260/340.5; 260/346.2 R; 260/347.2; 260/347.5; 424/275; 424/282; 424/285
[51] Int. Cl.² ................................. C07D 317/54
[58] Field of Search ......... 260/347.4, 347.2, 347.5, 260/340.5, 346.2 R, 332.2 A, 332.2 R

[56] References Cited
OTHER PUBLICATIONS

Groggins "Unit Processes in Organic Synthesis" 1958 pp. 715–719.
Chem. Abst. Decenial Indeces: 2nd (p. 6251), 3rd (p. 7607), 4th (p. 9408), 5th (p. 12625), 6th (p. 11669), 7th (p. 22711), 8th (p. 31129–31130) (Thiophenes).
Chem. Abst. Decenial Indeces: 1st (p. 3096–3097), 2nd (p. 4088), 3rd (p. 5036) 4th (p. 6051), 5th (p. 5394s), 6th (5039s), 7th (p. 9719s), 8th (p. 13201–13202) (Furans).
Chem. Abst. Dec. Indeces. 1st (p. 2787, 2795–2796), 2nd (p. 3652–3659), 3rd (p. 4489–4490, 4501), 4th (p. 5315, 5337), 5th (p. 3892–3948), 6th (p. 3612–3613, 3668–3669), 7th (p. 6982–6983, 7109–7110), 8th (p. 9168–9169, 9334–9335).
Chem. Abst. Dec. Indeces: 1st (p. 3311), 2nd (p. 4410), 3rd (p. 5439), 4th (p. 6539), 5th (p. 6443), 6th (p. 5952), 7th (p. 10997–10998), 8th (p. 14932).

Primary Examiner—Henry R. Jiles
Assistant Examiner—Bernard Dentz
Attorney, Agent, or Firm—Sughrue, Rothwell, Mion, Zinn & Macpeak

[57] ABSTRACT

Substituted acetate compounds represented by the formula

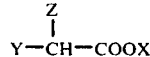

which are useful as pesticides and pesticidal composition containing the substituted acetate compounds as active ingredients, as well as processes for preparing the compounds and the compositions are disclosed.

11 Claims, No Drawings

INSECTICIDAL ESTERS OF SUBSTITUTED FURAN METHANOL

SUMMARY OF THE INVENTION

1. Field of the Invention

This invention relates to a pesticide, and more particularly, this invention relates to substituted acetate compounds of the following formula (I) useful for controlling an arthropod, pesticidal compositions containing as active ingredients at least one substituted acetate compound of the formula (I), as well as processes for preparing the substituted acetate compounds and the pesticidal compositions.

The substituted acetate compounds of this invention are represented by the formula:

wherein Y represents a substituted aromatic group or an unsaturated Alicyelle group having an appropriate plane and is selected from the group consisting of the formulae in the formula (V) represents a double bond present at a position conjugated or non-conjugated with the ketone (C=O), or Y represents a substituted ethylene group of the formula (VI)

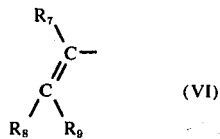

in which $R_7$, $R_8$ and $R_9$ constitutes a plane together with the double bond at $\beta$ - $\gamma$ position of the ester group, and are individually hydrogen, lower alkyl, lower alkenyl, lower alkynyl, halogen, acyl or acyloxy; Z represents a straight or branched lower alkyl, lower alkenyl, lower alkynyl, lower alkoxy, cyano, halogen-substituted lower alkyl, halogen-substituted lower alkenyl group or an Alicyclic group having 3 to 7 carbon atoms; X represents a group corresponding to an alcohol moiety of the ester-type insecticides which are known as pyrethroid insecticides, and is selected from the group consisting of the formulae

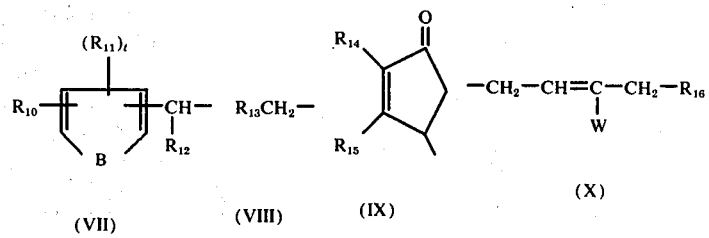

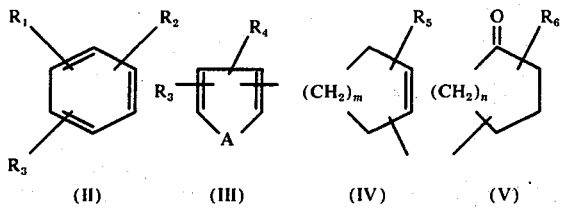

in which $R_1$ and $R_2$ ar individually hydrogen, halogen, cyano, nitro, lower alkyl, lower alkenyl, lower alkynyl, lower alkoxy, lower alkoxyalkyl, halogen-substituted lower alkyl, halogen-substituted lower alkenyl, halogen-substituted lower alkynyl, lower-alkylthio, lower alkylsulfoxyl, acyl, acyloxy, lower alkoxycarbonyl, lower alkenyloxycarbonyl, lower alkynyloxycarbonyl, methylenedioxy, tetramethylene or trimethylene group; $R_3$ and $R_4$ are individually hydrogen, halogen, cyano, nitro, lower alkyl, lower alkenyl, lower alkynyl, lower alkoxy lower alkoxyalkyl, halogen-substituted lower alkyl, halogen-substituted lower alkenyl, halogen-substituted lower alkynyl, lower alkylthio, lower alkylsulfoxyl, acyl, acyloxy, lower alkoxycarbonyl, lower alkenyloxycarbonyl or lower alkynyloxycarbonyl group; A represents an oxygen atom or a sulfur atom; $R_5$ represents hydrogen, halogen, cyano, nitro or lower alkyl group; m is an integer of from 1 to 3; $R_6$ represents hydrogen, halogen, cyano, nitro or lower alkyl group; n is an integer of from 1 to 3; and the dotted line in which $R_{10}$ represents an allyl, propargyl, benzyl, thenyl, furylmethyl, phenoxy or phenylthio group; $R_{11}$ represents hydrogen, methyl, trifluoromethyl or halogen, $R_{10}$ and $R_{11}$ may, when they are bonded to each other at terminals, form a trimethylene or tetramethylene group; $R_{12}$ represents hydrogen, ethynyl or cyano; t is an integer of from 1 to 2; B represents an oxygen or sulfur atom or a group —CH=CH—; $R_{13}$ represents phthalimide, thiophthalimide, di- or tetrahydrophthalimide or dialkylmaleimide; $R_{14}$ represents allyl, propargyl, benzyl or alkadienyl; $R_{15}$ represents hydrogen or methyl; $R_{16}$ represents phenyl, thienyl or furyl; and W represents methyl or halogen. Preferred ranges of compounds within the formula (I) are as follows:

1. compounds of the formula:

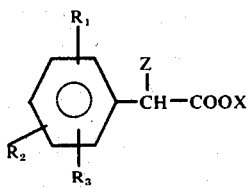

wherein $R_1$ is a member selected from the group consisting of hydrogen, methoxy, ethoxy, acetoxy, methyl-sulfinyl, $C_1$–$C_4$ alkyl, trifluoromethyl, allyl, acetyl, ethoxycarbonyl, methylenedioxy, methylthio, trimethylene, tetramethylene, chlorine, fluorine, iodine, isopropenyl, propargyl, methoxymethyl, ethoxymethyl, chloroethylene, chloroallyl, butyryl, butylthio, allyloxycarbonyl, nitro and methoxycarbonyl; $R_2$ is a member selected from the group consisting of hydrogen, methyl, methoxy, chlorine and bromine; $R_3$ is hydrogen or methyl; Z is a member selected from the group consisting of $C_1$–$C_4$ alkyl, ethoxy, allyl, bromoethyl, cyclohexyl, cyclopropylmethyl, isopropenyl, propargyl, trifluoromethyl and cyano; and X is a member selected from the group consisting of:

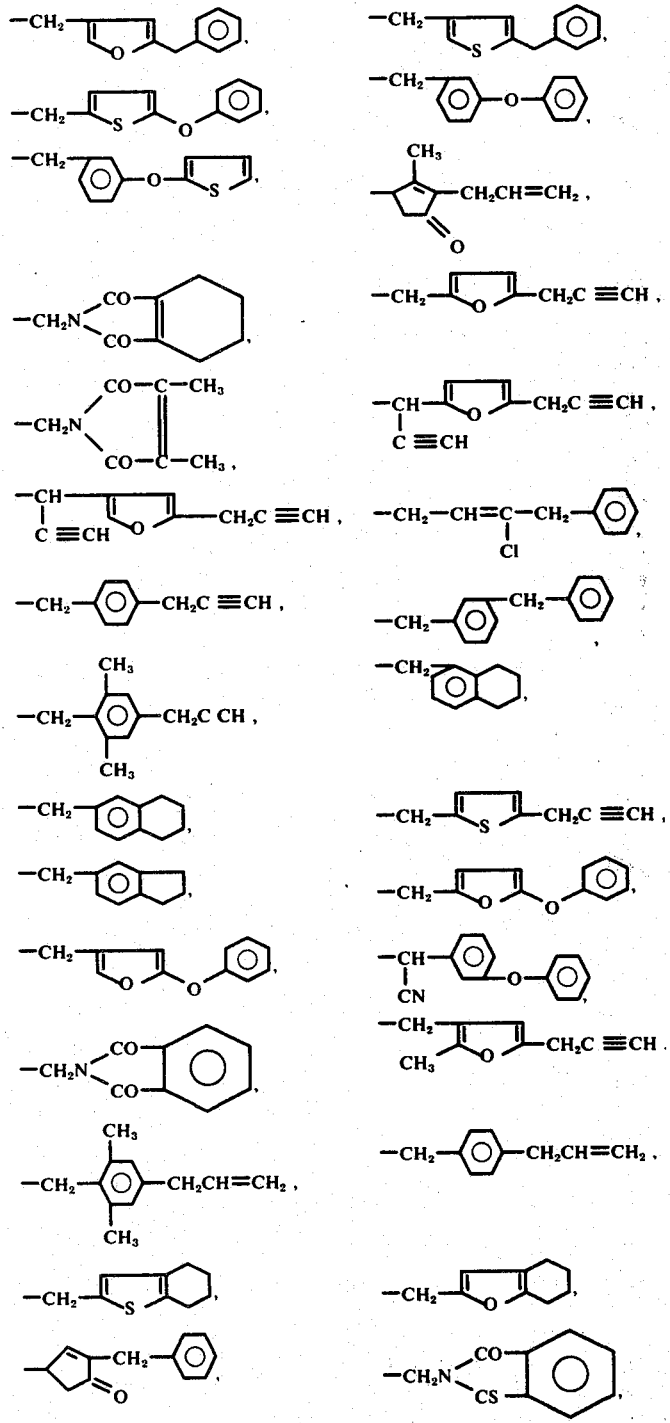

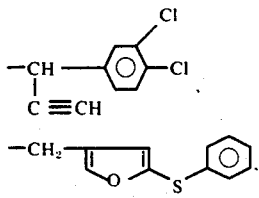
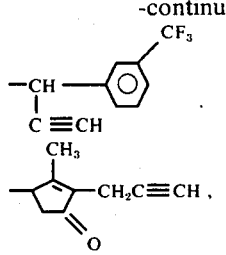

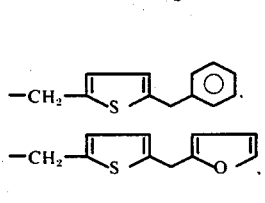
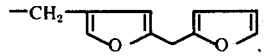
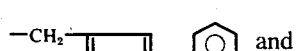

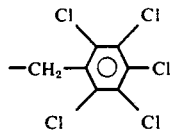
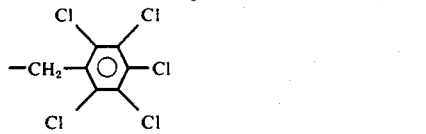

and

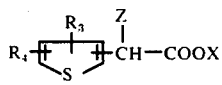

2. compounds of the formula;

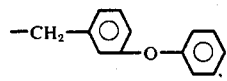 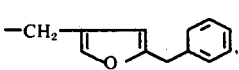

wherein $R_3$ is a member selected from the group consisting of hydrogen, methyl, allyl, methoxycarbonyl and acetyl; $R_4$ is hydrogen; Z is a member selected from the group consisting of ethyl, propyl and allyl; and X is a member selected from the group consisting of wherein $R_7$ is a member selected from the group consisting of hydrogen, methyl and ethyl; $R_8$ is hydrogen or methyl; $R_9$ is methyl; Z is $C_1-C_3$ alkyl; and X is a member selected from the group consisting of

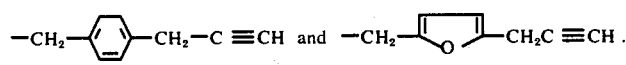

3. compounds of the formula;

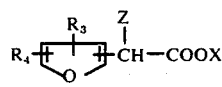

wherein $R_3$ is a member selected from the group consisting of hydrogen, methyl, allyl, methoxycarbonyl and butyryl; $R_4$ is hydrogen; Z is ethyl or propyl; X is a member selected from the group consisting of

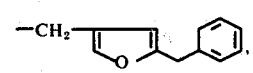 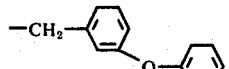

 and 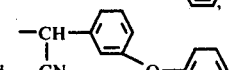

5. compounds of the formula;

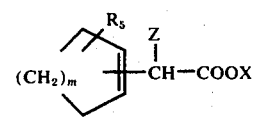

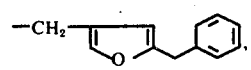 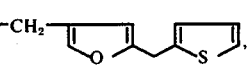

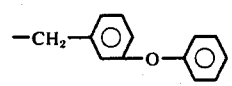 and 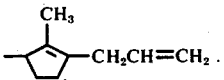

4. compounds of the formula;

wherein $R_5$ is hydrogen or methyl; m is an integar of 1 or 2; Z is a member selected from the group consisting of methyl, propyl, allyl and propargyl; X is a member selected from the group consisting of

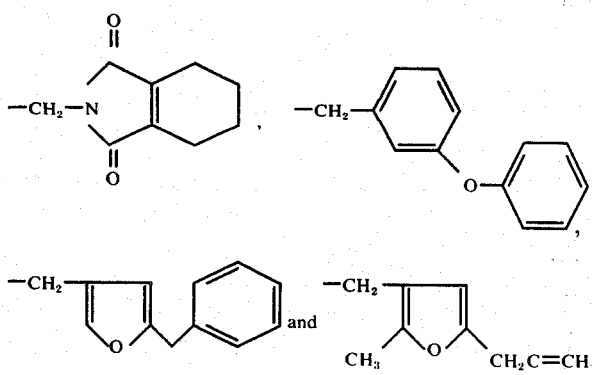

6. compounds of the formula;

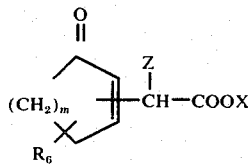

wherein $R_6$ is methyl, $n$ is an integer of 1, Z is ethyl or propyl; X is a member selected from the group consisting of

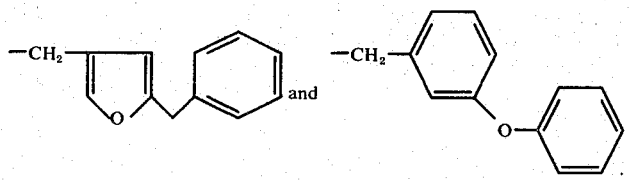

Among the present compounds, the phenylacetic acid esters prepared by reacting phenylacetic acid derivatives of the formula;

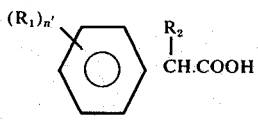

wherein $R_1$ represents a straight or branched chain alkyl group having 1 to 5 carbon atoms, a straight or branched chain alkoxy group having 1 to 5 carbon atoms, a halogen atom or a thiomethyl group and two of $R_1$ may form a trimethylene —$(CH_2)_3$— or tetramethylene —$(CH_2)_4$— or a methylenedioxy group —O—$CH_2$—O—; $n'$ is an integer of from 1 to 4; and $R_2$ represents a straight or branched alkyl group having 3 to 5 carbon atoms, allyl group, a propargyl group or isopropenyl group; with a pyrethroid alcohol have a prominent effects to injurious insects and low toxicity to mammals. And, therefore, the above mentioned phenylacetic acids are important as intermediate of the present invention.

2. Description of the Prior Art

Since BHC and DDT have been developed, remarkable advances have been made in the organic agricultural agents such as phosphorus agents, carbamates, pyrethroids and the progress of such organic agricultural agents now establishes a certain close correlation between the consumed quantity of pesticides and the harvested quantity of crops. However, on the other hand, these agricultural agents have caused pollutions by the environment contamination and at present there are many problems such as the accumulation of toxicity and the chronic toxicity as well as the generation of a wide variety of pesticide-resistant noxious insects. The desirable requirements for pesticides are, therefore, that the active pesticides exhibit a low toxicity, a low residual and a rapid decomposition and they are converted into non-toxic materials upon entrance into one of the biological cycles of the ecological system. In particular, the compounds containing no heavy metals for halogen atoms and composed mainly of carbon, hydrogen and oxygen are considered to be advantageous as agricultural agents.

The active groups of the pesticides presently used include organic phosphorus compounds, carbamates, chrysanthemic acid esters, organochloric compounds, etc., and most of the researchers in this field now endeavour to develop new types of pesticides by considering the superiority or inferiority of each of the above active groups and screening various synthetic derivatives retaining only the superiority of the known pesticides.

The present inventors considered that each of the above well-known active groups has certain properties as basic pesticidal characteristics inherent to the specific active group and that the disadvantages associated with the specific active group would not be eliminated unless departing from the above specific properties. As a result of extensive researches for active groups having novel chemical structures, the present inventors found the new and useful acetic acid esters represented by the above formula (I).

The compounds of this invention have various advantages broadly and also exhibit strong selectivity, and the chemical structures retaining only properties advantageous as agricultural agents can be considered depending upon the specific type of the compounds of this invention.

Hithertofore, esters which are considered to be pesticidal active groups, for example, phosphoric acid esters and chrysanthemic acid esters are believed to have their activities in the basic structures of phosphoric acid and cyclopropanecarboxylic acid, respectively. These esters contain a S (or O) atom bonded to a pentavalent phosphorus by a double bond as an essential structure of the phosphoric acid esters and a three-membered ring as an essential structure of the chrysanthemic acid esters, respectively, and the pesticidal activity tends to be strengthened or weakened depending upon the type of moieties present around the above essential structure as a nucleus.

In the compounds of this invention, the acid moiety represented by the formula (XI)

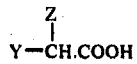
(XI)

is considered to be an important active basic structure, and its essential structure is completed by a hydrogen atom at α-position of the ester group, an appropriate substituent (Z) and a substituent (Y) which are characterized in its plane structure. On the other hand, the alcohol moiety of the ester corresponds to the alcohol moiety of the well-known chrysanthemic acid esters as shown by the examples of compounds described below,

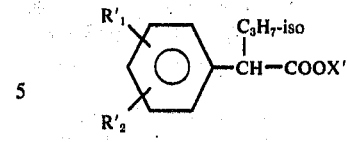
(I')

wherein $R'_1$ represents straight or branched chain alkyl having 1 to 4 carbon atoms, halogen or alkoxy having 1 to 4 carbon atoms; $R'_2$ represents hydrogen or a group which completes, together with $R'_1$, methylenedioxy; and X' represents a group of the formula,

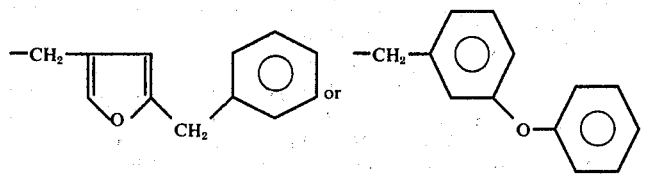

but, in accordance with the present invention, it was found that highly active pesticides can be prepared by esterification of the acids represented by the formula (XI) with the above alcohol moiety and that the compounds having a surprisingly high selectivity can be prepared by using an appropriate combination of an acid moiety and an alcohol moiety. However, the order of activity of the ester composed of the known alcohol and the known acid cannot be applied as it is to the evaluation of the activity of the esters in accordance with the present invention since the esters of this invention exhibit activities entirely different those of the known esters. Accordingly, the esters composed of the acid used in the present invention and the alcohol which has been found to form a highly active ester in the known pesticides do not necessarily exhibit an excellent activity.

In addition, in accordance with the present invention, various advantages such as immediate onset of action, permeability, transfer into living plants, residual activity, pesticidal activity, metamorphosis disturbance, sterilization, prohibition of egg-lying can freely be controlled by appropriately selecting a combination of an acid of the present invention and a wide variety of alcohols. Also, with respect to the spectrum of pesticidal activity, the compounds of this invention exhibit a selective or non-selective activity on such order as Coreoptera, Lepidoptera, Diptera, Orthoptera, Hemiptera, Homoptera and Acarus depending upon a specific combination of acid and an alcohol according to the present invention. Further, the compounds of this invention are expected to be useful for controlling noxious insects such as a nematoda. Other important features of the compounds of this invention are that they are active against noxious insects which are resistant to the pesticides presently used because of their basic structures different from these of the known pesticides to which the insects are resistant, and that they are totally low toxic to mammals including man as indicated by Experiments shown below.

As the results of the present invention, the substituted acetate compounds of the formula, are more excellent in insecticidal effect, a killing effect and a knock down effect than the other substituted acetate compounds of the formula (I).

In order to make the above fact clearer, the superiority of the compounds represented by the formula (I') in biological effects is shown below with reference to Experimental Examples. But the other compounds of the formula (I) and their geometrical isomers and optical isomers display more excellent effects as well than the known insecticidal agents.

In preparing the substituted acetic acid esters represented by the formula (I), an acid represented by the formula

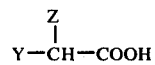
(XI)

wherein Y and Z are as defined above, or a reactive derivative thereof is reacted with an alcohol represented by the formula

 — OH     (XII)

wherein X is as defined above, or a halide or sulfoxylate thereof.

The term "reactive derivative" of the acid used herein refers to an acid halide, an acid anhydride, an ester with an alcohol having a low boiling point, and an alkali metal salt, a silver slat or an organic tertiary base salt of the acid.

The substituted acetic acid esters represented by the formula (I) include optical isomers due to the carbon atom at α-position, and it is to be understood that the present invention is contemplated to include such optical isomers.

In carrying out the production of the substituted acetic acid esters of the formula (I), the esterification between the acid (XI) and the alcohol (XII) can advantageously be accomplished by reacting the reactants in an appropriate inert solvent at room temperature or an elevated temperature under an appropriate dehydrating condition, e.g., in the presence of cyclohexylcarbodiimide. When an acid halide is used as a reactive derivative of the acid (XI), the desired ester can be obtained in high yield by reacting the alcohol (XII) and the acid halide at room temperature using an acid acceptor, for example, an organic tertiary amine such ass pyridine, triethylamine and the like. The acid halides which can be used in the process of this invention may be any type of halides within the scope of this invention, but an acid chloride is generally preferred. The presence of an inert solvent is not essential in the esterification reaction, but it is generally preferred to use a solvent in order to assure a smooth reaction. Any solvent which is inert to the reactants and the ester product may be used and a preferred inert solvent includes benzene, toluene and petroleum benzine. When an ester of the acid (XI) and a low boiling point alcohol, e.g., methanol, ethanol and the like is used as a reactive derivate of the acid, the desired ester (I) can be obtained in high yield by heat-reacting the ester and the alcohol (XII) with heating in the presence of an appropriate organic base catalyst, preferably, an alkali metal alkoxide corresponding to the low boiling alcohol of the ester used or sodium hydride in an inert solvent such as toluene while removing a low boiling alcohol liberated during the reaction from the reaction system by a fractional distillation column.

In an alternative esterification procedure using an acid anhydride as a reactive derivative of the acid (XI), the desired ester can be obtained by reacting the acid anhydride with the alcohol (XII) at room temperature without using specific reaction aids. In this case, it is preferred to heat the reaction system and to use a solvent such as toluene, xylene and the like in order to ensure a smooth reaction, but the heating and the use of solvent are not critical in this procedure.

When a halide or sulfoxylate of the above alcohol (XII) is used, the acid (XI) is generally employed in the form of an alkali metal salt, a silver salt or an organic tertiary base salt. These salts may be formed in situ by adding simultaneously the acid (XII) and the corresponding base to the reaction system. In this case, a solvent such as benzene, acetone, dimethylformamide and the like is preferably used, and the reaction is preferably conducted by heating the reaction system at or below the boiling point of the solvent used. A preferred halogen for the halide of alcohol (XII) includes chlorine and bromine.

Representative examples of the compounds of this invention are illustrated below, but the present invention is not limited thereto.

| Compound No. | |
|---|---|
| 1. | 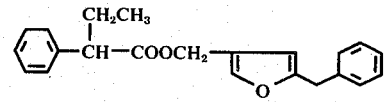 5'-Benzyl-3'-furylmethyl-α-ethyl-phenylacetate $n_D^{17}$ 1.5545 |
| 2. | 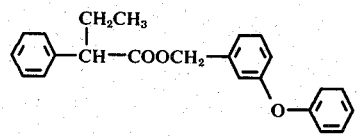 3'-Phenoxybenzyl-α-ethylphenylacetate $n_D^{22}$ 1.5712 |
| 3. | 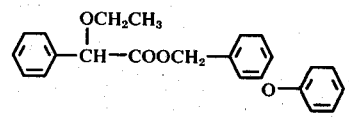 3'-Phenoxybenzyl-α-ethoxyphenylacetate $n_D^{24}$ 1.5275 |
| 4. | 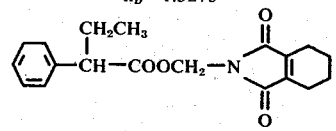 3',4',5',6'-Tetrahydrophthalimidomethyl-α-ethylphenylacetate $n_D^{22}$ 1.5403 |
| 5. | 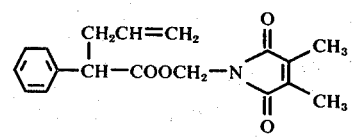 Dimethylmaleimidomethyl-α-allylphenylacetate $n_D^{22}$ 1.5349 |
| 6. | 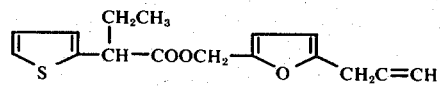 5'-Propargylfurfuryl-α-ethyl-2-thienylacetate $n_D^{22}$ 1.5835 |

| Compound No. | |
|---|---|
| 7. | 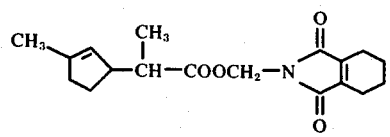
3',4',5',6'-Tetrahydrophthalimidomethyl-2-(3''-methyl-2''-cyclopentene-1''-yl)-propionate
$n_d^{23}$ 1.5648 |
| 8. | 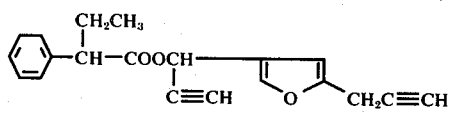
5'-Propargyl-α'-ethynyl-3'-furylmethyl-α-ethyl-phenylacetate
$n_D^{24.5}$ 1.5310 |
| 9. | 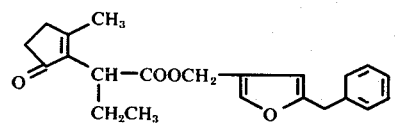
5'-Benzyl-3'-furylmethyl-2-(3''-methyl-2''-cyclopentenone-2''-yl)-butyrate
$n_D^{22}$ 1.5123 |
| 10. | 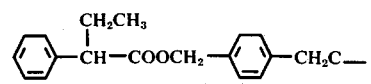
4'-Propargylbenzyl-α-ethylphenylacetate
$n_D^{23}$ 1.5039 |
| 11. | 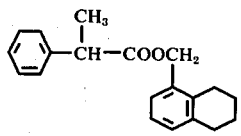
5'-(1',2',3',4'-Tetrahydronaphthalenyl)-methyl-α-methylphenylacetate
$n_D^{24}$ 1.5536 |
| 12. | 
5'-Benzyl-3'-thenyl-α-ethylphenylacetate
$n_D^{22}$ 1.5488 |
| 13. | 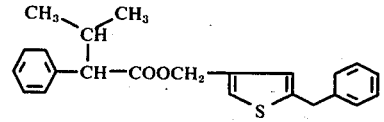
5'-Benzyl-3'-thenyl-αisopropyl-phenylacetate
$n_D^{22}$ 1.5613 |
| 14. | 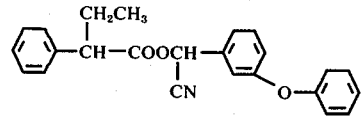
3'-Phenoxy-α'-cyanobenzyl-α-ethylphenylacetate
$n_D^{21}$ 1.5638 |
| 15. | 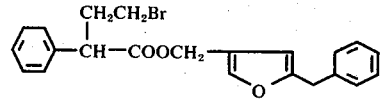
5'-Benzyl-3'-furylmethyl-α-(2''-bromoethyl)-phenylacetate |

| Compound No. | | |
|---|---|---|
| | $n_D^{23}$ 1.5911 | |
| 16. | 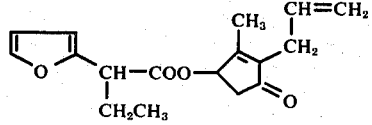 2'-Allyl-3'-methyl-2'-cyclopentene-1'-one-4'''-yl-α-ethyl-2-furylacetate $n_D^{22}$ 1.5118 | |
| 17. | 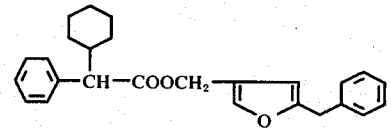 5-Benzyl-3'-furylmethyl-α-cyclohexyl-phenylacetate m.p. 51–53° C | |
| 18. | 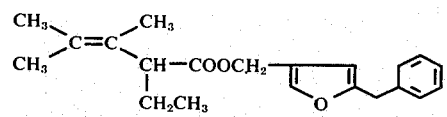 5'-Benzyl-3'-furylmethyl-2-ethyl-3,4-dimethyl-3-pentenoate $n_D^{23}$ 1.5417 | |
| 19. | 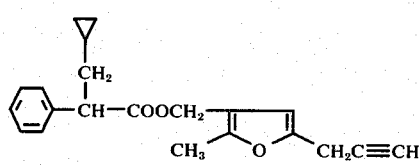 5'-Propargyl-2'-methyl-3'-furylmethyl-α-cyclopropylmethylphenylacetate $n_D^{24}$ 1.5632 | |
| 20. | 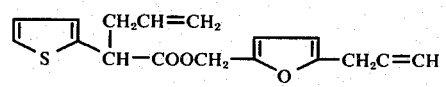 5'-Propargylfurfuryl-α-allyl-2-thenylacetate $n_D^{22}$ 1.5274 | |
| 21. | 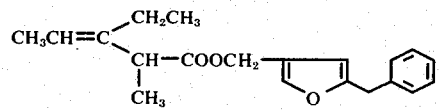 5'-Benzyl-3'-furylmethyl-2-methyl-3-ethyl-3-(cis,trans)-pentenoate $n_D^{21}$ 1.5693 | |
| 22. | 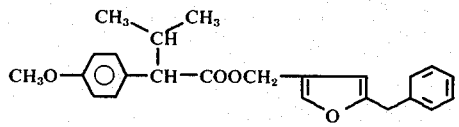 5'-Benzyl-3'-furylmethyl-α-isopropyl-4-methoxy-phenylacetate $n_D^{17}$ 1.5470 | |
| 23. | 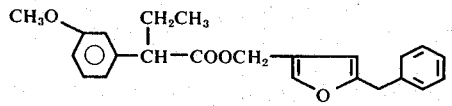 5'-Benzyl-3'-furylmethyl-α-ethyl-3-methoxyphenyl-acetate $n_D^{25}$ 1.5481 | |

| Compound No. | |
|---|---|
| 24. | 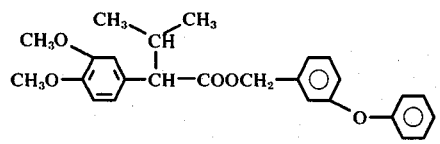
3'-Phenoxybenzyl-α-isopropyl-3,4-dimethoxyphenyl-acetate
$n_D^{25}$ 1.5655 |
| 25. | 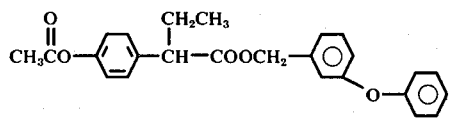
3'-Phenoxybenzyl-α-ethyl-4-acetoxyphenylacetate
$n_D^{25}$ 1.5621 |
| 26. | 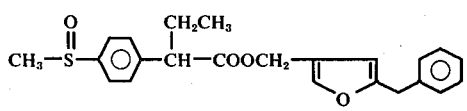
5'-Benzyl-3'-furylmethyl-α-ethyl-4-methylsulfoxy-phenylacetate
$n_D^{25}$ 1.5448 |
| 27. | 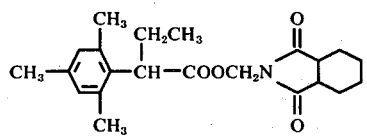
3',4',5',6'-Tetrahydrophthalimidomethyl-2-ethyl-2,4,6-trimethylphenylacetate
$n_D^{25}$ 1.5399 |
| 28. | 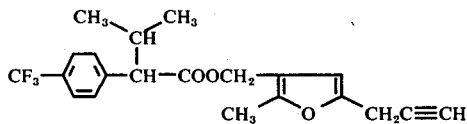
5'-Propargyl-2'-methyl-3'-furylmethyl-α-isopropyl-4-trifluoromethylphenylacetate
$n_D^{25}$ 1.5368 |
| 29. | 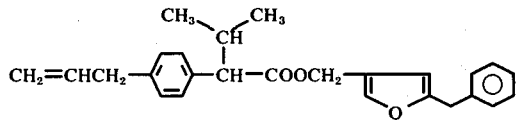
5'-Benzyl-3'-furylmethyl-α-isopropyl-4-allylphenyl-acetate
$n_D^{25}$ 1.5277 |
| 30. | 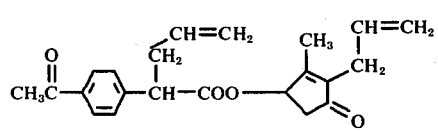
2'-Allyl-3'-methyl-2'-cyclopentene-1-one-4-yl-α-allyl-p-acetylphenylacetate
$n_D^{25}$ 1.5566 |
| 31. | 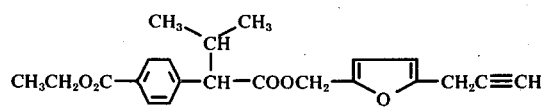
5'-Propargylfurfuryl-α-isopropyl-4-carbethoxy-phenylacetate
$n_D^{25}$ 1.5711 |

| Compound No. | |
|---|---|
| 32 | 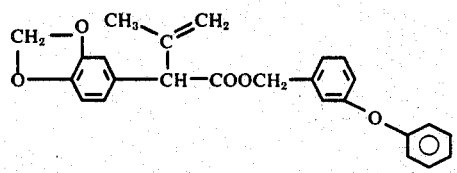
3'-Phenoxybenzyl-α-isopropenyl-3,4-methylenedioxy-phenylacetate
$n_D^{25}$ 1.5325 |
| 33. | 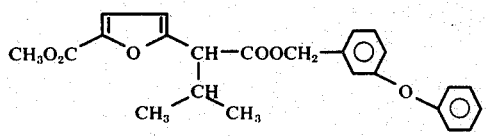
3'-Phenoxybenzyl-α-isopropyl-5-carbomethoxy-2-furylacetate
$n_D^{25}$ 1.5367 |
| 34. | 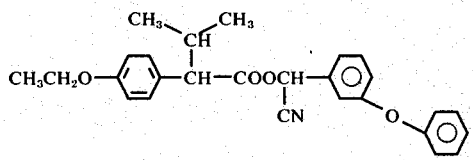
3'-Phenoxy-α-cyanobenzyl-α-isopropyl-4-ethoxy-phenylacetate
$n_D^{25}$ 1.5208 |
| 35. | 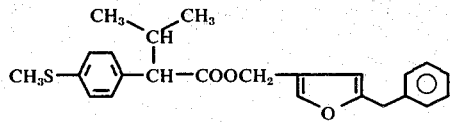
5'-Benzyl-3'-furylmethyl-α-isopropyl-4-methyl-thiophenylacetate
$n_D^{25}$ 1.5335 |
| 36. | 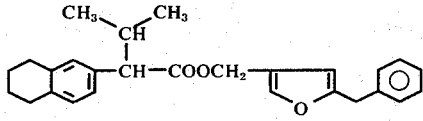
5'-Benzyl-3'-furylmethyl-α-isopropyl-1,2,3,4-tetrahydronaphthalene-6-yl-acetate
$n_D^{25}$ 1.3689 |
| 37. | 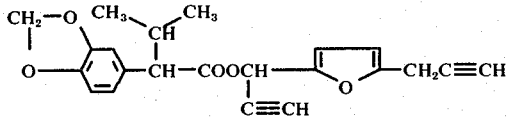
5'-Propargyl-2'-(α'-ethynyl)-furylmethyl-α-isopropyl-3,4-methylenedioxyphenylacetate
$n_D^{25}$ 1.5236 |
| 38. | 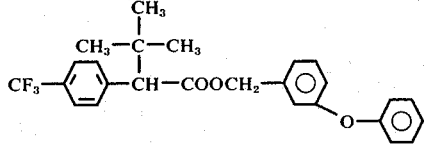
3'-Phenoxybenzyl-α-t-butyl-4-trifluoromethylphenyl-acetate
$n_D^{25}$ 1.5671 |
| 39. | 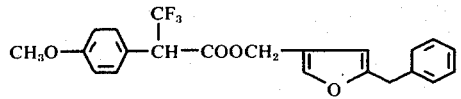 |

| Compound No. | |
|---|---|
| | 5'-Benzyl-3'-furylmethyl-α-trifluoromethyl-4-methoxyphenylacetate<br>$n_D^{25}$ 1.5474 |
| 40. | 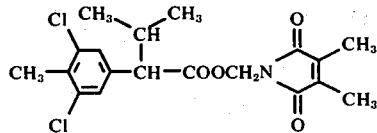<br>Dimethylmaleimidomethyl-α-isopropyl-3,5-dichloro-4-methylphenylacetate<br>$n_D^{25}$ 1.5239 |
| 41. | 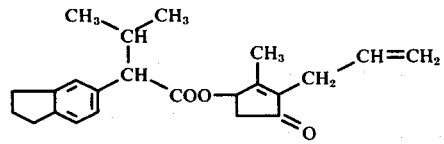<br>2'-Allyl-3'-methyl-2'-cyclopentene-1'-one-4'-yl-α'-isopropyl-5-indanylacetate<br>$n_D^{25}$ 1.5753 |
| 42. | 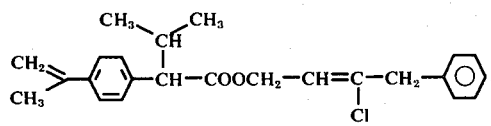<br>4'-Phenyl-3'-chloro-2'-butene-1'-yl-α-isopropyl-4-isopropenylphenylacetate<br>$n_D^{25}$ 1.5878 |
| 43. | 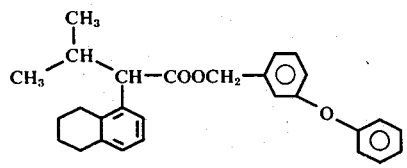<br>3'-Phenoxybenzyl-α-isopropyl-5-(1,2,3,4-tetrahydro)-naphthalenylacetate<br>$n_D^{25}$ 1.5660 |
| 44. | 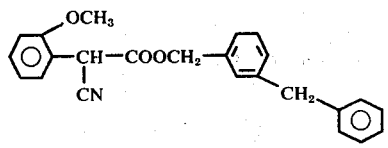<br>3'-Benzylbenzyl-α-cyano-2-methoxphenylacetate<br>$n_D^{25}$ 1.5702 |
| 45. | 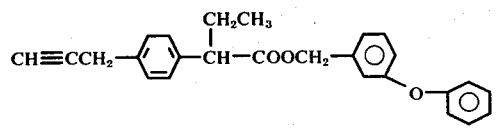<br>3'-Phenoxybenzyl-α-ethyl-4-propargylphenylacetate<br>$n_D^{25}$ 1.5513 |
| 46. | 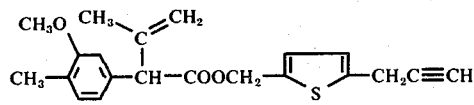<br>5'-Propargyl-2'-thenyl-α-isopropenyl-3-methoxy-4-methylphenylacetate<br>$n_D^{20}$ 1.5466 |

| Compound No. | |
|---|---|
| 47. | 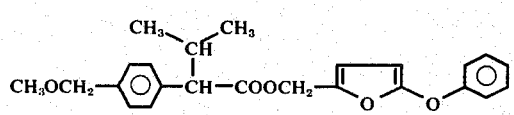
5'-Phenoxyfurfuryl-α-isopropyl-4-methoxymethyl-phenylacetate
$n_D^{25}$ 1.5738 |
| 48. | 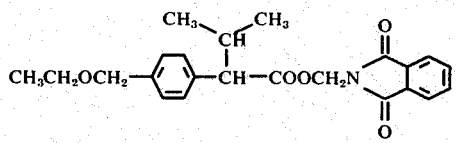
Phthalimidomethyl-α-isopropyl-4-ethoxymethyl-phenylacetate
$n_D^{25}$ 1.5221 |
| 49. | 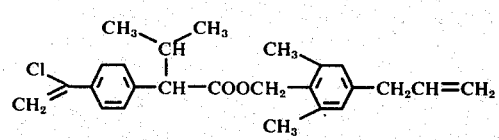
2',6'-Dimethyl-4'-allylbenzyl-α-isopropyl-4-1''-chloroethylene-1''-yl-phenylacetate
$n_D^{25}$ 1.5413 |
| 50. | 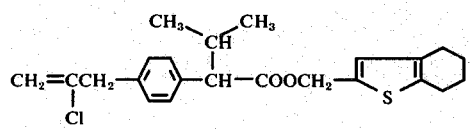
4',5'-Tetramethylene-2-thenyl-α-isopropyl-4-(2''-chloroallyl)-phenylacetate
$n_D^{25}$ 1.5239 |
| 51. | 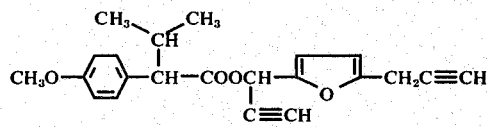
5'-Propargyl-2'-(α'-ethynyl)-furfuryl-α-isopropyl-4-methoxyphenylacetate
$n_D^{26}$ 1.5253 |
| 52. | 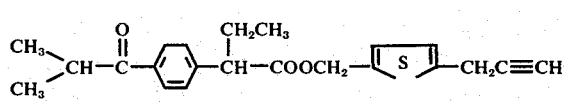
5'-Propargyl-2'-thenyl-α-ethyl-4-isobutyrylphenyl-acetate
$n_D^{25}$ 1.5549 |
| 53. | 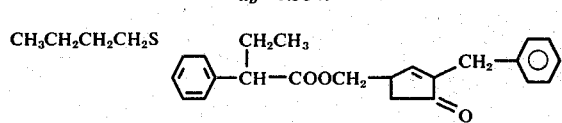
2'-Benzyl-2'-cyclopentene-1'-one-4'-yl-α-ethyl-3-butylthio-phenylacetate
$n_D^{25}$ 1.5508 |
| 54. | 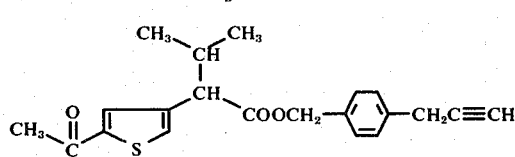
4'-Propargylbenzyl-α-isopropyl-5-acetyl-3-thienyl-acetate
$n_D^{22}$ 1.5259 |

-continued

| Compound No. | |
|---|---|
| 55. | 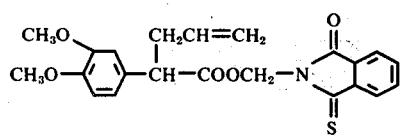<br>Monothiophthalimidomethyl-α-allyl-3,4-dimethoxy-phenylacetate<br>$n_D^{19}$ 1.5350 |
| 56. | 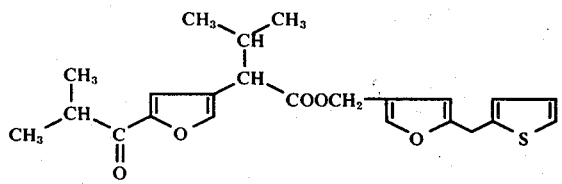<br>5'-(2''-Thenyl)-3'-furylmethyl-α-isopropyl-3-(5-isobutyryl)-furylacetate<br>$n_D^{22}$ 1.5324 |
| 57. | 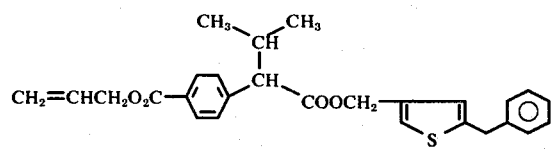<br>5'-Benzyl-3'-thenyl-α-isopropyl-3-carballyloxy-phenylacetate<br>$n_D^{25}$ 1.5556 |
| 58. | 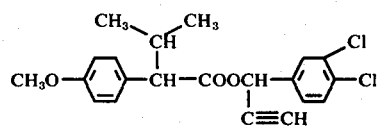<br>3',4'-Dichloro-α-ethynylbenzyl-α-isopropyl-4-methoxyphenylacetate<br>$n_D^{25}$ 1.5368 |
| 59. | 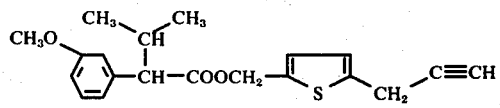<br>5'-Propargyl-2'-thenyl-α-isopropyl-3-methoxyphenyl-acetate<br>$n_D^{25}$ 1.5552 |
| 60. | 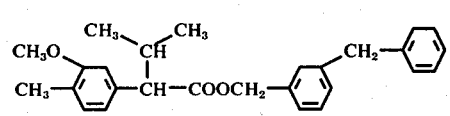<br>3'-Benzylbenzyl-α-isopropyl-3-methoxy-4-methyl-phenylacetate<br>$n_D^{25}$ 1.5509 |
| 61. | 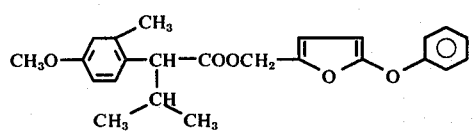<br>5'-Phenoxyfurfuryl-α-isopropyl-2-methyl-4-methoxy-phenylacetate<br>$n_D^{25}$ 1.5501 |
| 62. | 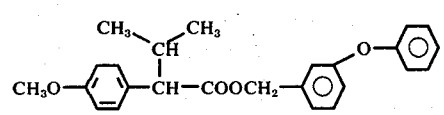<br>3'-Phenoxybenzyl-α-isopropyl-4-methoxyphenylacetate<br>$n_D^{19}$ 1.5878 |

-continued

| Compound No. | |
|---|---|
| 63. | 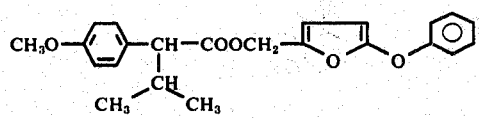
5′-Phenoxyfurfuryl-α-isopropyl-4-methoxyphenyl-acetate
$n_D^{19}$ 1.5878 |
| 64 | 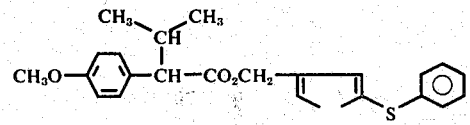
5′-Phenylthio-3′-furylmethyl-α-isopropyl-4-methoxyphenylacetate
$n_D^{16}$ 1.5371 |
| 65. | 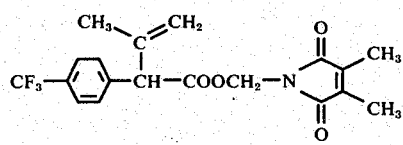
Dimethylmaleimidomethyl-α-isopropenyl-4-trifluoromethylphenylacetate
$n_D^{25}$ 1.5779 |
| 66. | 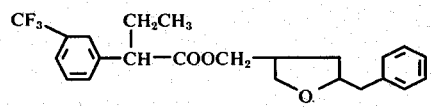
5′-Benzyl-3′-furylmethyl-α-ethyl-3-trifluoromethyl-phenylacetate
$n_D^{25}$ 1.5647 |
| 67. | 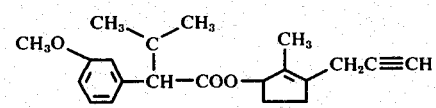
2′-Propargyl-3′-methyl-2′-cyclopentene-1′-one-4′-yl-d-isopropyl-3-methoxyphenylacetate
$n_D^{25}$ 1.5628 |
| 68. | 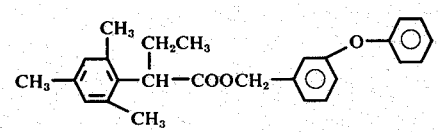
3′-Phenoxybenzyl-α-ethyl-2,4,6-trimethyl-3-nitro-phenylacetate
$n_D^{25}$ 1.5971 |
| 69. | 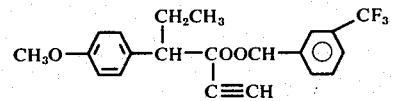
3′-Trifluoromethyl-α′-ethynylbenzyl-α-ethyl-4-methoxyphenylacetate
$n_D^{25}$ 1.5119 |
| 70. | 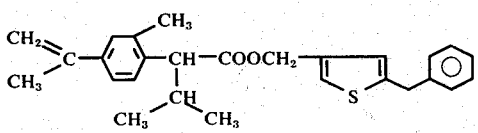
5′-Benzyl-3′-thenylmethyl-α-isopropyl-2-methyl-3-isopropenylphenylacetate
$n_D^{25}$ 1.5299 |

-continued

| Compound No. | |
|---|---|
| 71. | 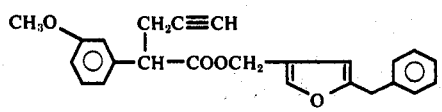
5'-Benzyl-3'-furylmethyl-α-propargyl-3-methoxy-phenylacetate
$n_D^{25}$ 1.5478 |
| 72. | 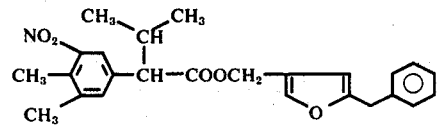
5'-Benzyl-3'-furylmethyl-α-isopropyl-3-nitro-4,5-dimethylphenylacetate
$n_D^{25}$ 1.5371 |
| 73. | 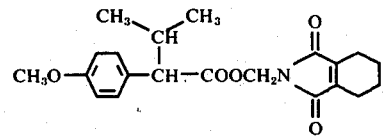
3',4',5',6'-Tetrahydrophthalimidomethyl-α-isopropyl-p-methoxyphenylacetate
$n_D^{25}$ 1.5365 |
| 74. | 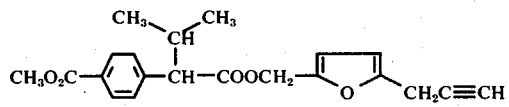
5'-Propargylfurfuryl-α-isopropyl-4-carbomethoxy-phenylacetate
$n_D^{25}$ 1.5335 |
| 75. | 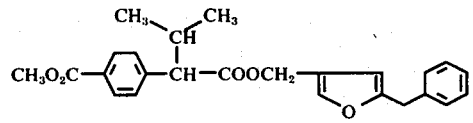
5'-Benzyl-3'-furylmethyl-α-isopropyl-4-carbomethoxy-phenylacetate
$n_D^{24}$ 1.5640 |
| 76. | 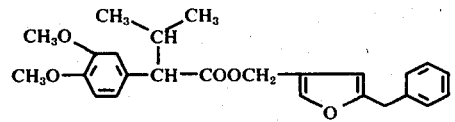
5'-Benzyl-3'-furylmethyl-α-isopropyl-3,4-dimethoxy-phenylacetate
$n_D^{25}$ 1.5456 |
| 77. | 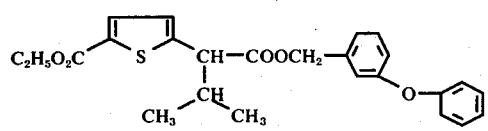
3'-Phenoxybenzyl-α-isopropyl-5-carbethoxy-2-thenylacetate
$n_D^{25}$ 1.5777 |
| 78. | 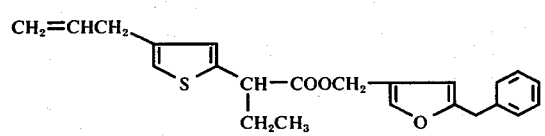
5'-Benzyl-3'-furylmethyl-α-ethyl-4-allyl-2-thenyl-acetate
$n_D^{25}$ 1.5510 |

| Compound No. | |
|---|---|
| 79. | 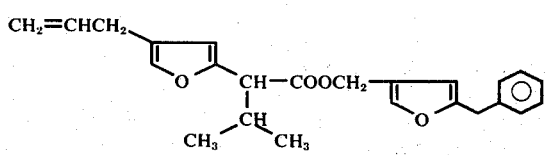<br>5'-Benzyl-3'-furylmethyl-α-isopropyl-4-allyl-2-furylacetate<br>$n_D^{25}$ 1.5356 |
| 80. | 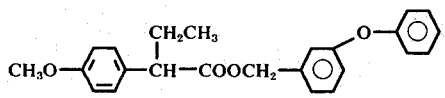<br>3'-Phenoxybenzyl-α-ethyl-4-methoxyphenylacetate<br>$n_D^{19}$ 1.5671 |
| 81. | 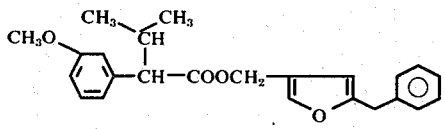<br>5'-Benzyl-3'-furylmethyl-α-isopropyl-3-methoxy-Phenylacetate<br>$n_D^{16}$ 1.5411 |
| 82. | 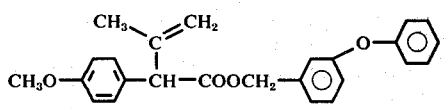<br>3'-Phenoxybenzyl-α-isopropenyl-4-methoxyphenylacetate<br>$n_D^{16}$ 1.5798 |
| 83. | 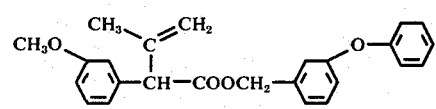<br>3'-Phenoxybenzyl-α-isopropenyl-3-methoxyphenylacetate<br>$n_D^{18}$ 1.5687 |
| 84. | 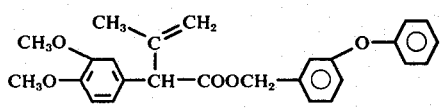<br>3'-Phenoxybenzyl-α-isopropenyl-3,4-dimethoxyphenyl-acetate<br>$n_D^{20}$ 1.5713 |
| 85. | 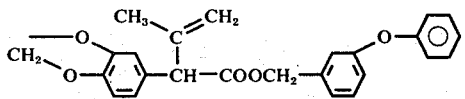<br>3'-Phenoxybenzyl-α-isopropenyl-3,4-methylenedioxy-phenylacetate<br>$n_D^{20}$ 1.5535 |
| 86. | 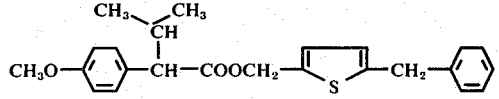<br>5'-Benzyl-2'-thenylmethyl-α-isopropyl-4-methoxy-phenylacetate<br>$n_D^{20}$ 1.5571 |
| 87. | 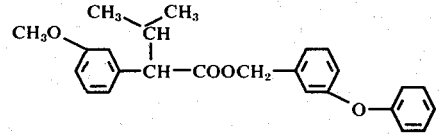 |

-continued

| Compound No. | |
|---|---|
| | 3'-Phenoxybenzyl-α-isopropyl-3-methoxypenylacetate<br>$n_D^{17}$ 1.5377 |
| 88. | 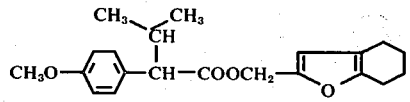<br>4',5'-Tetramethylenefurfuryl-α-isopropyl-4-methoxy-<br>phenylacetate<br>$n_D^{19}$ 1.5467 |
| 89. | 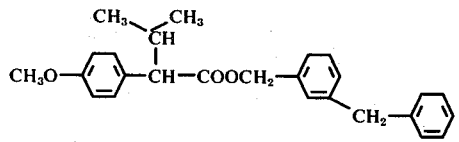<br>3'-Benzylbenzyl-α-isopropyl-4-methoxyphenylacetate<br>$n_D^{20}$ 1.5313 |
| 90. | 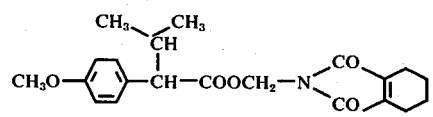<br>3',4',5',6'-Tetrahydrophthalimidomethyl-α-iso-<br>propenyl-4-methoxyphenylacetate<br>$n_D^{21}$ 1.5211 |
| 91. | 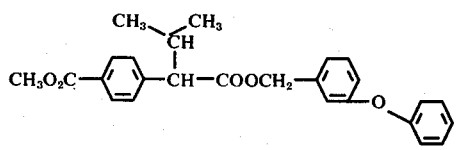<br>3'-Phenoxybenzyl-α-isopropyl-4-carbomethoxyphenyl-<br>acetate<br>$n_D^{20}$ 1.5413 |
| 92. | 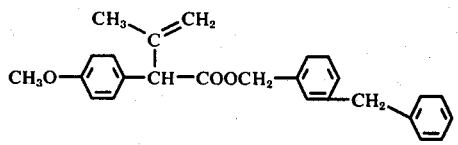<br>3'-Benzylbenzyl-α-isopropenyl-4-methoxyphenylacetate<br>$n_D^{19}$ 1.5339 |
| 93. | 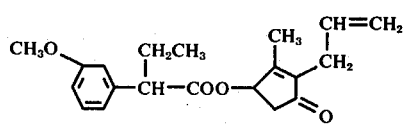<br>2'-Allyl-3'-methyl-2'-cyclopentene-1'-one-4-<br>α-ethyl-3-methoxyphenylacetate<br>$n_D^{19}$ 1.5211 |
| 94. | 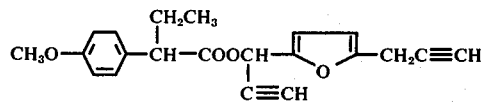<br>5'-Propargyl-α'-ethynylfurfuryl-α-ethyl-4-methoxy-<br>phenylacetate<br>$n_D^{20}$ 1.5467 |
| 95. | 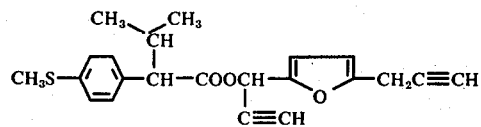<br>5'-Propargyl-α'-ethynylfurfuryl-α-isopropyl-4-<br>methylthiophenylacetate<br>$n_D^{20}$ 1.5518 |

-continued

| Compound No. | |
|---|---|
| 96. | 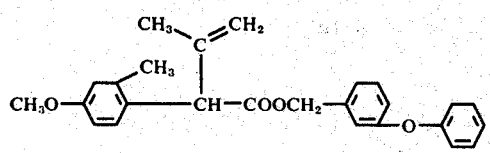<br>3'-Phenoxybenzyl-α-isopropenyl-2-methyl-4-methoxy-phenylacetate<br>$n_D^{20}$ 1.5396 |
| 97. | 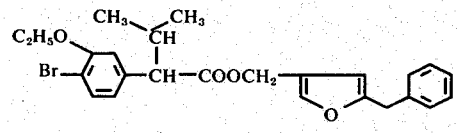<br>5'-Benzyl-3'-furylmethyl-α-isopropyl-3-ethoxy-4-bromophenylacetate<br>$n_D^{20}$ 1.5218 |
| 98. | 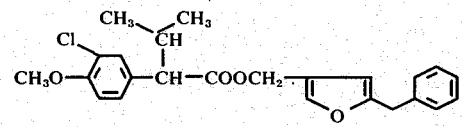<br>5'-Benzyl-3'-furylmethyl-α-isopropyl-3-chloro-4-methoxyphenylacetate<br>$n_D^{20}$ 1.5416 |
| 99. | 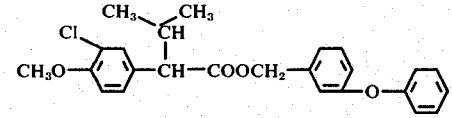<br>3'-Phenoxybenzyl-α-isopropyl-3-chloro-4-methoxy-phenylacetate<br>$n_D^{20}$ 1.5467 |
| 100. | 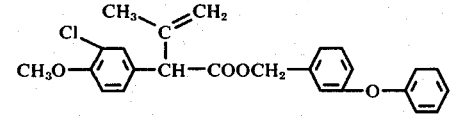<br>3'-Phenoxybenzyl-α-isopropenyl-3-chloro-4-methoxy-phenylacetate<br>$n_D^{20}$ 1.5331 |
| 101. | 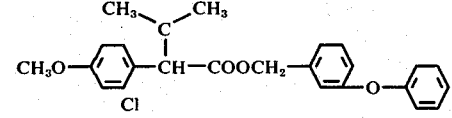<br>3'-Phenoxybenzyl-α-isopropyl-2-chloro-4-methoxy-phenylacetate<br>$n_D^{20}$ 1.5476 |
| 102. | 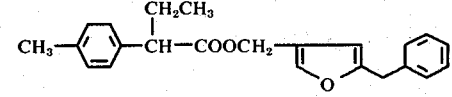<br>5'-Benzyl-3'-furylmethyl-α-ethyl-4-methylphenyl-acetate<br>$n_D^{25}$ 1.5474 |
| 103. | 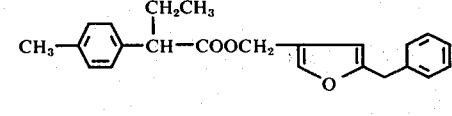<br>5'-Benzyl-3'-furylmethyl-α-isopropyl-4-methyl-phenylacetate<br>$n_D^{25}$ 1.5433 |

-continued

| Compound No. | | |
|---|---|---|
| 104. | 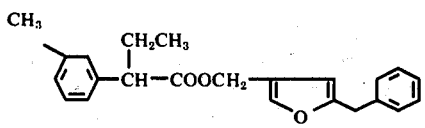 | |
| | 5'-Benzyl-3'-furylmethyl-α-ethyl-3-methylphenyl-acetate $n_D^{25}$ 1.5470 | |
| 105. | 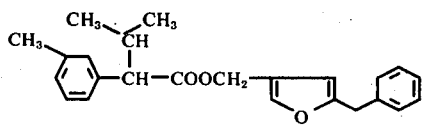 | |
| | 5'-Benzyl-3'-furylmethyl-α-isopropyl-3-methyl-phenylacetate $n_D^{25.5}$ 1.5430 | |
| 106. | 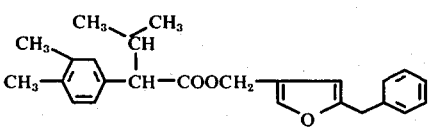 | |
| | 5'-Benzyl-3'-furylmethyl-α-isopropyl-3,4-dimethyl-phenylacetate $n_D^{25.5}$ 1.5238 | |
| 107. | 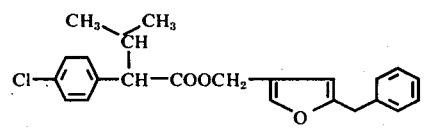 | |
| | 5'-Benzyl-3'-furylmethyl-α-isopropyl-4-chloro-phenylacetate $n_D^{25.5}$ 1.5241 | |
| 108. | 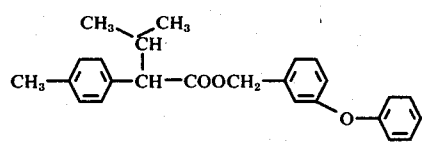 | |
| | 3'-Phenoxybenzyl-α-isopropyl-4-methylphenylacetate $n_D^{28.5}$ 1.5596 | |
| 109. | 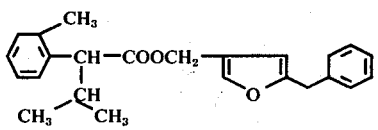 | |
| | 5'-Benzyl-3'-furylmethyl-α-isopropyl-2-methyl-phenylacetate $n_D^{26.5}$ 1.5431 | |
| 110. | 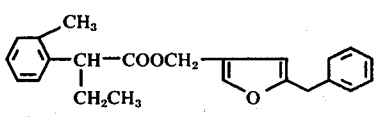 | |
| | 5'-Benzyl-3'-furylmethyl-α-ethyl-2-methylphenyl-acetate $n_D^{26.5}$ 1.5501 | |
| 111. | 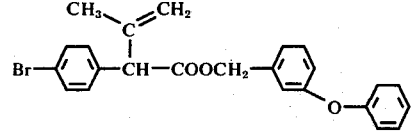 | |
| | 3'-Phenoxybenzyl-α-isopropenyl-4-bromophenylacetate $n_D^{20}$ 1.5278 | |

| Compound No. | |
|---|---|
| 112. | 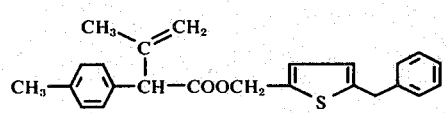<br>5'-Benzyl-2'-thenyl-α-isopropenyl-4-methylphenyl-<br>acetate<br>$n_D^{20}$ 1.5439 |
| 113. | 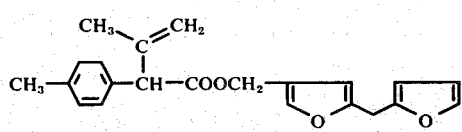<br>5'-Furfuryl-3'-furylmethyl-α-isopropenyl-4-methyl-<br>phenylacetate<br>$n_D^{20}$ 1.5411 |
| 114. | 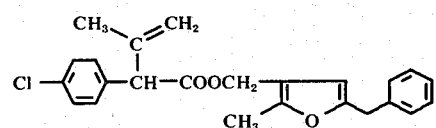<br>5'-Benzyl-2'-methyl-3'-furylmethyl-α-isopropenyl-4-<br>chlorophenylacetate<br>$n_D^{25}$ 1.5212 |
| 115. | 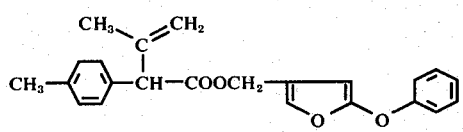<br>5'-Phenoxy-3'-furylmethyl-α-isopropenyl-4-methyl<br>phenylacetate<br>$n_D^{25}$ 1.5471 |
| 116. | 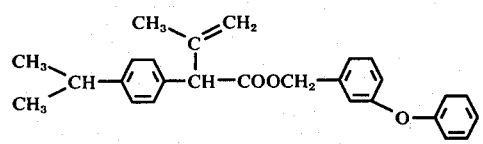<br>3'-Phenoxybenzyl-α-isopropenyl-4-isopropylphenyl-<br>acetate<br>$n_D^{20}$ 1.5218 |
| 117. | 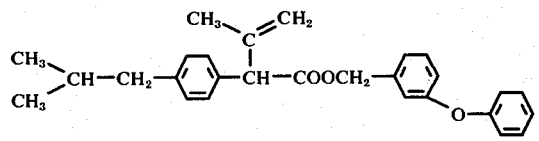<br>3'-Phenoxybenzyl-α-isopropenyl-4-isobutylphenyl-<br>acetate<br>$n_D^{20}$ 1.5236 |
| 118. | 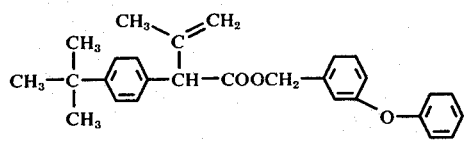<br>3'-Phenoxybenzyl-α-isopropenyl-4-t-butylphenyl-<br>acetate<br>$n_D^{20}$ 1.5311 |
| 119. | 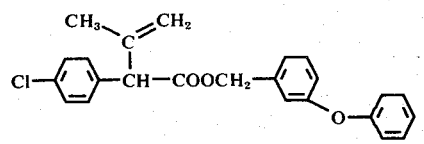<br>3'-Phenoxybenzyl-α-isopropenyl-4-chlorophenylacetate<br>$n_D^{21}$ 1.5322 |

| Compound No. | |
|---|---|
| 120. | 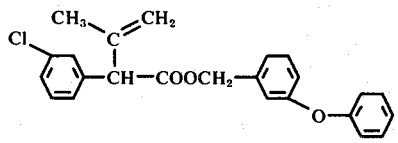 3'-Phenoxybenzyl-α-isopropenyl-3-chlorophenylacetate $n_D^{21}$ 1.5393 |
| 121. | 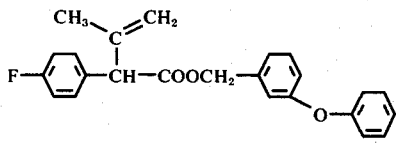 3'-Phenoxybenzyl-α-isopropenyl-4-fluorophenylacetate $n_D^{20}$ 1.5363 |
| 122. | 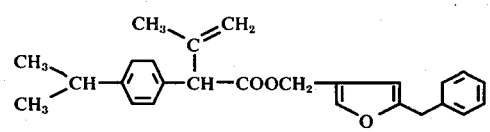 5'-Benzyl-3'-furylmethyl-α-isopropenyl-4-isopropyl-phenylacetate $n_D^{19}$ 1.5428 |
| 123. | 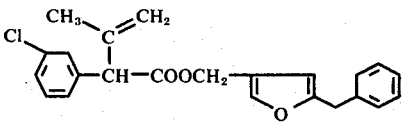 5'-Benzyl-3'-furylmethyl-α-isopropenyl-3-chloro-phenylacetate $n_D^{17}$ 1.5411 |
| 124. | 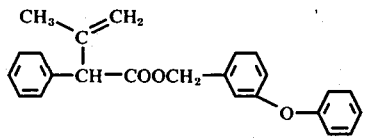 3'-Phenoxybenzyl-α-isopropenyl-phenylacetate $n_D^{20}$ 1.5396 |
| 125. | 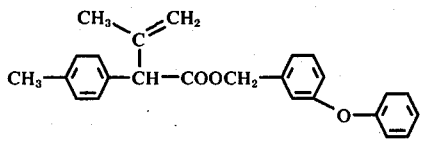 3'-Phenoxybenzyl-α-isopropenyl-4-methylphenylacetate $n_D^{20}$ 1.5378 |
| 126. | 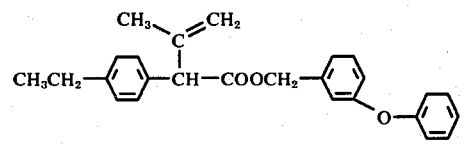 3'-Phenoxybenzyl-α-isopropenyl-4-ethylphenylacetate $n_D^{20}$ 1.5441 |
| 127. | 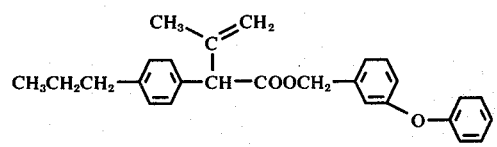 3'-Phenoxybenzyl-α-isopropenyl-4-n-propyl-phenyl acetate $n_D^{20}$ 1.5466 |

| Compound No. | |
|---|---|
| 128. | 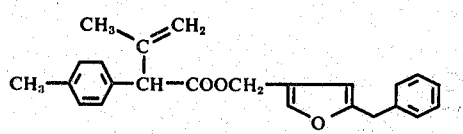<br>5'-Benzyl-3'-furylmethyl-α-isopropenyl-4-methyl-phenylacetate<br>$n_D^{20}$ 1.5398 |

The process for preparing the esters in accordance with the present invention is illustrated by the following Preparations, but the present invention is not limited thereto.

PREPARATION 1

Preparation of 5'-benzyl-3'-furylmethyl-α-ethyl phenylacetate (Compound No. 1)

6.20 g (0.02 mole) of α-ethylphenylacetic anhydride and 3.76 g (0.02 mole) of 5-benzyl-3-furylmethylalcohol were dissolved in 50 ml of dry pyridine and the mixture was stirred at room temperature for 2 hours. The resulting reaction mixture was poured into 100 g of ice water and extracted with three 20 ml portions of ethyl ether. The combined ether layer was then extracted with two 20 ml portions of 5% aqueous sodium hydroxide to remove α-ethylphenylacetic acid as a by-product. The ether layer was washed successively with 10% hydrochloric acid, saturated aqueous sodium bicarbonate and saturated sodium chloride, dried over anhydrous sodium sulfate, and the ether was removed under reduced pressure to obtain 6.25 g of crude ester as a pale yellow oily substance. The resulting oily substance was then purified by column chromatography using 120 g of activated alumina and a developing solvent of benzene-n-hexane (1:3) to obtain 5.68 g (85% theoretical yield) of the desired ester as a colorless oily substance.

$n_D^{17}$ 1.5545

$v_{max}^{film}$ 3005, 1724, 1550, 1407, 1180, 806 cm$^{-1}$ $\delta_{ppm}^{CCl_4}$ 7.16 (S. 5H), 7.15 (S. 5H), 7.2 (1H), 5.79 (bs. 1H), 4.78 (S. 2H), 3.78 (S. 2H), 3.31 (t. 1H, J=7Hz), 1.3 - 2.3 (m. 2H), 0.83 (t. 3H, J=7Hz)

PREPARATION 2

Preparation of m-phenoxybenzyl -ethylphenylacetate (Compound No. 2)

2.00 g (0.01 mole) of m-phenoxybenzyl alcohol and 1.19 g (0.015 mole) of dry pyridine were dissolved in 20 ml of benzene, and 1.83 g (0.01 mole) of α-ethylphenylacetyl chloride dissolved in 5 ml of dry benzene was added dropwise thereto under ice-cooling. After completion of addition, the mixture was stirred at room temperature for 3 hours to complete the reaction, and the reaction mixture was poured into 30 g of ice-water. The mixture was separated, and the aqueous layer was extracted with two 10 ml portions of benzene. The combined benzene layer was washed successively with 5% hydrochloric acid, saturated aqueous sodium bicarbonate and saturated aqueous sodium chloride, and benzene was removed under reduced pressure. The resulting crude ester was charged onto a column packed with 40 g of activated alumina using a mixture of benzene-n-hexane (1.3) as an eluent to obtain 3.15 g (91% theoretical yield) of the purified ester.

$n_D^{22}$ 1.5712

$v_{max}^{film}$ 3030, 1740, 1590, 1470, 1260, 1220, 1160 cm$^{-1}$ $\delta_{ppm}^{CCl_4}$ 7.4 − 5.8 (m. 14H), 4.95 (S. 2H), 3.48 (t. 1H, J=8Hz), 2.3 − 1.1 (m. 2H), 0.85 (t. 3H, J=8Hz)

PREPARATION 17

Preparation of 5'-benzyl-3'-furylmethyl-α-cyclohexylphenylacetate (Compound No. 17) 2.82 g (0.015 mole) of 5-benzyl-3-furylmethyl alcohol and 2.22 g (0.01 mole) of ethyl-α-cyclohexylphenylacetate were dissolved in 50 ml of dry toluene and 0.1 g of sodium hydride was added thereto as a catalyst. The mixture was charged into a Teflon Spinning Band rectification tower and ethanol formed as a by-product was removed while heating and stirring. The reaction was completed in about 1 hour, and the reaction mixture was allowed to stand and cooled to room temperature and poured into 30 g of ice-water. The layers were separated to remove the toluene layer and the toluene layer was washed with saturated aqueous sodium chloride. Toluene was removed under reduced pressure, and the resulting crude ester was subjected to a column packed with 50 g of activated alumina using benzene-n-hexane (1:3) as an eluent to obtain 2.79 g (72% theoretical yield) of the purified ester as white crystals. Melting point, 51°-53° C.

$v_{max}^{nujol}$ 3035, 1738, 1606, 1500, 1454, 1155 cm$^{-1}$ $\delta_{ppm}^{CCl_4}$ 7.3 − 6.9 (m. 11H), 5.80 (bs. 1H), 4.77 (AB. q 2H), 3.70 (S. 2H), 3.06 (d. 2H, J=10Hz), 2.1 − 0.6 (m. 10H)

PREPARATION 5

Preparation of dimethylmaleimidomethyl-α-allylphenylacetate (Compound No. 5).

1.74 g (0.01 mole) of N-chloromethyldimethylmaleimide and 2.93 g (0.01 mole) of silver α-allylphenylacetate were added to 25 ml of dimethylformamide and the mixture was allowed to stand overnight at room temperature. The precipitated crystals were filtered and dimethylformamide was distilled off under reduced pressure. The resulting crude ester was subjected to a silica gel column (90 g) using a mixture of chloroform-carbon tetrachloride (2:1) as an eluent to obtain 2.43 g (75% theoretical yield) of the desired ester as a white oily substance.

$n_D^{22.0}$ 1.5349

$v_{max}^{film}$ 1780, 1740, 1720, 1640, 1600, 1140, 910 cm$^{-1}$ $\delta_{ppm}^{CDCl_3}$ 7.15 (S. 5H), 6.0 − 4.9 (m. 3H), 3.48 (t. 3H, J=10Hz), 3.0 − 2.0 (m. 2H), 2.0 (S. 6H)

PREPARATION 22

Preparation of 5'-benzyl-3'-furylmethyl-α-isopropyl-4-methoxyphenylacetate (Compound No. 22)

1.90 g (0.01 mole) of 5'-benzyl-3-furfuryl alcohol and 1.58 g (0.02 mole) of pyridine were dissolved in 50 ml of dry benzene, and 2.30 g (0.01 mole) of α-isopropyl-4-methoxyphenylacetyl chloride dissolved in 5 ml of dry benzene was added dropwise to the solution over about 30 minutes. After completion of the addition, the mixture was stirred at room temperature for 3 hours to complete the reaction. The reaction mixture was poured into 50 g of ice-water followed by separating the benzene layer, and the aqueous layer was extracted with two 20 ml portions of benzene. The combined benzene layer was washed successively with 5% hydrochloric acid, saturated aqueous sodium bicarbonate and saturated aqueous sodium chloride. A yellow oily substance obtained after removal of benzene was subjected to a column packed with 25 g of activated alumina using benzene-n-hexane (1:3) as an eluent to obtain 3.33 g (88.0% theoretical yield) of the purified ester as a colorless oily substance.

$n_D^{17}$ 1.5470
$v_{max.}^{film}$ 1735, 1617, 1515, 1250, 1032, 830, 730 cm$^{-1}$
$\delta_{ppm}^{CCl_4}$ 0.65 (d, 3H, J=7Hz), 0.95 (d. 3H, J=7Hz), 1.7 − 2.5 (m. 1H), 2.97 (d. 1H, J=11Hz), 3.67 (S. 3H), 3.81 (S. 2H), 4.78 (d.d. 2H), 5.83 (b.S. 1H), 6.90 (d.d. 4H), 7.1 − 7.3 (m. 6H)

PREPARATION 27

Preparation of 3,4,5,6-tetrahydrophthalimidomethyl-α-ethyl-2,4,6-trimethylphenylacetate (Compound No. 27)

10.31 g (0.05 mole) of α-ethyl-2,4,6-trimethylphenylacetic acid and 9.05 g (0.05 mole) of 3,4,5,6-tetrahydrophthalimidomethylol were dissolved in 100 ml of dry benzene, and 16.51 g (0.08 mole) of dicyclohexylcarbodiimide was added to the solution. The mixture was then allowed to stand overnight in a sealed vessel. On next day, the mixture was heated at reflux to complete the reaction, and, after allowing to cool, the precipitated dicyclohexylurea was separated by filtration. A viscous oily substance obtained by concentration of the filtrate was subjected to a silica gel column (360 g) to obtain 11.3 g (61.18% theoretical yield) of the purified ester as a colorless viscous oily substance.

$n_D^{25}$ 1.5399
$v_{max.}^{film}$ 1780, 1740, 1720, 1511, 1405, 1140 cm$^{-1}$
$\delta_{ppm}^{CCl_4}$ 0.85 (t. 3H, J=7Hz), 1.5 − 2.3 (m. 2H), 2.3 (b.S. 9H), 3.32 (t. 3H, J=8Hz), 1.5 − 2.0 (m. 4H), 2.0 − 2.5 (m. 4H), 5.34 (d.d. 2H), 7.0 − 7.3 (m. 2H)

PREPARATION 47

Preparation of 2'-allyl-3'-methyl-2'-cyclopentene-1'-one-4'-yl-α-ethyl-3-methoxyphenylacetate (Compound No. 93)

7.41 g (0.02 mole) of α-ethyl-3-methoxyphenylacetic anhydride and 1.52 g (0.01 mole) of 2-allyl-3-methyl-4-hydroxy-2-cylopentene-1-one were dissolved in 50 ml of dry pyridine, and the mixture was stirred overnight at room temperature. On next day, the reaction mixture was poured into 100 g of icewater and extracted with three 20 ml portions of ethyl ether. The combined ether layer was then extracted with two 30 ml portions of 5% aqueous sodium hydroxide to remove a carboxylic acid formed as a by-product. The ether layer was washed successively with 10% aqueous hydrochloric acid, saturated aqueous sodium bicarbonate and saturated aqueous sodium chloride and dried over anhydrous sodium sulfate. Removal of ether under reduced pressure yielded 3.2 g of a crude ester. The product was then subjected to a column packed with 20 g of activated alumina using benzene-n-hexane (1:3) as an eluent to obtain 2.73 g (83.1% theoretical yield) of the desired ester.

$n_D^{19}$ 1.5211
$v_{max.}^{film}$ 1730, 1710, 1150, 1140, 1000, 910 cm$^{-1}$
$\delta_{ppm}^{CCl_4}$ 0.90 (t. 3H, J=8Hz), 1.5 − 3.0 (m. 11H), 3.36 (t. 1H, J=9Hz), 3.67 (S. 1H), 4.7 − 6.0 (m. 3H), 6.5 − 6.9 (m. 4H)

PREPARATION 46

Preparation of 3'-phenoxybenzyl-α-isopropyl-3-methoxyphenylacetate (Compound No. 87)

8.01 g (0.04 mole) of m-phenoxybenzyl alcohol and 7.09 g (0.03 mole) of ethyl α-isopropyl-3-methoxyphenylacetate were dissolved in 100 ml of dry toluene, and 0.1 g of sodium hydride was added thereto as a catalyst. The mixture was then charged in a Teflon Spinning Band rectifier tower having a length of 50 cm and heated while stirring. The reaction was completed in about 3 hours by removing ethanol as an azeotropic distillation with toluene at the top of the tower. After allowing to stand and cooling the mixture was poured into cold water to separate layers. Removal of toluene by distillation under reduced pressure yielded 11.5 g of a crude ester. The product was then subjected to a column packed with 55 g of activated alumina using benzene-n-hexane (1:3) as an eluent to obtain 10.12 g (86.4% theoretical yield based on the starting ethyl ester of the desired ester.

$n_D^{17}$ 1.5377
$v_{max.}^{film}$ 3060, 1738, 1590, 1490, 1255, 1145, 775, 690 cm$^{-1}$
$\delta_{ppm}^{CCl_4}$ 0.70 (d. 3H, J=7Hz), 0.97 (d. 3H, J=7Hz), 0.9 − 2.6 (m. 1H), 3.08 (d. 1H, J=11Hz), 3.65 (S. 3H), 4.95 (AB Type d.d. 2H), 6.5 − 7.4 (m. 13H)

PREPARATION 48

Preparation of 3'-phenoxybenzyl-2-(1',2',3',4'-tetrahydronaphthalene-8'-yl) isovalerate (Compound No. 43)

3.95 g (0.015 mole) of m-phenoxybenzyl bromide, 2.32 g (0.01 mole) of 2-(1',2',3',4'-tetrahydronaphthalene-8'-yl) isovaleric acid and 2.02 g (0.02 mole) of triethylamine were added to 50 ml of dimethylformamide and the mixture was stirred overnight at room temperature. The reaction mixture was poured into 50 g of ice-water and extracted with three 30 ml portions of ethyl ether. The combined ether layer was washed successively with 5% hydrochloric acid, saturated aqueous sodium bicarbonate and saturated aqueous sodium chloride and dried over anhydrous sodium sulfate. Removal of ethyl ether by distillation under reduced pressure yielded a crude ester which was then subjected to a column packed with 20 g of activated alumina using benzene-n-hexane (1:3) as an eluent to obtain 3.45 g (83.2% theoretical yield based on the carboxylic acid stating material) of the desired ester as a colorless oily substance.

$n_D^{19}$ 1.5660

$\nu_{max.}^{film}$ 3060, 1736, 1588, 1490, 1255, 770, 690 cm$^{-1}$
$\delta_{ppm}^{CCl_4}$ 0.68 (d. 3H, J=7Hz), 1.03 (d. 3H, J=7Hz), 1.5 − 2.0 (m. 4H), 2.1 − 2.6 (m. 1H), 2.5 − 3.0 (m. 4H), 2.48 (d. 1H, J=11Hz), 4.74 (S. H), 6.6 − 7.4 (m. 12H)

In a similar manner as described in Preparations 1, 2, 5, 17, 22, 27, 46 and 48, the compounds listed in Table below were obtained. In the table, the symbols a, b, c, d and e stand for the following esterification methods.
  a: Esterification using an acid chloride.
  b: Esterification using an acid anhydride.
  c: Dehydration esterification of an acid and an alcohol with dicyclohexylcarbodiimide in an inert solvent.
  d: Esterification by transesterification using sodium hydride as a catalyst in toluene.
  e: Esterification using a silver or a triethylammonium salt of acid and a halide of an alcohol.

Representative compounds of this invention prepared by the above methods are shown below, but they are not to be construed as limiting the present invention.

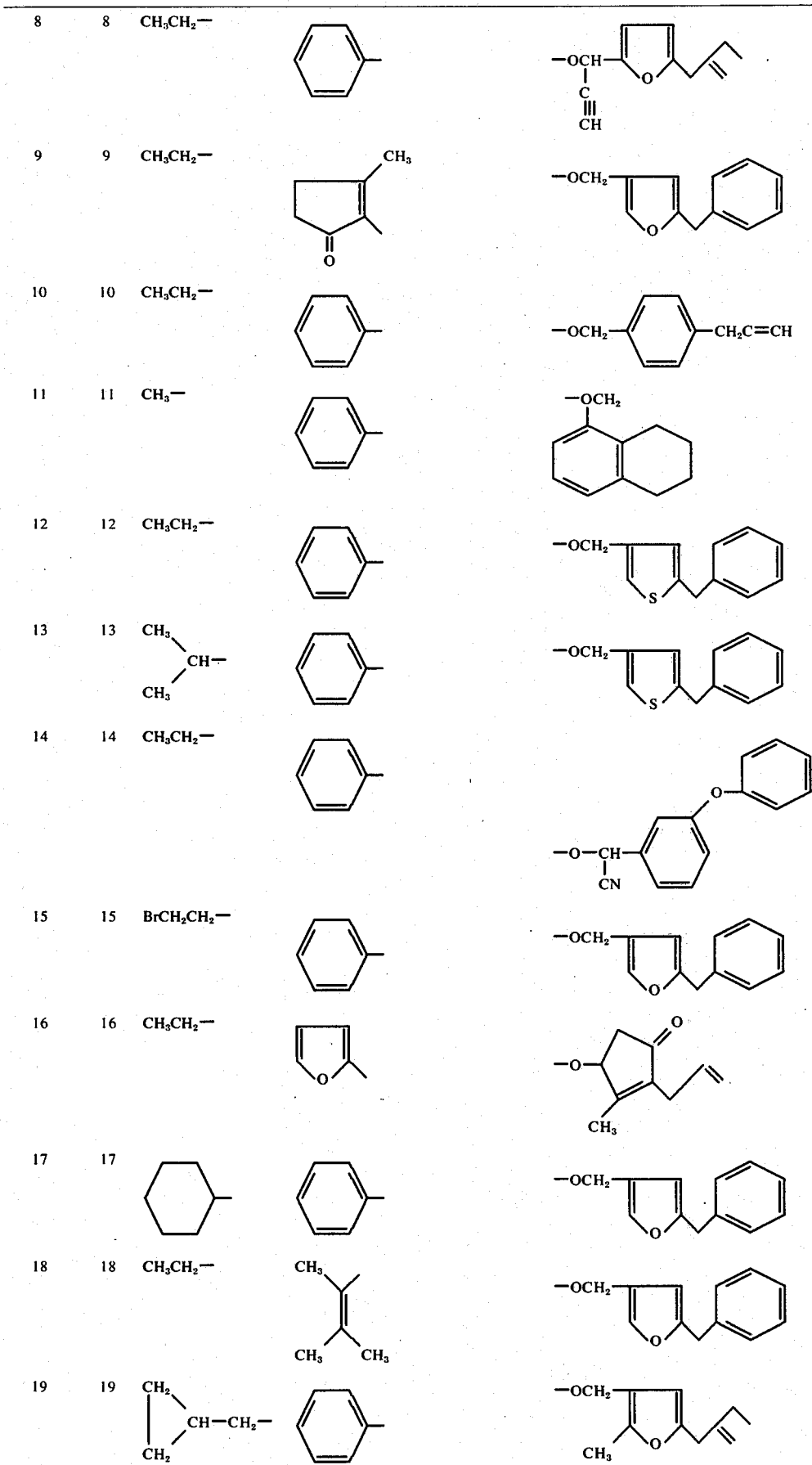

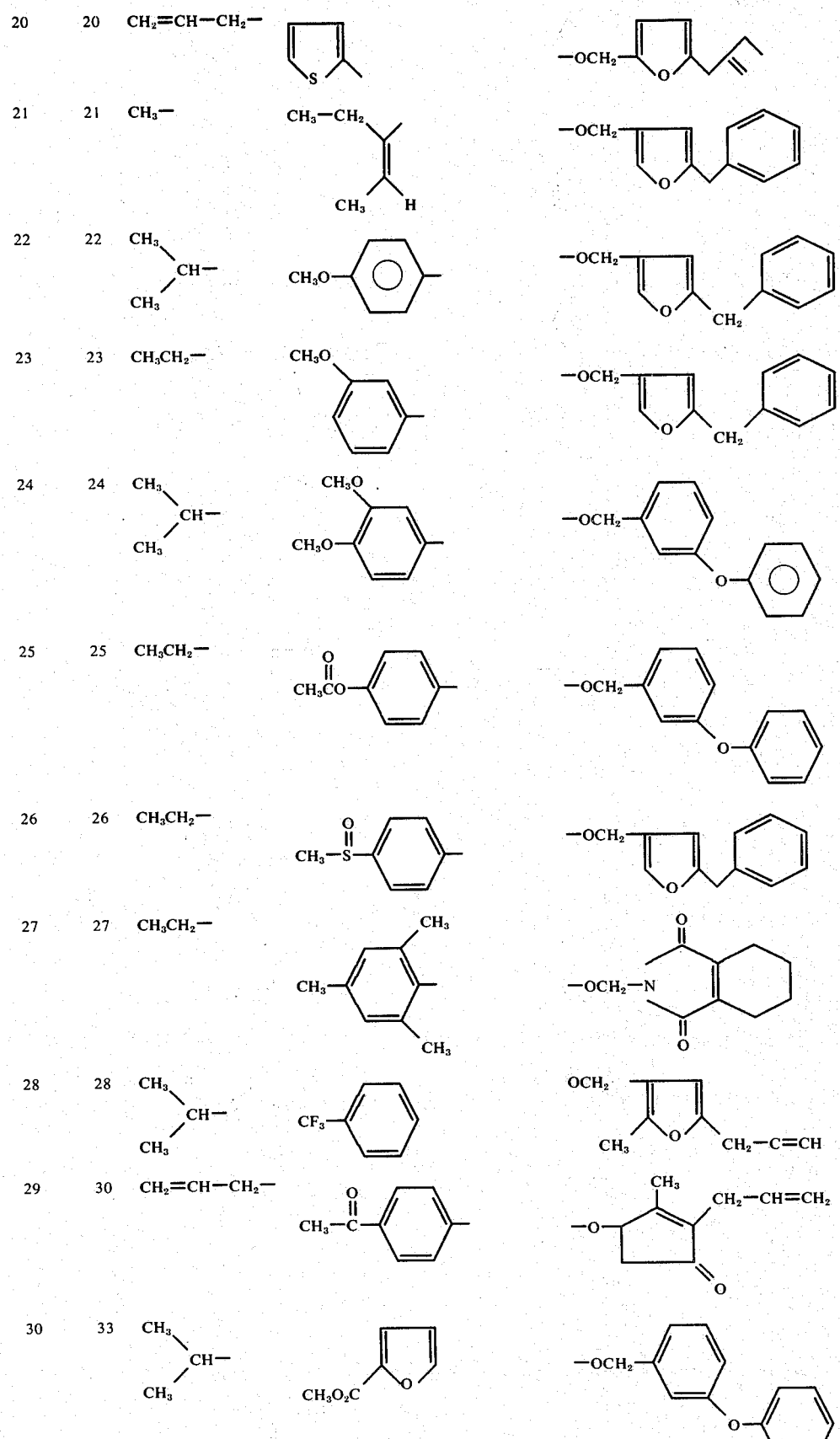

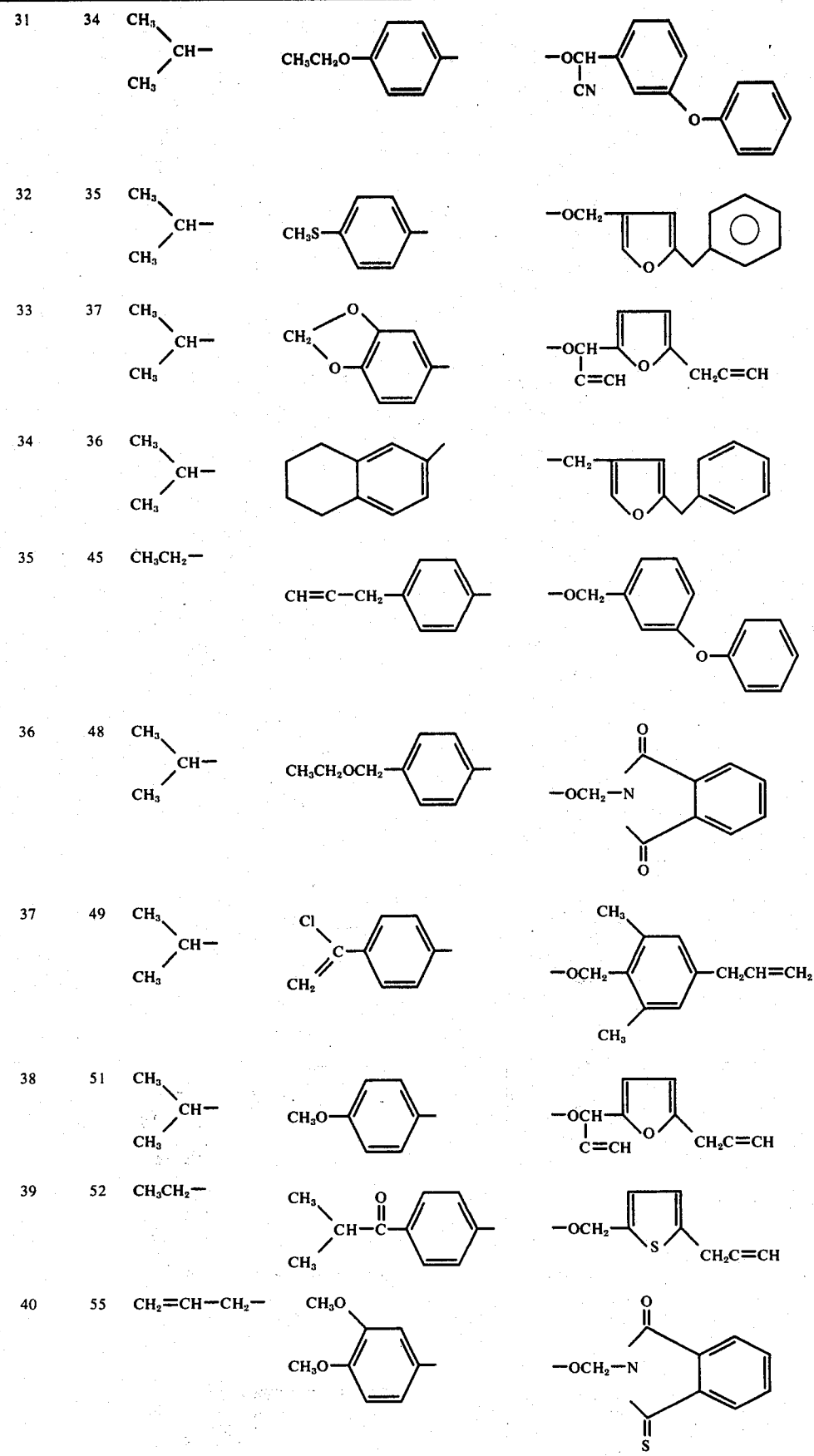

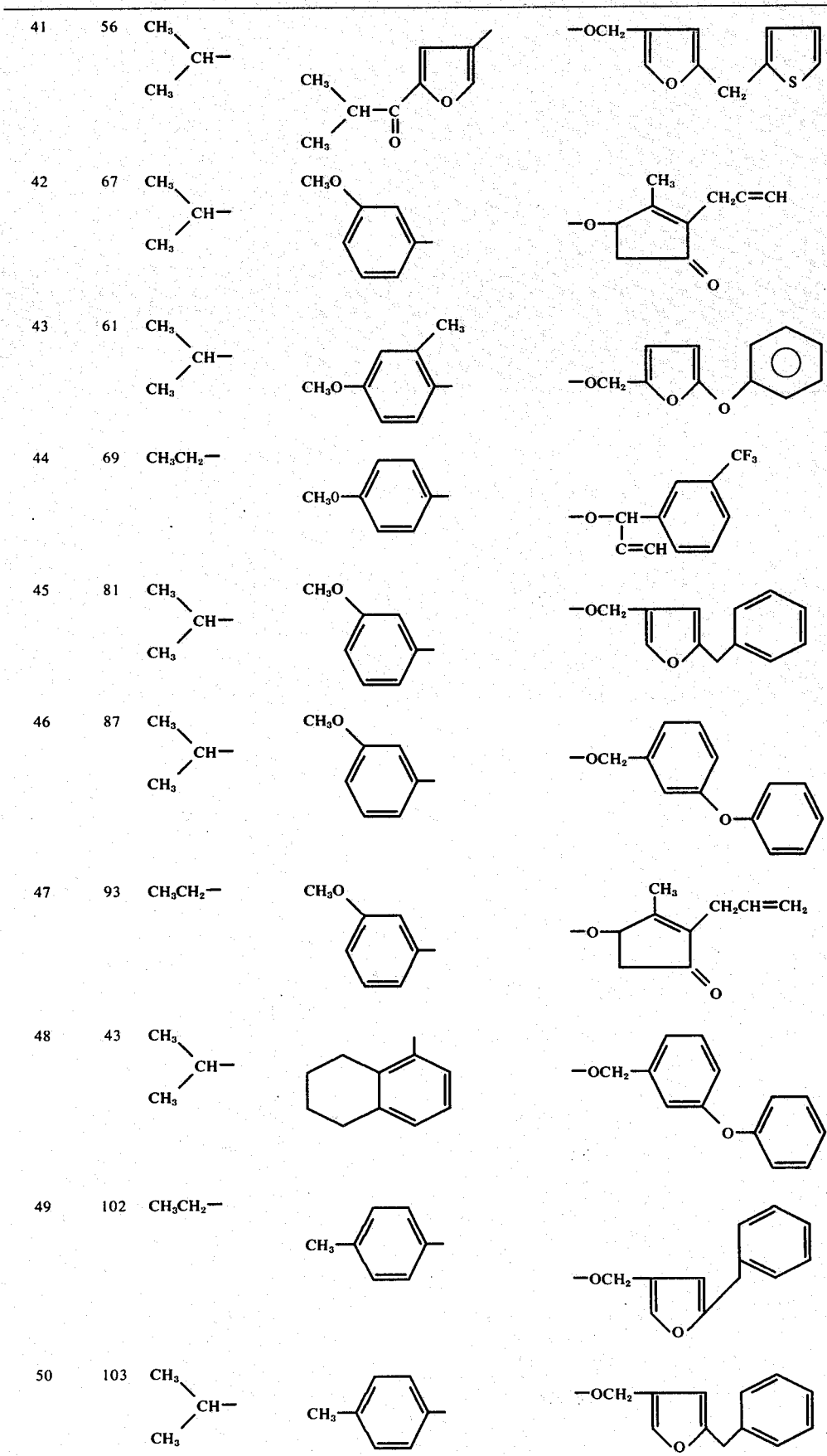

-continued

| # | No. | R1 | Ar | R2 |
|---|---|---|---|---|
| 51 | 104 | CH₃CH₂— | 3-CH₃-C₆H₄— | —OCH₂-(5-benzyl-3-furyl) |
| 52 | 105 | (CH₃)₂CH— | 3-CH₃-C₆H₄— | —OCH₂-(5-benzyl-3-furyl) |
| 53 | 106 | (CH₃)₂CH— | 3,4-(CH₃)₂-C₆H₃— | —OCH₂-(5-benzyl-3-furyl) |
| 54 | 107 | (CH₃)₂CH— | 4-Cl-C₆H₄— | —OCH₂-(5-benzyl-3-furyl) |
| 55 | 108 | (CH₃)₂CH— | 4-CH₃-C₆H₄— | —OCH₂-(3-phenoxyphenyl) |
| 56 | 109 | (CH₃)₂CH— | 2-CH₃-C₆H₄— | —OCH₂-(5-benzyl-3-furyl) |
| 57 | 110 | CH₃CH₂— | 2-CH₃-C₆H₄— | —OCH₂-(5-benzyl-3-furyl) |
| 58 | 129 | (CH₃)₂CH— | 4-Cl-C₆H₄— | —OCH₂-(3,5-dimethyl-4-vinylphenyl) |
| 59 | 130 | (CH₃)₂CH— | 4-Cl-C₆H₄— | —OCH₂-phthalimido |
| 60 | 131 | (CH₃)₂CH— | 4-Br-C₆H₄— | —OCH₂-phthalimido |

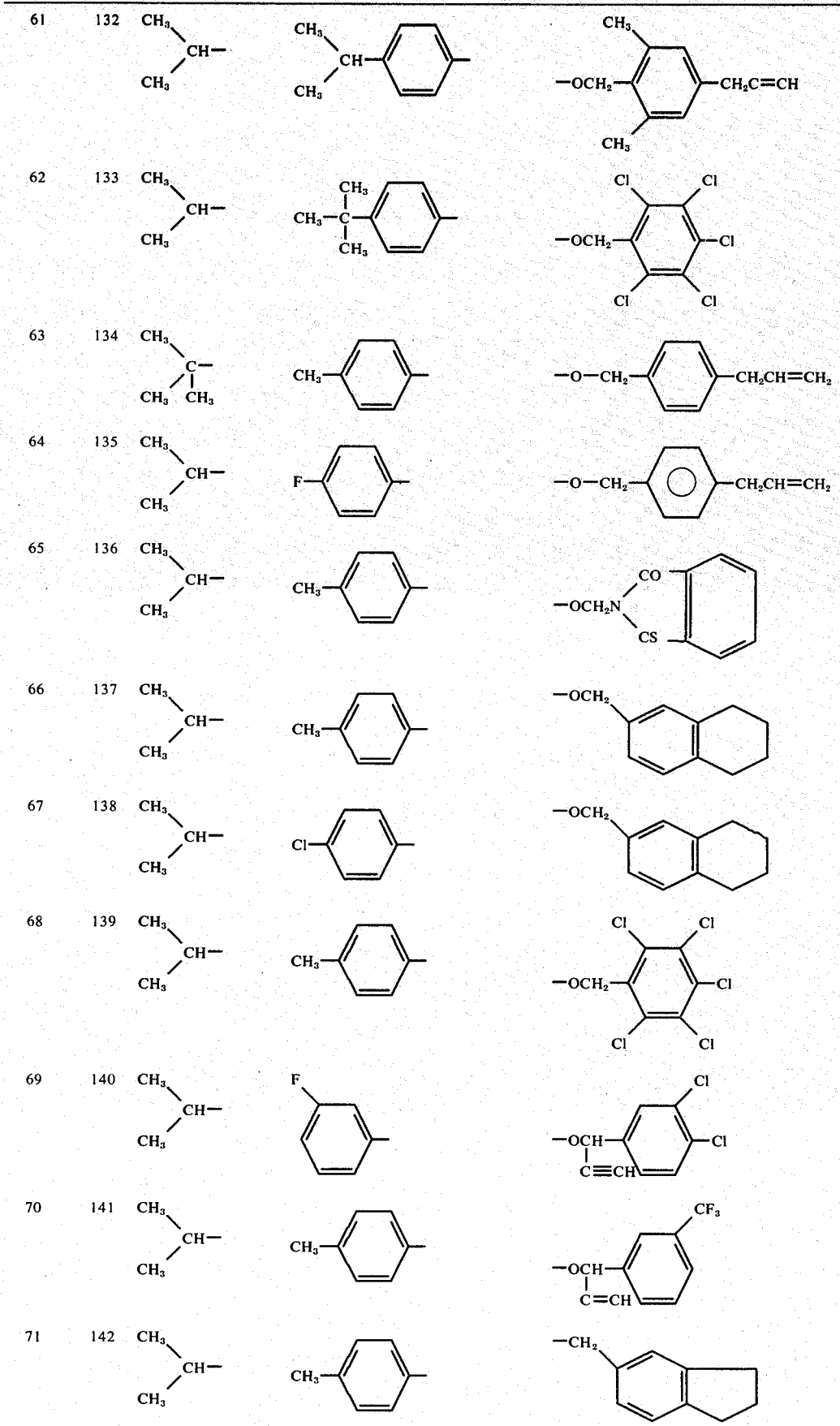

| | | | | |
|--|--|--|--|--|
| 72 | 143 | (CH₃)₂CH— | 4-(isopropyl)phenyl | —CH₂—C₆H₄—CH=CH₂ (p) |
| 73 | 144 | (CH₃)₂CH— | 4-Cl-C₆H₄— | —CH₂—C₆H₄—CH=CH₂ (p) |
| 74 | 145 | (CH₃)₂CH— | 4-CH₃-C₆H₄— | —OCH₂-(2-thienyl)-CH₂-(2-furyl) (5-) |
| 75 | 146 | (CH₃)₂CH— | 4-CH₃-C₆H₄— | —OCH₂-(5-methyl-2-furyl)-CH=CH (at 5) |
| 76 | 147 | (CH₃)₂CH— | 3-Cl-C₆H₄— | —OCH₂N(COCH₃)₂ |
| 77 | 148 | (CH₃)₂CH— | 4-CH₃-C₆H₄— | —OCH₂·CCl=CH·CH₂·C₆H₅ |
| 78 | 149 | (CH₃)₂CH— | 4-Cl-C₆H₄— | —OCH₂-(2,6-dimethyl-4-allyl)phenyl |
| 79 | 150 | (CH₃)₂CH— | 4-CH₃-C₆H₄— | —OCH₂-(4,5,6,7-tetrahydrobenzo[b]thien-2-yl) |
| 80 | 151 | (CH₃)₂CH— | 4-Cl-C₆H₄— | —OCH₂-C₆H₄-CH₂-C≡CH (p) |
| 81 | 152 | (CH₃)₂CH— | 4-F-C₆H₄— | —OCH₂-N(CO-)₂ (tetrahydrophthalimido) |
| 82 | 153 | (CH₃)₂CH— | 4-CH₃-C₆H₄— | —O-(3-methyl-2-allyl-4-oxocyclopent-2-en-1-yl) |
| 83 | 154 | (CH₃)₂CH— | 4-F-C₆H₄— | —O-(3-methyl-2-propargyl-4-oxocyclopent-2-en-1-yl) |

| | | | | |
|---|---|---|---|---|
| 84 | 155 | (CH₃)₂CH— | 4-CH₃-C₆H₄— | 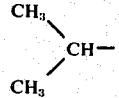 |
| 85 | 156 | (CH₃)₂CH— | 4-Cl-C₆H₄— | 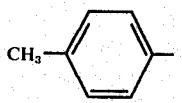 |
| 86 | 157 | (CH₃)₂CH— | 4-I-C₆H₄— | —OCH₂-(2-furyl)-5-CH₂-C₆H₅ |
| 87 | 158 | (CH₃)₂CH— | 4-CH₃-C₆H₄— | —OCH₂-(2-thienyl)-5-CH₂-C₆H₅ |
| 88 | 159 | (CH₃)₂CH— | 4-iPr-C₆H₄— | —OCH₂-(2-thienyl)-5-CH₂-C₆H₅ |
| 89 | 160 | (CH₃)₂CH— | 4-CH₃-C₆H₄— | —OCH(C≡CH)-(2-furyl)-5-CH₂C≡CH |
| 90 | 161 | (CH₃)₂CH— | 4-C₂H₅-C₆H₄— | —OCH(C≡CH)-(2-furyl)-5-CH₂C≡CH |
| 91 | 162 | (CH₃)₂CH— | 4-CH₃-C₆H₄— | —OCH₂-C₆H₄-4-CH₂CH=CH₂ |
| 92 | 163 | (CH₃)₂CH— | 4-tBu-C₆H₄— | —OCH₂-C₆H₄-3-O-(2-thienyl) |
| 93 | 164 | (CH₃)₂CH— | 4-F-C₆H₄— | —OCH₂-C₆H₄-3-O-(3-thienyl) |
| 94 | 165 | (CH₃)₂CH— | 4-F-C₆H₄— | —OCH(CN)-C₆H₄-3-O-C₆H₅ |
| 95 | 166 | (CH₃)₂CH— | 4-Br-C₆H₄— | —OCH₂-C₆H₄-3-O-(2-thienyl) |

-continued
| | | | | |
|---|---|---|---|---|
| 96 | 167 | 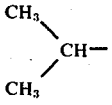 | 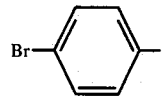 | 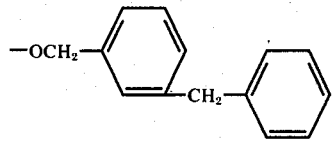 |
| 97 | 168 | 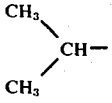 | 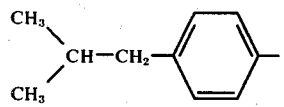 | 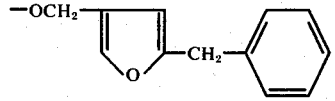 |
| 98 | 169 | $C_2H_5-$ | 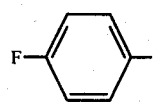 | 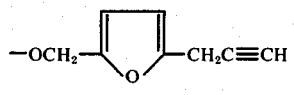 |
| 99 | 170 | $C_2H_5-$ | 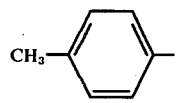 | 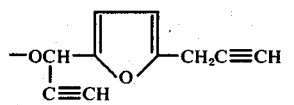 |
| 100 | 171 | $C_2H_5-$ | 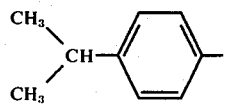 | 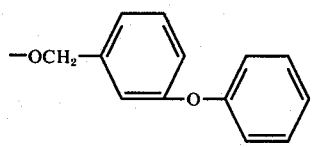 |
| 101 | 172 | $C_2H_5-$ | 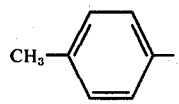 | 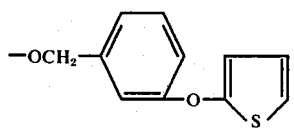 |
| 102 | 173 | $C_2H_5-$ | 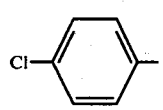 | 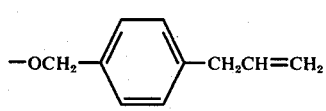 |
| 103 | 174 | $C_2H_5-$ | 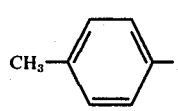 | 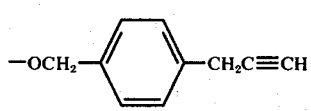 |
| 104 | 175 | $C_2H_5-$ | 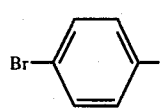 | 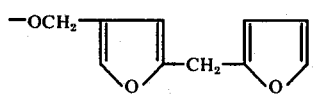 |
| 105 | 176 | $C_2H_5-$ | 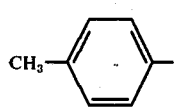 |  |
| 106 | 177 | $C_2H_5-$ |  |  |
| 107 | 178 | $C_2H_5-$ |  | 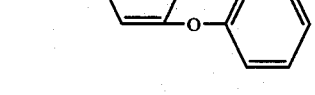 |

| | | | | |
|---|---|---|---|---|
| 108 | 179 | C₂H₅— |  | 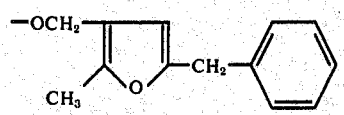 |
| 109 | 180 | C₂H₅— | 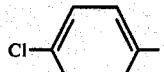 | 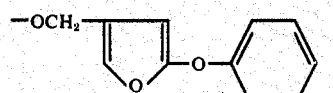 |
| 110 | 181 | CH₃— | 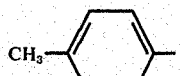 | 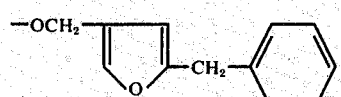 |
| 111 | 182 | CH₃— | 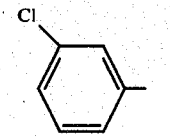 | 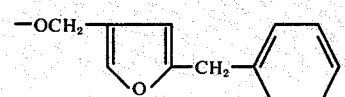 |
| 112 | 183 | CH₃— | 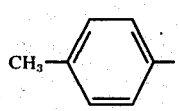 | 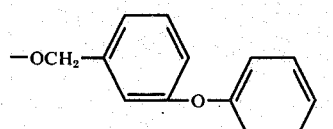 |
| 113 | 184 | C₂H₅— |  | 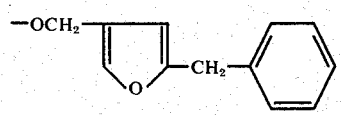 |
| 114 | 185 | C₂H₅— | 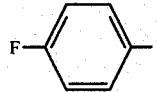 | 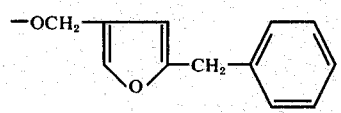 |
| 115 | 186 | C₂H₅— | 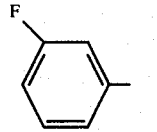 | 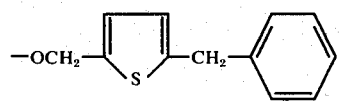 |
| 116 | 187 | C₂H₅— | 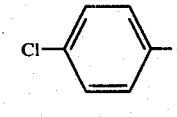 | 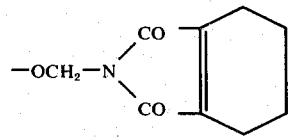 |
| 117 | 188 | C₂H₅— | 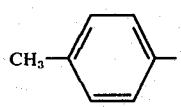 | 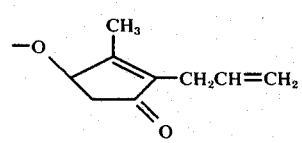 |
| 118 | 189 | C₂H₅— | 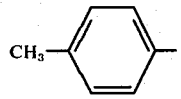 | 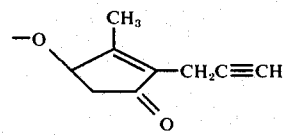 |
| 119 | 190 | C₂H₅— | 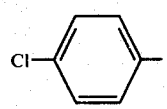 | 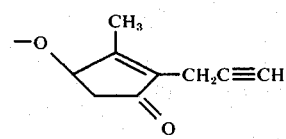 |

| | | | | |
|---|---|---|---|---|
| 120 | 191 | C₂H₅— | 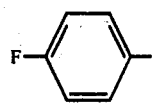 | 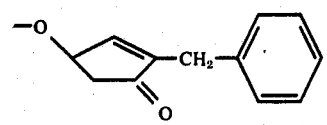 |
| 121 | 192 | C₂H₅— | 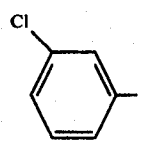 | 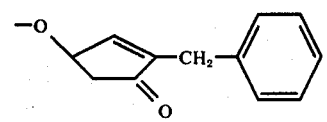 |
| 122 | 193 | 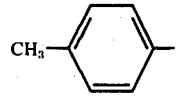 | 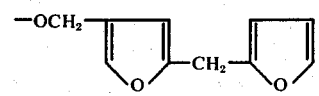 | |
| 123 | 194 | 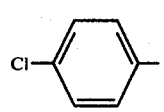 | 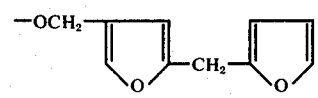 | |
| 124 | 195 | 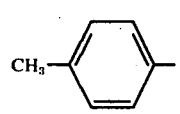 | 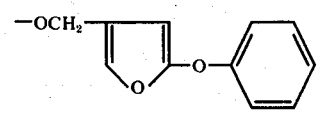 | |
| 125 | 196 | 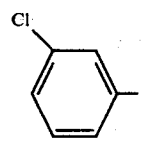 | 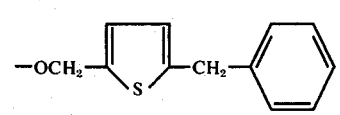 | |
| 126 | 197 | 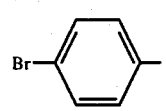 | 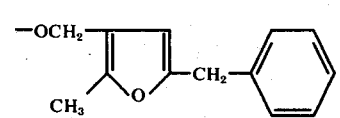 | |
| 127 | 198 | 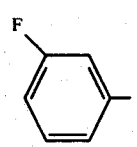 | 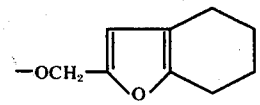 | |
| 128 | 199 | 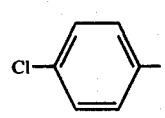 | 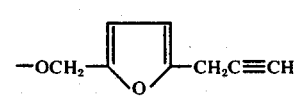 | |
| 129 | 200 | 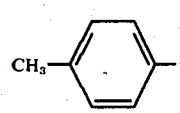 | 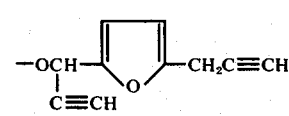 | |
| 130 | 201 | 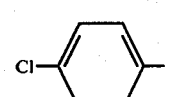 | 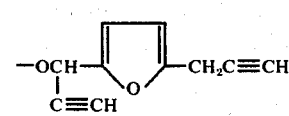 | |
| 131 | 202 | 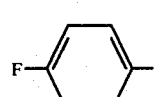 | 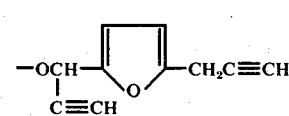 | |
| 132 | 203 | 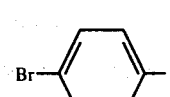 | 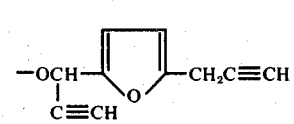 | |

-continued
| | | | | |
|---|---|---|---|---|
| 133 | 204 | 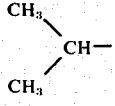 | 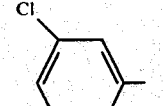 | 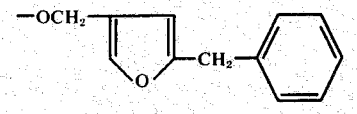 |
| 134 | 205 | 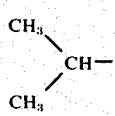 | 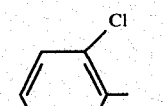 | 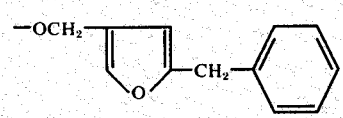 |
| 135 | 206 | 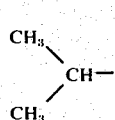 | 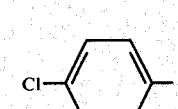 |  |
| 136 | 207 | 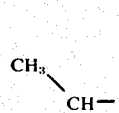 | 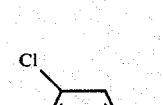 |  |
| 137 | 208 | 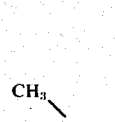 | 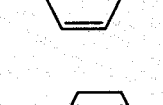 |  |
| 138 | 209 | 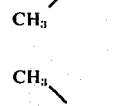 | 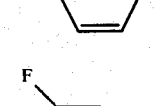 | 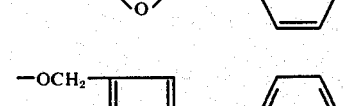 |
| 139 | 210 | 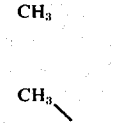 |  |  |
| 140 | 211 | 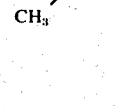 | 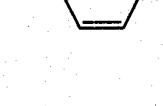 | 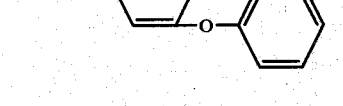 |
| 141 | 212 | 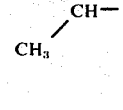 | 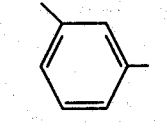 | 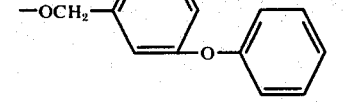 |
| 142 | 213 | 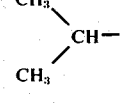 | 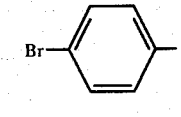 | 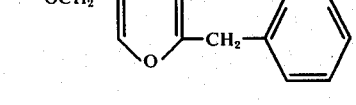 |
| 143 | 214 | 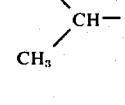 | 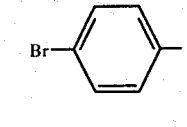 | 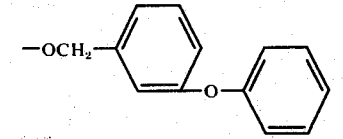 |

-continued
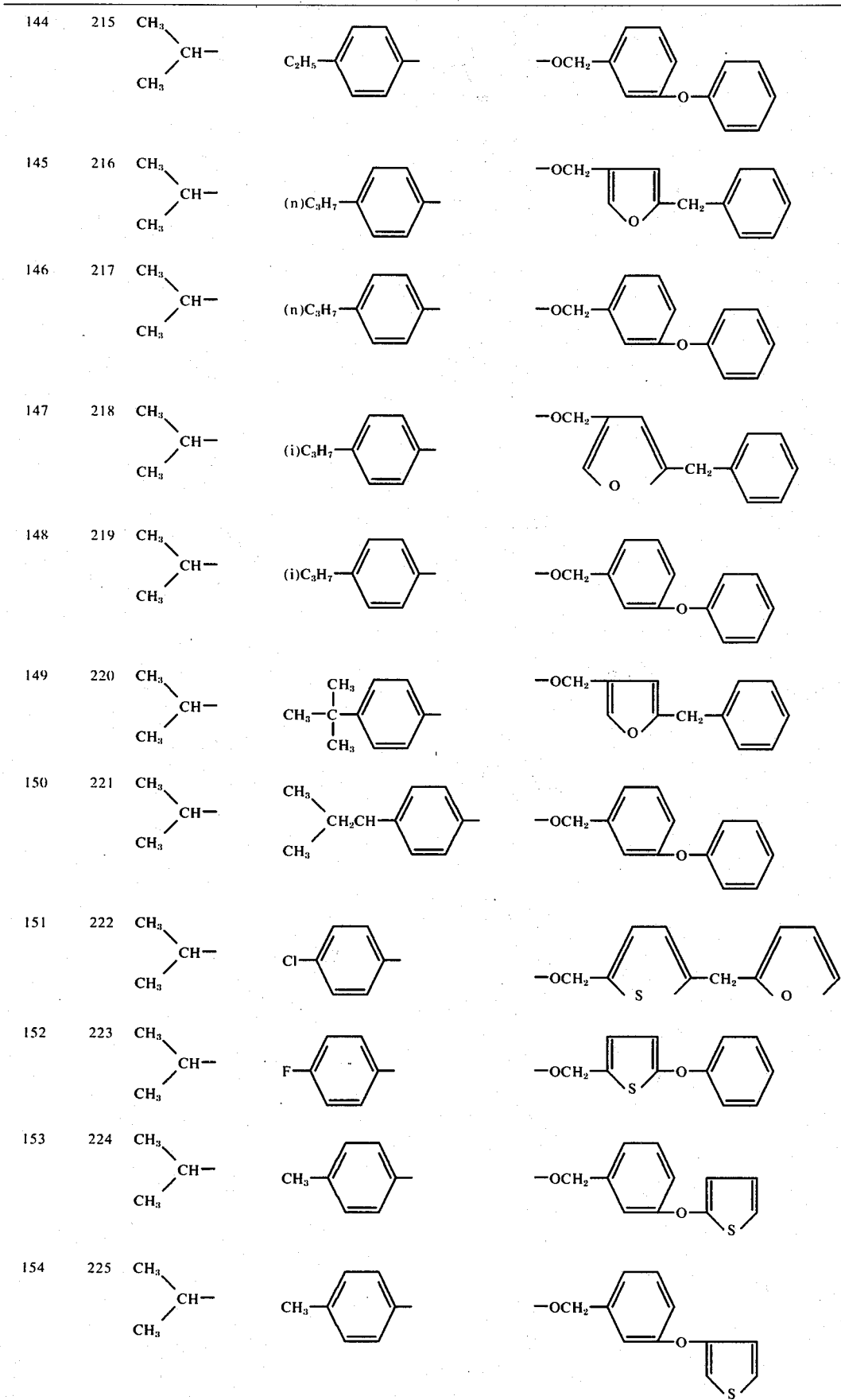

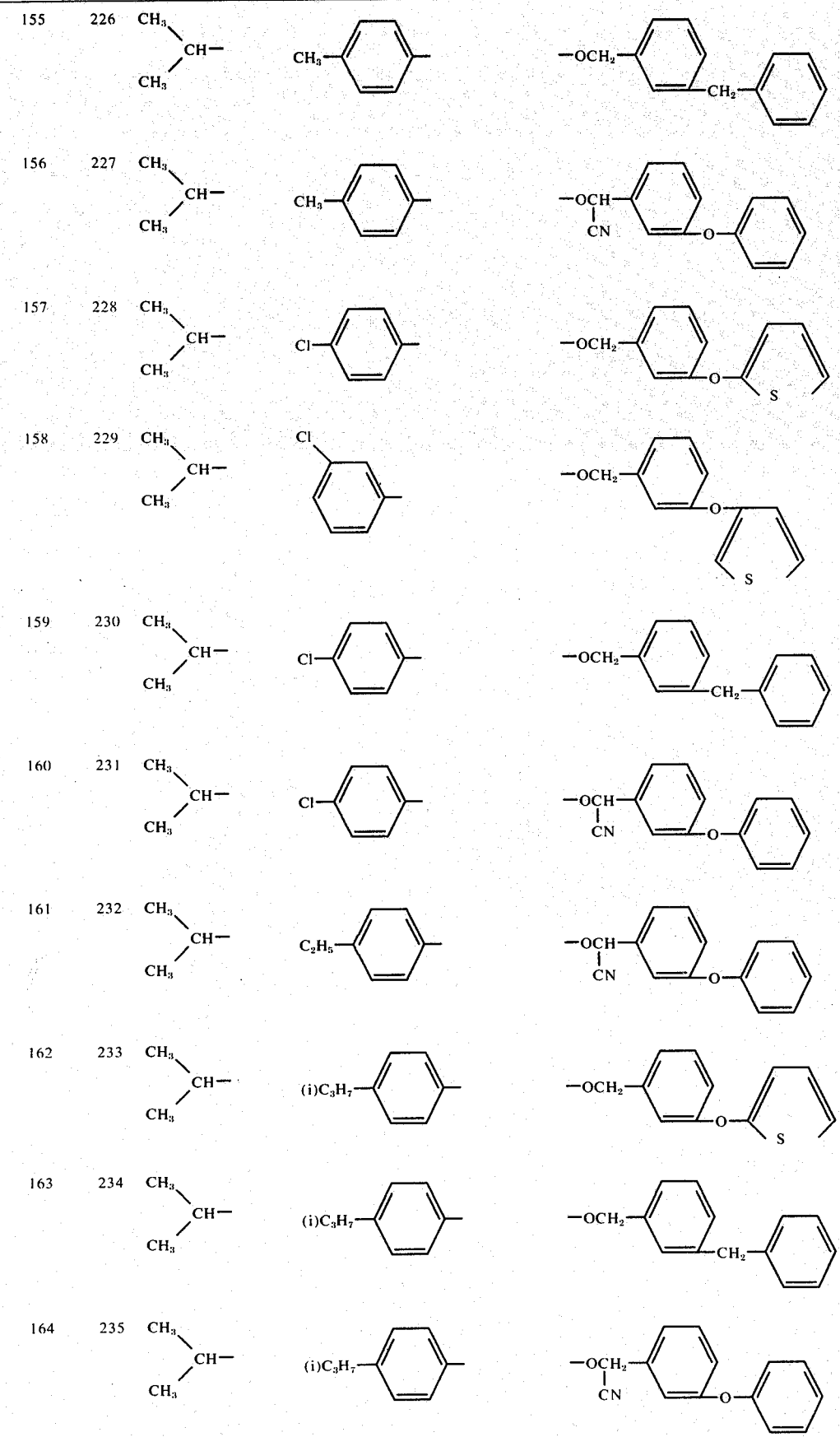

-continued
| | | | | |
|---|---|---|---|---|
| 165 | 236 | 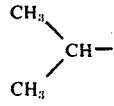 | 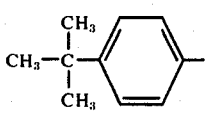 | 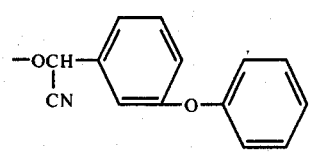 |
| 166 | 237 | 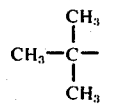 | 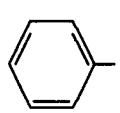 | 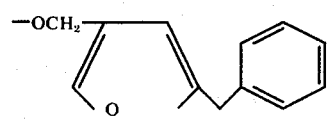 |
| 167 | 238 | 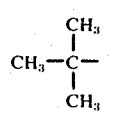 | 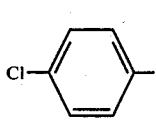 | 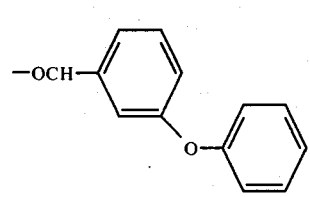 |
| 168 | 239 | 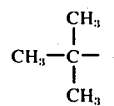 | 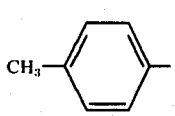 |  |
| 169 | 240 | 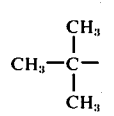 | 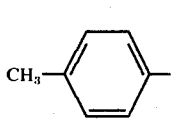 | 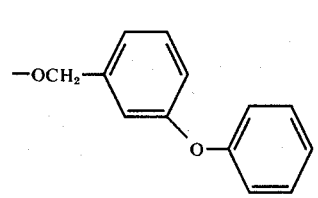 |
| 170 | 241 | 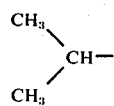 | 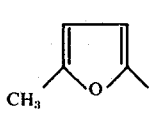 |  |
| 171 | 242 | 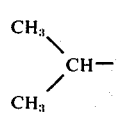 | 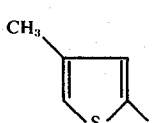 | 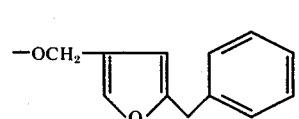 |
| 172 | 243 | 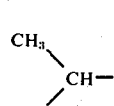 | 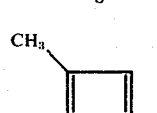 | 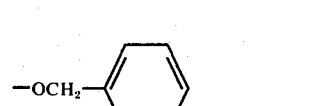 |
| 173 | 244 |  | 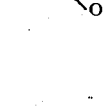 | 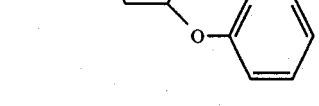 |
| 174 | 245 | CH$_3$— |  | 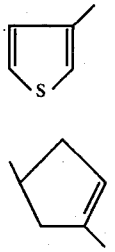 |
| 175 | 246 | C$_2$H$_5$ | 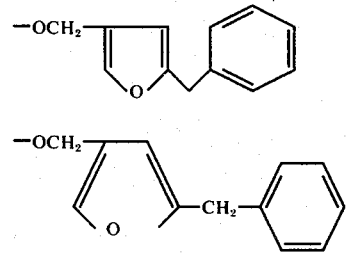 |  |

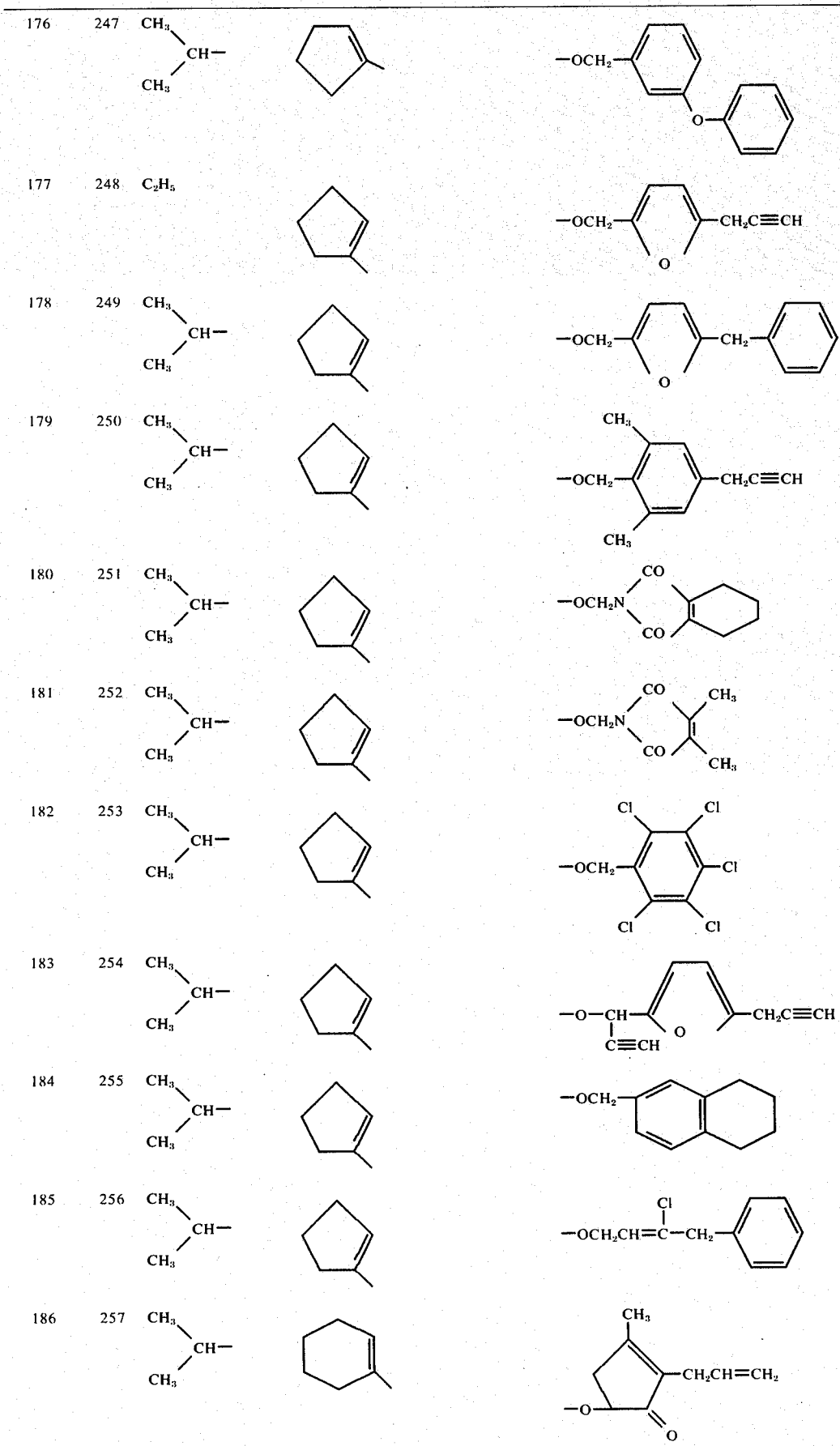

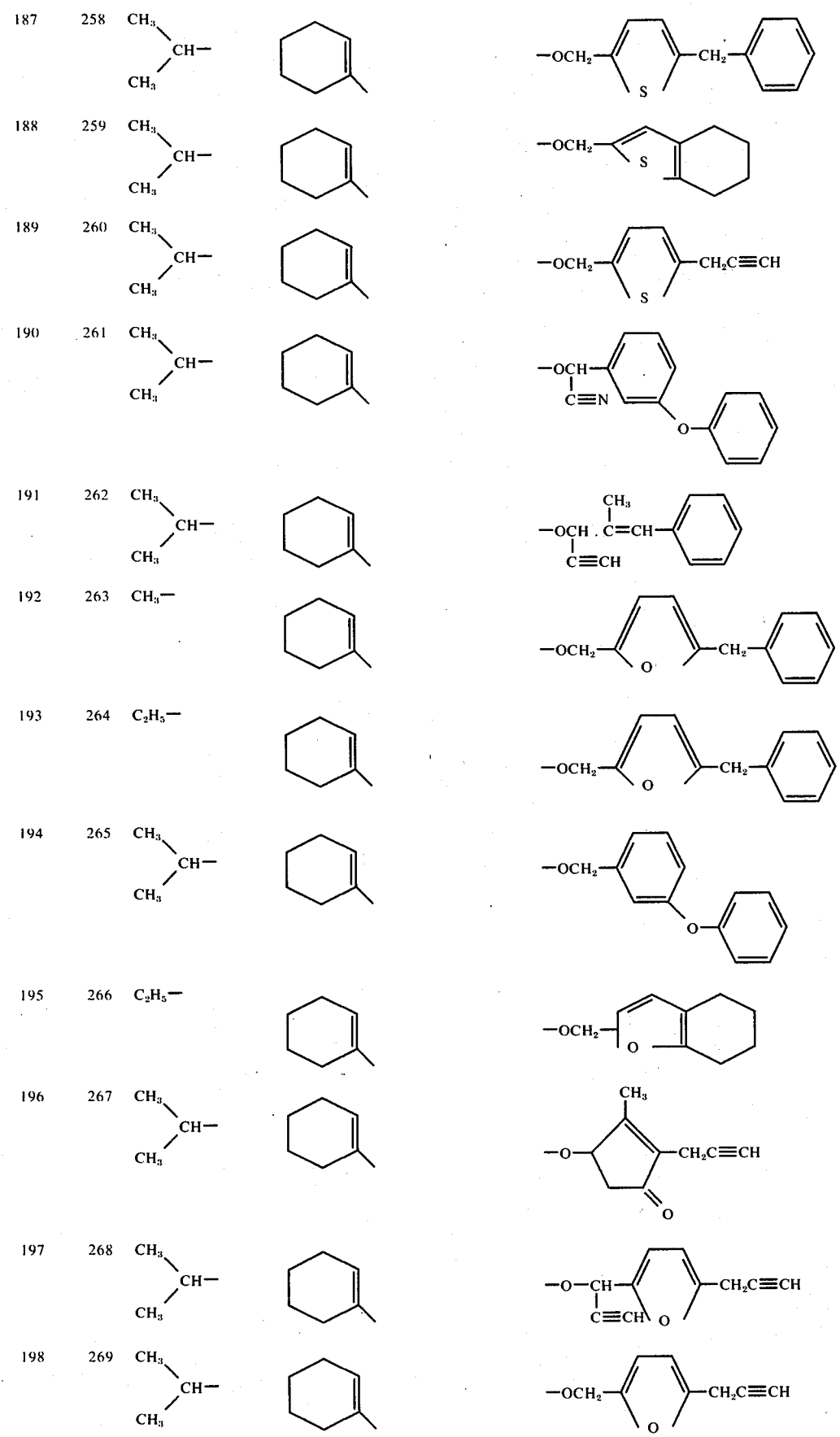

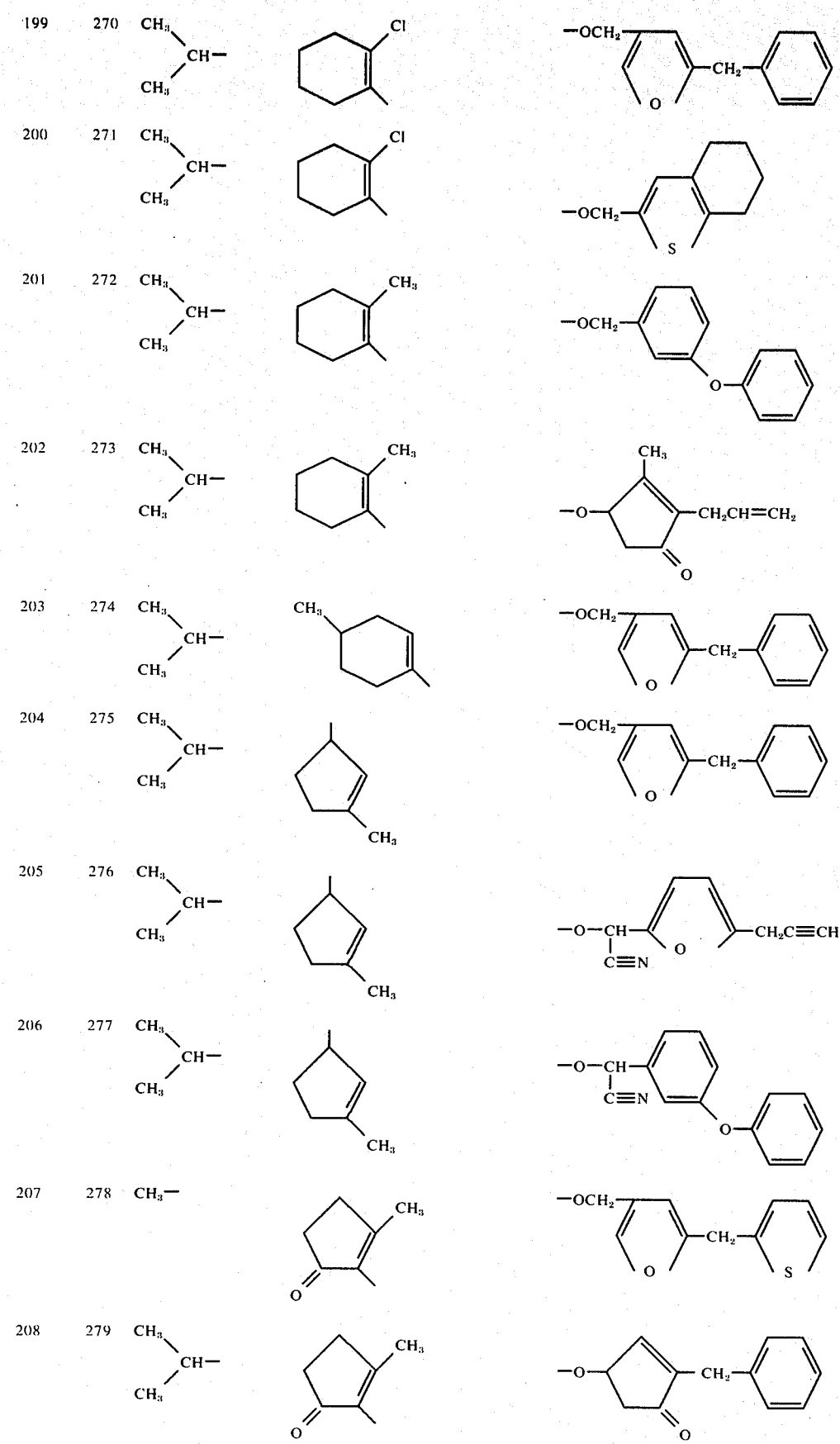

| | | | | |
|---|---|---|---|---|
| 209 | 280 | 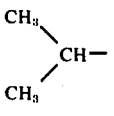 | 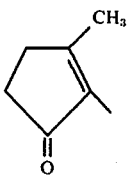 | 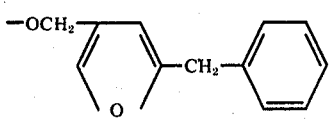 |
| 210 | 281 | C₂H₅— | 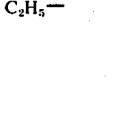 | 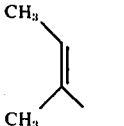 |
| 211 | 282 | 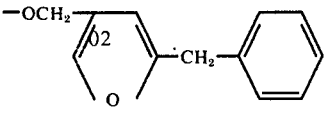 | 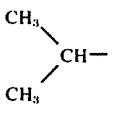 | 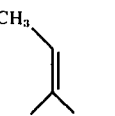 |
| 212 | 283 | 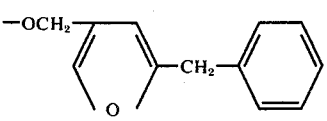 | 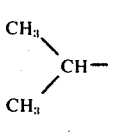 | 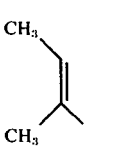 |
| 213 | 284 | 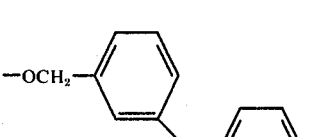 | 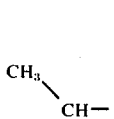 | 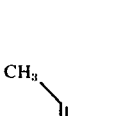 |
| 214 | 285 |  | 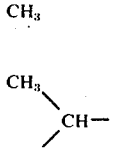 | 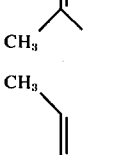 |
| 215 | 286 | CH₃— | 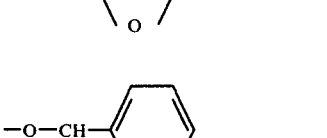 | 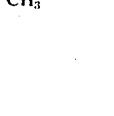 |
| 216 | 287 | C₂H₅— | 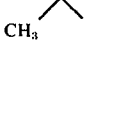 | 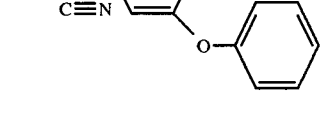 |
| 217 | 288 |  | 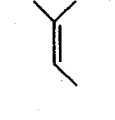 | 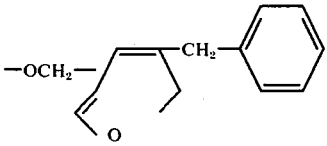 |
| 218 | 289 | C₂H₅— | 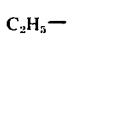 | 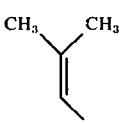 |
| 219 | 290 | 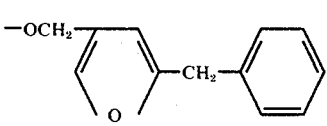 | 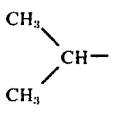 | 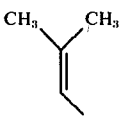 |

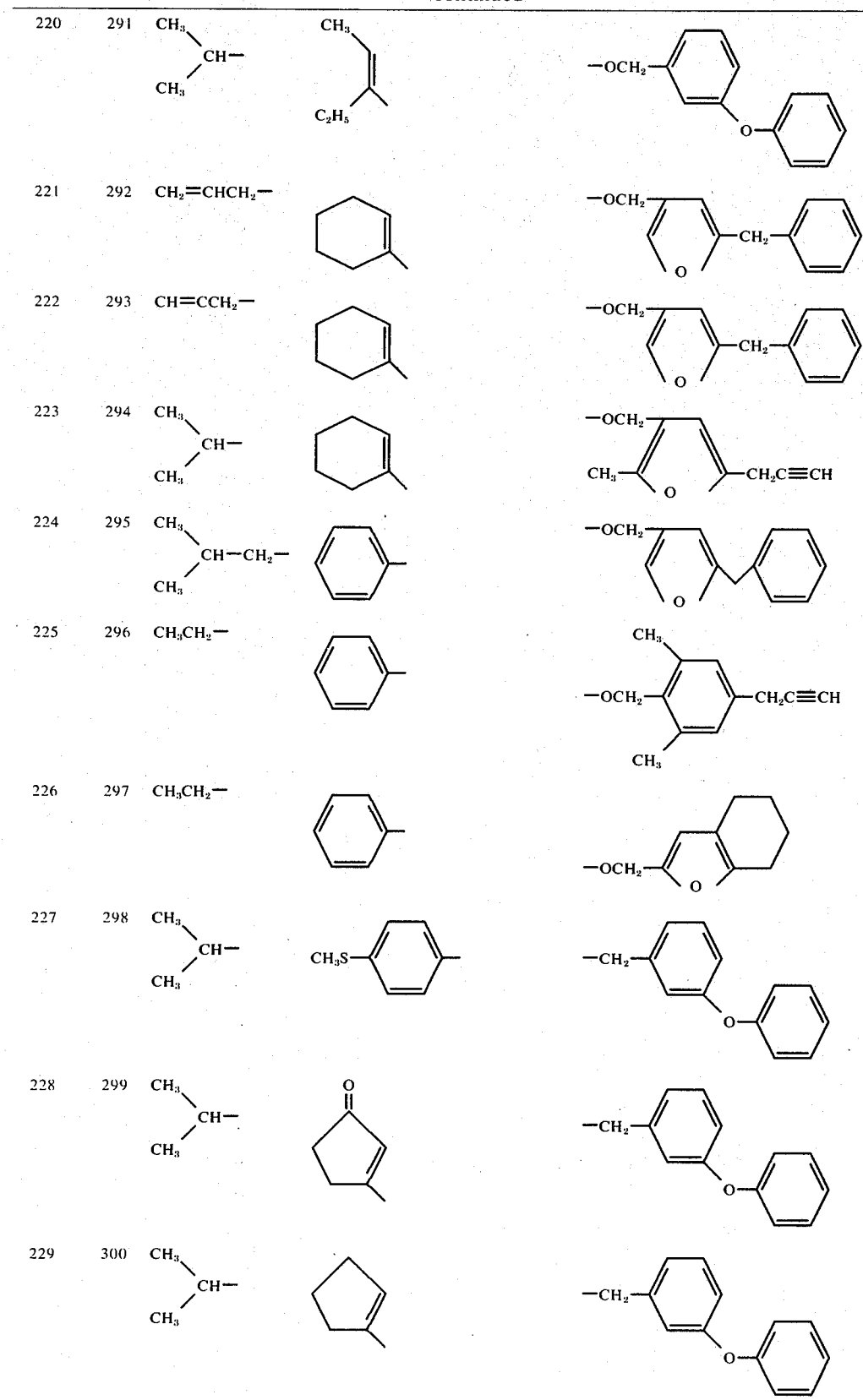
| Preparation Exp.No. | Comp No. | Esterification Method | Yield (%) | Physical Properties Calcd.(%) | Found (%) |
|---|---|---|---|---|---|
| 1 | 1 | b | 85 | $C_{22}H_{22}O_3$<br>C: 79.01 | $n_D^{17}$ 1.5545<br>78.91 |

-continued

| | | | | | |
|---|---|---|---|---|---|
| | | | | H: 6.63 | 6.54 |
| | | | | $C_{23}H_{22}O_3$ | $n_D^{22}$ 1.5712 |
| 2 | 2 | a | 91 | C: 79.74 | 79.65 |
| | | | | H: 6.40 | 6.41 |
| | | | | $C_{23}H_{22}O_4$ | $n_D^{24}$ 1.5275 |
| 3 | 3 | e | 80 | C: 76.22 | 76.19 |
| | | | | H: 6.12 | 6.17 |
| | | | | $C_{19}H_{17}O_4N$ | $n_D^{22}$ 1.5403 |
| 4 | 4 | a | 92 | C: 70.57 | 70.61 |
| | | | | H: 5.30 | 5.28 |
| | | | | N: 4.33 | 4.25 |
| | | | | $C_{19}H_{19}O_4N$ | $n_D^{22}$ 1.5349 |
| 5 | 5 | e | 75 | C: 68.99 | 67.01 |
| | | | | H: 6.11 | 6.09 |
| | | | | N: 4.47 | 4.42 |
| | | | | $C_{16}H_{16}O_3S$ | $n_D^{22}$ 1.5835 |
| 6 | 6 | a | 81 | C: 66.64 | 66.59 |
| | | | | H: 5.59 | 5.50 |
| | | | | S: 11.12 | 11.18 |
| | | | | $C_{18}H_{23}O_4N$ | $n_D^{23}$ 1.5648 |
| 7 | 7 | e | 85 | C: 68.12 | 68.09 |
| | | | | H: 7.31 | 7.22 |
| | | | | N: 4.41 | 4.50 |
| | | | | $C_{20}H_{18}O_3$ | $n_D^{24.5}$ 1.5310 |
| 8 | 8 | a | 83 | C: 78.41 | 78.3 |
| | | | | H: 5.92 | 5.86 |
| | | | | $C_{22}H_{24}O_4$ | $n_D^{22}$ 1.5123 |
| 9 | 9 | a | 84 | C: 74.97 | 75.06 |
| | | | | H: 6.86 | 6.80 |
| | | | | $C_{20}H_{20}O_2$ | $n_D^{23}$ 1.5039 |
| 10 | 10 | a | 90 | C: 82.15 | 82.05 |
| | | | | H: 6.89 | 6.93 |
| | | | | $C_{20}H_{22}O_2$ | $n_D^{24}$ 1.5536 |
| 11 | 11 | a | 93 | C: 81.60 | 81.52 |
| | | | | H: 7.53 | 7.58 |
| | | | | $C_{22}H_{22}O_2S$ | $n_D^{22}$ 1.5488 |
| 12 | 12 | a | 91 | C: 75.39 | 75.29 |
| | | | | H: 6.32 | 6.27 |
| | | | | S: 9.15 | 9.20 |
| | | | | $C_{23}H_{24}O_2S$ | $n_D^{22}$ 1.5613 |
| 13 | 13 | a | 90 | C: 75.78 | 75.70 |
| | | | | H: 6.64 | 6.69 |
| | | | | S: 8.79 | 8.81 |
| | | | | $C_{24}H_{21}O_3N$ | $n_D^{21}$ 1.5638 |
| 14 | 14 | a | 71 | C: 77.60 | 77.49 |
| | | | | H: 5.70 | 5.97 |
| | | | | N: 3.77 | 3.79 |
| | | | | $C_{22}H_{21}O_3Br$ | $n_D^{23}$ 1.5911 |
| 15 | 15 | a | 89 | C: 64.08 | 64.11 |
| | | | | H: 5.13 | 5.11 |
| | | | | Br: 19.38 | 19.29 |
| | | | | $C_{17}H_{20}O_3$ | $n_D^{22}$ 1.5118 |
| 16 | 16 | a | 90 | C: 70.81 | 70.89 |
| | | | | H: 6.99 | 6.77 |
| | | | | $C_{26}H_{28}O_3$ | mp 51–53° C |
| 17 | 17 | d | 72 | C: 80.38 | 80.41 |
| | | | | H: 7.27 | 7.24 |
| | | | | $C_{21}H_{26}O_3$ | $n_D^{23}$ 1.5417 |
| 18 | 18 | a | 84 | C: 77.27 | 77.41 |
| | | | | H: 8.03 | 7.96 |
| | | | | $C_{21}H_{22}O_3$ | $n_D^{24}$ 1.5632 |
| 19 | 19 | a | 80 | C: 78.23 | 78.19 |
| | | | | H: 6.68 | 6.94 |
| | | | | $C_{17}H_{16}O_3S$ | $n_D^{22}$ 1.5274 |
| 20 | 20 | a | 90 | C: 67.98 | 68.07 |
| | | | | H: 5.37 | 5.36 |
| | | | | S: 10.68 | 10.64 |
| | | | | $C_{20}H_{24}O_3$ | $n_D^{21}$ 1.5693 |
| 21 | 21 | a | 88 | C: 76.89 | 76.80 |
| | | | | H: 7.74 | 7.71 |
| | | | | $C_{24}H_{26}O_4$ | $n_D^{17}$ 1.5470 |
| 22 | 22 | a | 88 | C: 76.16 | 76.20 |
| | | | | H: 6.93 | 6.89 |
| | | | | $C_{23}H_{24}O_4$ | $n_D^{25}$ 1.5481 |
| 23 | 23 | b | 83.2 | C: 75.80 | 75.71 |
| | | | | H: 6.64 | 6.69 |
| | | | | $C_{26}H_{28}O_5$ | $n_D^{25}$ 1.5655 |
| 24 | 24 | c | 79.8 | C: 74.26 | 74.25 |
| | | | | H: 6.71 | 6.77 |
| | | | | $C_{25}H_{24}O_5$ | $n_D^{25}$ 1.5621 |
| 25 | 25 | e | 81.5 | C: 74.24 | 74.11 |
| | | | | H: 5.98 | 6.09 |
| | | | | $C_{22}H_{24}O_4S$ | $n_D^{25}$ 1.5448 |
| 26 | 26 | a | 90.1 | C: 69.67 | 69.55 |
| | | | | H: 6.10 | 6.11 |
| | | | | S: 8.09 | 8.11 |
| | | | | $C_{22}H_{27}O_4N$ | $n_D^{25}$ 1.5399 |
| 27 | 27 | c | 61.2 | C: 71.52 | 71.60 |
| | | | | H: 7.37 | 7.29 |
| | | | | N: 3.79 | 3.85 |
| | | | | $CH_{21}O_3F_3$ | $n_D^{25}$ 1.5368 |
| 28 | 28 | a | 92.2 | C: 66.66 | 66.61 |
| | | | | H: 5.59 | 5.62 |

-continued

| | | | | | | |
|---|---|---|---|---|---|---|
| | | | | | F: 15.06 | 15.11 |
| 29 | 30 | a | 82.5 | $C_{22}H_{24}O_4$<br>C: 74.97<br>H: 6.86 | $n_D^{25}$ 1.5566<br>75.02<br>6.04 | |
| 30 | 33 | c | 81.8 | $C_{24}H_{24}O_6$<br>C: 70.57<br>H: 5.92 | $n_D^{25}$ 1.5367<br>70.56<br>5.89 | |
| 31 | 34 | a | 92.5 | $C_{27}H_{27}O_4N$<br>C: 75.50<br>H: 6.34<br>N: 3.26 | $n_D^{25}$ 1.5208<br>75.19<br>6.30<br>3.31 | |
| 32 | 35 | a | 95.3 | $C_{24}H_{26}O_3S$<br>C: 73.06<br>H: 6.64<br>S: 8.13 | $n_D^{25}$ 1.5335<br>73.10<br>6.64<br>8.15 | |
| 33 | 37 | a | 73.6 | $C_{22}H_{20}O_5$<br>C: 72.51<br>H: 5.53 | $n_D^{25}$ 1.5236<br>72.55<br>5.61 | |
| 34 | 36 | d | 86.2 | $C_{27}H_{30}O_3$<br>C: 80.56<br>H: 7.51 | 80.61<br>7.46 | |
| 35 | 45 | c | 78.1 | $C_{26}H_{24}O_3$<br>C: 81.22<br>H: 6.29 | 81.20<br>6.31 | |
| 36 | 48 | a | 92.7 | $C_{23}H_{25}O_5N$<br>C: 69.85<br>H: 6.37<br>N: 3.54 | $n_D^{25}$ 1.5221<br>69.78<br>6.39<br>3.55 | |
| 37 | 49 | a | 91.2 | $C_{25}H_{29}O_2Cl$<br>C: 75.64<br>H: 7.36<br>Cl: 8.93 | $n_D^{25}$ 1.5413<br>75.66<br>7.39<br>8.87 | |
| 38 | 51 | a | 84.6 | $C_{22}H_{22}O_4$<br>C: 75.41<br>H: 6.33 | $n_D^{26}$ 1.5253<br>75.40<br>6.22 | |
| 39 | 52 | a | 81.2 | $C_{22}H_{24}O_3S$<br>C: 71.71<br>H: 6.56<br>S: 8.70 | $n_D^{25}$ 1.5549<br>71.80<br>6.59<br>8.78 | |
| 40 | 55 | a | 86.9 | $C_{22}H_{21}O_5NS$<br>C: 64.21<br>H: 5.15<br>N: 3.40<br>S: 7.79 | $n_D^{19}$ 1.5350<br>64.30<br>5.19<br>3.29<br>7.72 | |
| 41 | 56 | c | 72.1 | $C_{23}H_{26}O_5S$<br>C: 66.64<br>H: 6.32<br>S: 7.14 | $n_D^{22}$ 1.5324<br>66.57<br>6.40<br>7.71 | |
| 42 | 67 | a | 93.7 | $C_{21}H_{24}O_4$<br>C: 74.09<br>H: 7.11 | $n_D^{25}$ 1.5628<br>74.06<br>7.22 | |
| 43 | 61 | a | 93.2 | $C_{24}H_{26}O_5$<br>C: 73.07<br>H: 6.64 | $n_D^{25}$ 1.5501<br>73.11<br>6.57 | |
| 44 | 69 | b | 78.9 | $C_{21}H_{19}O_3F_3$<br>C: 67.01<br>H: 5.09<br>F: 15.15 | $n_D^{25}$ 1.5119<br>66.95<br>5.14<br>15.20 | |
| 45 | 81 | d | 84.8 | $C_{24}H_{26}O_4$<br>C: 76.16<br>H: 6.93 | $n_D^{16}$ 1.5411<br>76.22<br>6.94 | |
| 46 | 87 | d | 86.4 | $C_{25}H_{26}O_4$<br>C: 76.90<br>H: 6.71 | $n_D^{17}$ 1.5377<br>76.85<br>6.76 | |
| 47 | 93 | b | 83.1 | $C_{26}H_{24}O_4$<br>C: 73.14<br>H: 7.37 | $n_D^{19}$ 1.5211<br>73.19<br>7.30 | |
| 48 | 43 | e | 83.2 | $C_{28}H_{30}O_3$<br>C: 81.12<br>H: 7.30 | $n_D^{20}$ 1.5660<br>81.20<br>7.27 | |
| 49 | 102 | a | 91 | $C_{23}H_{24}O_3$<br>C: 79.28<br>H: 6.94 | $n_D^{25}$ 1.5474<br>79.32<br>7.10 | |
| 50 | 103 | a | 90 | $C_{24}H_{26}O_3$<br>C: 79.53<br>H: 7.23 | $n_D^{25}$ 1.5433<br>79.60<br>7.18 | |
| 51 | 104 | a | 89 | $C_{23}H_{24}O_3$<br>C: 79.28<br>H: 6.94 | $n_D^{25}$ 1.5470<br>79.23<br>6.99 | |
| 52 | 105 | a | 93 | $C_{24}H_{26}O_3$<br>C: 79.53<br>H: 7.23 | $n_D^{25.5}$ 1.5430<br>79.50<br>7.30 | |
| 53 | 106 | a | 92 | $C_{25}H_{28}O_3$<br>C: 79.75<br>H: 7.50 | $n_D^{25.5}$ 1.5238<br>79.79<br>7.49 | |
| 54 | 107 | a | 91 | $C_{23}H_{23}O_3Cl$<br>C: 72.15<br>H: 6.05<br>Cl: 9.26 | $n_D^{25.5}$ 1.5241<br>72.18<br>6.10<br>9.29 | |
| 55 | 108 | a | 90 | $C_{25}H_{26}O_3$<br>C: 80.18<br>H: 7.00<br>$C_{24}H_{26}O_3$ | $n_D^{28.5}$ 1.5596<br>80.21<br>6.92<br>$n_D^{26.5}$ 1.5431 | |

-continued

| | | | | | |
|---|---|---|---|---|---|
| 56 | 109 | a | 94 | C: 77.53 | 79.60 |
| | | | | H: 7.23 | 7.21 |
| | | | | $C_{23}H_{24}O_3$ | $n_D^{26.5}$ 1.5501 |
| 57 | 110 | a | 89 | C: 79.28 | 79.40 |
| | | | | H: 6.94 | 7.11 |
| | | | | $C_{23}H_{25}O_2Cl$ | $n_D^{20}$ 1.5423 |
| 58 | 129 | b | 85 | C: 74.88 | 74.79 |
| | | | | H: 6.83 | 6.81 |
| | | | | Cl 9.61 | 9.63 |
| | | | | $C_{20}H_{18}O_4NCl$ | $n_D^{20}$ 1.5501 |
| 59 | 103 | c | 68 | C: 64.60 | 64.63 |
| | | | | H: 4.88 | 4.86 |
| | | | | N: 3.77 | 3.79 |
| | | | | Cl: 9.54 | 9.53 |
| | | | | $C_{20}H_{18}O_4NBr$ | $n_D^{20}$ 1.5383 |
| 60 | 131 | c | 69 | C: 57.70 | 57.80 |
| | | | | H: 4.36 | 4.39 |
| | | | | N: 3.37 | 3.37 |
| | | | | Br: 19.20 | 19.28 |
| | | | | $C_{26}H_{32}O_2$ | $n_D^{20}$ 1.5433 |
| 61 | 132 | a | 88 | C: 82.93 | 82.88 |
| | | | | H: 8.57 | 8.63 |
| | | | | $C_{22}H_{23}O_2Cl_5$ | $n_D^{20}$ 1.5211 |
| 62 | 133 | a | 92 | C: 53.20 | 53.58 |
| | | | | H: 4.67 | 4.68 |
| | | | | Cl: 35.69 | 35.71 |
| | | | | $C_{23}H_{28}O_2$ | |
| 63 | 134 | a | 93 | C: 82.10 | 82.19 |
| | | | | H: 8.39 | 8.41 |
| | | | | $C_{21}H_{23}O_2F$ | |
| 64 | 135 | a | 89 | C: 77.27 | 77.32 |
| | | | | H: 7.10 | 7.03 |
| | | | | F: 5.82 | 5.91 |
| | | | | $C_{21}H_{21}O_3NS$ | $n_D^{20}$ 1.5335 |
| 65 | 136 | a | 89 | C: 68.64 | 68.67 |
| | | | | H: 5.76 | 5.81 |
| | | | | N: 3.81 | 3.80 |
| | | | | S: 8.73 | 8.79 |
| | | | | $C_{23}H_{28}O_2$ | $n_D^{20}$ 1.5299 |
| 66 | 137 | d | 81 | C: 82.10 | 82.15 |
| | | | | H: 8.39 | 8.30 |
| | | | | $C_{22}H_{25}O_2Cl$ | $n_D^{20}$ 1.5414 |
| 67 | 138 | d | 87 | C: 74.04 | 74.08 |
| | | | | H: 7.06 | 7.10 |
| | | | | Cl: 9.94 | 10.03 |
| | | | | $C_{19}H_{17}O_2Cl_5$ | $n_D^{20}$ 1.5382 |
| 68 | 139 | b | 79 | C: 50.19 | 50.22 |
| | | | | H: 3.77 | 3.79 |
| | | | | Cl: 39.01 | 39.13 |
| | | | | $C_{20}H_{17}O_2FCl_2$ | $n_D^{20}$ 1.5288 |
| 69 | 140 | a | 69 | C: 63.34 | 63.39 |
| | | | | H: 4.52 | 4.46 |
| | | | | F: 5.01 | 5.08 |
| | | | | Cl: 18.70 | 18.80 |
| | | | | $C_{22}H_{20}O_2F_3$ | $n_D^{20}$ 1.5385 |
| 70 | 141 | a | 78 | C: 70.76 | 70.80 |
| | | | | H: 5.40 | 5.39 |
| | | | | F: 15.27 | 15.27 |
| | | | | $C_{22}H_{26}O_2$ | $n_D^{20}$ 1.5236 |
| 71 | 142 | a | 82 | C: 81.95 | 82.06 |
| | | | | H: 8.13 | 8.12 |
| | | | | $C_{24}H_{30}O_2$ | $n_D^{20}$ 1.5341 |
| 72 | 143 | a | 80 | C: 82.24 | 82.19 |
| | | | | H: 8.63 | 8.66 |
| | | | | $C_{21}H_{23}O_2Cl$ | $n_D^{20}$ 1.5491 |
| 73 | 144 | a | 83 | C: 73.56 | 73.51 |
| | | | | H: 6.76 | 6.81 |
| | | | | Cl: 10.34 | 10.29 |
| | | | | $C_{22}H_{24}O_3S$ | $n_D^{20}$ 1.5372 |
| 74 | 145 | b | 86 | C: 71.71 | 71.73 |
| | | | | H: 6.56 | 6.60 |
| | | | | S: 8.70 | 8.79 |
| | | | | $C_{21}H_{24}O_3$ | $n_D^{20}$ 1.5377 |
| 75 | 146 | a | 92 | C: 77.75 | 77.77 |
| | | | | H: 7.46 | 7.40 |
| | | | | $C_{18}H_{20}O_4NCl$ | $n_D^{20}$ 1.5469 |
| 76 | 147 | a | 95 | C: 61.80 | 61.90 |
| | | | | H: 5.76 | 5.73 |
| | | | | N: 4.01 | 4.02 |
| | | | | Cl: 10.14 | 10.19 |
| | | | | $C_{22}H_{25}O_2Cl$ | $n_D^{20}$ 1.5471 |
| 77 | 148 | b | 87 | C: 74.04 | 74.11 |
| | | | | H: 7.06 | 7.92 |
| | | | | Cl: 9.94 | 9.90 |
| | | | | $C_{23}H_{26}O_2Cl$ | $n_D^{20}$ 1.5483 |
| 78 | 149 | a | 84 | C: 74.68 | 74.77 |
| | | | | H: 7.09 | 7.12 |
| | | | | Cl: 9.59 | 9.52 |
| | | | | $C_{21}H_{26}O_2S$ | $n_D^{20}$ 1.5396 |
| 79 | 150 | a | 89 | C: 73.64 | 73.66 |
| | | | | H: 7.65 | 7.64 |
| | | | | S: 9.36 | 9.50 |
| | | | | $C_{21}H_{21}O_2Cl$ | $n_D^{20}$ 1.5611 |

| # | Cmpd | Method | Yield % | Formula / Calc. | Found / $n_D$ |
|---|---|---|---|---|---|
| 80 | 151 | a | 95 | $C_{20}H_{22}O_4NF$ C: 74.00 H: 6.21 Cl: 10.40 | $n_D^{20}$ 1.5229 74.11 6.23 10.36 |
| 81 | 152 | e | 82 | C: 66.84 H: 6.17 N: 3.90 F: 5.29 | 66.88 6.18 4.01 5.30 |
| 82 | 153 | b | 80 | $C_{21}H_{26}O_3$ C: 77.27 H: 8.03 | $n_D^{20}$ 1.5387 77.20 8.09 |
| 83 | 154 | a | 89 | $C_{20}H_{21}O_3F$ C: 73.15 H: 6.45 F: 5.79 | $n_D^{20}$ 1.5316 73.19 6.50 5.81 |
| 84 | 155 | a | 93 | $C_{24}H_{26}O_3$ C: 79.53 H: 7.23 | $n_D^{20}$ 1.5452 79.55 7.33 |
| 85 | 156 | a | 92 | $C_{23}H_{23}O_3Cl$ C: 72.15 H: 6.05 Cl: 9.26 | $n_D^{20}$ 1.5448 72.18 6.00 9.32 |
| 86 | 157 | a | 92 | $C_{23}H_{23}O_3I$ C: 58.24 H: 4.89 I: 26.76 | $n_D^{20}$ 1.5352 58.22 4.93 26.88 |
| 87 | 158 | a | 96 | $C_{24}H_{26}O_2S$ C: 76.15 H: 6.92 S: 8.47 | $n_D^{19}$ 1.5311 76.16 7.03 8.46 |
| 88 | 159 | a | 86 | $C_{26}H_{30}O_2S$ C: 76.80 H: 7.44 S: 7.89 | $n_D^{19}$ 1.5342 76.77 7.51 7.82 |
| 89 | 160 | a | 81 | $C_{22}H_{22}O_3$ C: 79.01 H: 6.63 | $n_D^{26}$ 1.5262 79.22 6.58 |
| 90 | 161 | a | 76 | $C_{23}H_{24}O_3$ C: 79.28 H: 6.94 | $n_D^{22}$ 1.5291 79.33 7.10 |
| 91 | 162 | a | 92 | $C_{22}H_{26}O_2$ C: 81.95 H: 8.13 | $n_D^{20}$ 1.5366 82.00 8.18 |
| 92 | 163 | a | 87 | $C_{26}H_{30}O_3S$ C: 73.90 H: 7.16 S: 7.59 | $n_D^{20}$ 1.5361 73.92 7.17 7.63 |
| 93 | 164 | a | 88 | $C_{22}H_{21}O_3SF$ C: 68.73 H: 5.51 S: 4.94 F: 4.94 | $n_D^{20}$ 1.4837 68.77 5.48 8.36 4.90 |
| 94 | 165 | a | 88 | $C_{25}H_{22}O_3NF$ C: 74.42 H: 5.50 N: 3.47 F: 4.71 | $n_D^{20}$ 1.5233 74.49 5.56 — 4.79 |
| 95 | 166 | a | 92 | $C_{22}H_{21}O_3SBr$ C: 59.33 H: 4.75 S 7.20 Br: 17.94 | $n_D^{20}$ 1.5811 59.36 4.79 7.11 17.92 |
| 96 | 167 | d | 91 | $C_{25}H_{23}O_2Br$ C: 68.97 H: 5.32 Br: 18.36 | $n_D^{20}$ 1.5802 68.96 5.33 18.40 |
| 97 | 168 | a | 93 | $C_{27}H_{32}O_3$ C: 80.16 H: 7.97 | $n_D^{20}$ 1.5387 80.15 7.96 |
| 98 | 169 | a | 79 | $C_{18}H_{17}O_3F$ C: 71.98 H: 5.71 F: 6.33 | $n_D^{20}$ 1.5218 71.99 5.76 6.33 |
| 99 | 170 | b | 82 | $C_{21}H_{20}O_3$ C: 78.72 H: 6.29 | $n_D^{26}$ 1.5261 78.77 6.22 |
| 100 | 171 | e | 89 | $C_{26}H_{28}O_3$ C: 80.38 H: 7.27 | $n_D^{19}$ 1.5536 80.29 7.33 |
| 101 | 172 | e | 82 | $C_{22}H_{22}O_3S$ C: 72.10 H: 6.05 S: 8.75 | $n_D^{19}$ 1.5499 72.16 6.07 8.82 |
| 102 | 173 | a | 93 | $C_{20}H_{21}O_2Cl$ C: 73.05 H: 6.44 Cl: 10.78 | $n_D^{20}$ 1.5236 73.09 6.46 10.69 |
| 103 | 174 | a | 92 | $C_{21}H_{22}O_2$ C: 82.32 H: 7.24 | $n_D^{20}$ 1.5252 82.40 7.26 |
| 104 | 175 | a | 86 | $C_{20}H_{19}O_4Br$ C: 59.56 H: 4.75 | $n_D^{20}$ 1.5233 59.61 4.77 |

-continued

| | | | | | |
|---|---|---|---|---|---|
| | | | | Br:19.82 | 20.91 |
| 105 | 176 | e | 92 | $C_{24}H_{24}O_3$ C: 79.97 H: 6.71 | $n_D^{20}$ 1.5711 80.05 6.77 |
| 106 | 177 | e | 96 | $C_{23}H_{21}O_3Cl$ C: 72.53 H: 5.56 Cl: 9.31 | $n_D^{21.5}$ 1.5732 72.51 5.46 9.33 |
| 107 | 178 | e | 89 | $C_{23}H_{21}O_3Br$ C: 64.95 H: 4.98 Br:18.79 | $n_D^{17}$ 1.5861 64.92 4.86 18.82 |
| 108 | 179 | a | 82 | $C_{23}H_{21}O_3I$ C: 58.24 H: 4.89 I: 26.76 | $n_D^{20}$ 1.5733 58.25 4.92 28.81 |
| 109 | 180 | b | 76 | $C_{21}H_{19}O_4Cl$ C: 68.01 H: 5.16 Cl: 9.56 | $n_D^{20}$ 1.5625 66.06 5.22 9.62 |
| 110 | 181 | a | 90 | $C_{22}H_{22}O_3$ C: 79.01 H: 6.63 | $n_D^{25}$ 1.5471 79.07 6.58 |
| 111 | 182 | a | 91 | $C_{21}H_{19}O_3Cl$ C: 71.08 H: 5.40 Cl: 9.99 | $n_D^{22}$ 1.5518 71.11 5.32 9.89 |
| 112 | 183 | c | 87 | $C_{23}H_{22}O_3$ C: 79.74 H: 6.40 | $n_D^{28}$ 1.5592 79.77 6.36 |
| 113 | 184 | a | 88 | $C_{22}H_{21}O_3Cl$ C: 71.63 H: 5.74 Cl: 9.61 | $n_D^{25}$ 1.5549 71.66 5.81 9.70 |
| 114 | 185 | a | 87 | $C_{22}H_{21}O_3F$ C: 74.98 H: 6.00 F: 5.39 | $n_D^{20}$ 1.4437 75.03 6.02 5.29 |
| 115 | 186 | a | 83 | $C_{22}H_{21}O_2SF$ C: 71.71 H: 5.75 H: 8.70 F: 5.16 | $n_D^{20}$ 1.4933 71.77 5.76 8.81 5.13 |
| 116 | 187 | e | 76 | $C_{19}H_{20}O_4NCl$ C: 63.07 H: 5.57 N: 3.87 Cl: 9.80 | $n_D^{20}$ 1.5316 62.98 5.54 3.92 9.69 |
| 117 | 188 | a | 83 | $C_{20}H_{24}O_3$ C: 76.89 H: 7.74 | $n_D^{20}$ 1.5224 76.79 7.81 |
| 118 | 189 | a | 80 | $C_{20}H_{22}O_3$ C: 77.39 H: 7.14 | $n_D^{20}$ 1.5456 77.44 7.14 |
| 119 | 190 | a | 82 | $C_{19}H_{19}O_3Cl$ C: 68.98 H: 5.79 Cl:10.72 | $n_D^{20}$ 1.5445 68.92 5.78 10.85 |
| 120 | 191 | a | 90 | $C_{22}H_{21}O_3F$ C: 74.98 H: 6.01 F: 5.39 | $n_D^{20}$ 1.5267 74.87 6.02 5.41 |
| 121 | 192 | a | 92 | $C_{22}H_{21}O_3Cl$ C: 71.63 H: 5.74 Cl: 9.61 | $n_D^{20}$ 1.5352 71.66 5.78 9.62 |
| 122 | 193 | a | 90 | $C_{22}H_{24}O_4$ C: 74.97 H: 6.86 | $n_D^{19}$ 1.5377 75.10 6.86 |
| 123 | 194 | a | 91 | $C_{21}H_{21}O_3Cl$ C: 67.65 H: 5.68 Cl: 9.51 | $n_D^{19}$ 1.5421 67.62 5.72 9.61 |
| 124 | 195 | a | 89 | $C_{23}H_{24}O_4$ C: 75.80 H: 6.64 | $n_D^{20}$ 1.5235 75.83 6.70 |
| 125 | 196 | a | 91 | $C_{23}H_{23}O_2SCl$ C: 69.24 H: 5.81 S: 8.04 Cl: Cl: 8.92 | $n_D^{20}$ 1.5551 69.26 5.84 8.11 |
| 126 | 197 | a | 88 | $C_{24}H_{25}O_3Br$ C: 65.31 H: 5.71 Br:18.11 | $n_D^{20}$ 1.5349 65.33 5.83 18.20 |
| 127 | 198 | a | 92 | $C_{20}H_{23}O_3F$ C: 72.70 H: 7.02 F: 5.75 | $n_D^{20}$ 1.5466 72.69 7.11 5.72 |
| 128 | 199 | a | 80 | $C_{19}H_{19}O_3Cl$ C: 68.98 H: 5.79 Cl:10.72 | $n_D^{19}$ 1.5238 69.01 5.72 10.77 |

-continued

| | | | | Formula | Analysis Calc. | Found | $n_D$ |
|---|---|---|---|---|---|---|---|
| 129 | 200 | a | 82 | $C_{22}H_{22}O_3$ | C: 79.01<br>H: 6.63 | 79.10<br>6.58 | $n_D^{20}$ 1.5265 |
| 130 | 201 | a | 79 | $C_{21}H_{19}O_3Cl$ | C: 71.08<br>H: 5.40<br>Cl: 9.99 | 71.00<br>5.46<br>9.89 | $n_D^{20}$ 1.5233 |
| 131 | 202 | a | 75 | $C_{21}H_{19}O_3F$ | C: 74.54<br>H: 5.66<br>F: 5.62 | 74.53<br>5.77<br>5.66 | $n_D^{20}$ 1.5249 |
| 132 | 203 | a | 83 | $C_{21}H_{19}O_3Br$ | C: 63.17<br>H: 4.80<br>Br: 20.02 | 63.18<br>4.79<br>20.04 | $n_D^{20}$ 1.5289 |
| 133 | 204 | a | 90 | $C_{23}H_{23}O_3Cl$ | C: 72.15<br>H: 6.05<br>Cl: 9.26 | 72.16<br>6.11<br>9.39 | $n_D^{21}$ 1.5521 |
| 134 | 205 | a | 89 | $C_{23}H_{23}O_3Cl$ | C: 72.15<br>H: 6.05<br>Cl: 9.26 | 72.14<br>6.09<br>9.31 | $n_D^{21}$ 1.5576 |
| 135 | 206 | d | 83 | $C_{24}H_{23}O_3Cl$ | C: 72.99<br>H: 5.87<br>Cl: 8.98 | 73.04<br>5.87<br>8.99 | $n_D^{21}$ 1.5655 |
| 136 | 207 | e | 92 | $C_{24}H_{23}O_3Cl$ | C: 72.99<br>H: 5.87<br>Cl: 8.98 | 72.93<br>5.89<br>9.00 | $n_D^{17}$ 1.5722 |
| 137 | 208 | d | 84 | $C_{23}H_{23}O_3F$ | C: 75.39<br>H: 6.33<br>F: 5.19 | 75.42<br>6.31<br>5.22 | $n_D^{21}$ 1.4637 |
| 138 | 209 | a | 92 | $C_{23}H_{23}O_3F$ | C: 75.39<br>H: 6.33<br>F: 5.19 | 75.44<br>6.26<br>5.14 | $n_D^{21}$ 1.5330 |
| 139 | 210 | d | 93 | $C_{24}H_{23}O_3F$ | C: 76.17<br>H: 6.13<br>F: 5.02 | 76.20<br>6.14<br>5.10 | $n_D^{23}$ 1.5544 |
| 140 | 211 | e | 92 | $C_{24}H_{23}O_3F$ | C: 76.17<br>H: 6.13<br>F: 5.02 | 76.15<br>6.13<br>5.11 | $n_D^{21.5}$ 1.5543 |
| 141 | 212 | a | 89 | $C_{23}H_{23}O_3Br$ | C: 64.64<br>H: 5.42<br>Br: 18.70 | 64.58<br>5.44<br>18.96 | $n_D^{17}$ 1.5651 |
| 142 | 213 | e | 91 | $C_{24}H_{23}O_3Br$ | C: 65.61<br>H: 5.28<br>Br: 18.19 | 65.62<br>5.30<br>18.23 | $n_D^{17.5}$ 1.5802 |
| 143 | 214 | a | 82 | $C_{25}H_{28}O_3$ | C: 79.75<br>H: 7.50 | 79.81<br>7.51 | $n_D^{18.5}$ 1.5347 |
| 144 | 215 | a | 94 | $C_{26}H_{28}O_3$ | C: 80.38<br>H: 7.27 | 80.34<br>7.29 | $n_D^{21.5}$ 1.5590 |
| 145 | 216 | a | 92 | $C_{26}H_{30}O_3$ | C: 79.96<br>H: 7.74 | 80.01<br>7.70 | $n_D^{18}$ 1.5387 |
| 146 | 217 | a | 90 | $C_{27}H_{30}O_3$ | C: 80.56<br>H: 7.51 | 80.52<br>7.52 | $n_D^{18}$ 1.5542 |
| 147 | 218 | a | 92 | $C_{26}H_{30}O_3$ | C: 79.96<br>H: 7.74 | 79.94<br>7.83 | $n_D^{22}$ 1.5385 |
| 148 | 219 | a | 93 | $C_{27}H_{30}O_3$ | C: 80.56<br>H: 7.51 | 80.58<br>7.53 | $n_D^{19}$ 1.5548 |
| 149 | 220 | a | 90 | $C_{27}H_{32}O_3$ | C: 80.16<br>H: 7.97 | 80.21<br>8.04 | $n_D^{24}$ 1.5302 |
| 150 | 221 | a | 94 | $C_{28}H_{32}O_3$ | C: 80.73<br>H: 7.74 | 80.67<br>7.71 | $n_D^{20}$ 1.5327 |
| 151 | 222 | a | 82 | $C_{21}H_{21}O_3SCl$ | C: 64.85<br>H: 5.44<br>S: 8.25<br>Cl: 9.12 | 64.88<br>5.42<br>8.26<br>9.13 | $n_D^{20}$ 1.5377 |
| 152 | 223 | a | 77 | $C_{22}H_{21}O_3SF$ | C: 68.73<br>H: 5.51<br>S: 8.34<br>F: 4.94 | 68.70<br>5.59<br>8.32<br>4.92 | $n_D^{20}$ 1.5467 |
| 153 | 224 | a | 86 | $C_{23}H_{24}O_3S$ | C: 72.60<br>H: 6.36<br>S: 8.43 | 72.54<br>6.33<br>8.50 | $n_D^{19}$ 1.5366 |

-continued

| | | | | | |
|---|---|---|---|---|---|
| 154 | 225 | a | 79 | $C_{23}H_{24}O_3S$<br>C: 72.60<br>H: 6.36<br>S: 8.43 | $n_D^{19}$ 1.5277<br>72.61<br>6.38<br>8.49 |
| 155 | 226 | a | 81 | $C_{26}H_{28}O_2$<br>C: 81.62<br>H: 10.01 | $n_D^{20}$ 1.5235<br>81.66<br>10.03 |
| 156 | 227 | a | 72 | $C_{26}H_{25}O_3N$<br>C: 78.17<br>H: 6.31<br>N: 3.51 | $n_D^{20}$ 1.5624<br>78.19<br>6.28<br>3.61 |
| 157 | 228 | a | 83 | $C_{22}H_{21}O_3SCl$<br>C: 65.90<br>H: 5.28<br>S: 8.00<br>Cl: 8.84 | $n_D^{19}$ 1.5433<br>65.99<br>5.27<br>8.04<br>8.82 |
| 158 | 229 | a | 85 | $C_{22}H_{21}O_3SCl$<br>C: 65.90<br>H: 5.28<br>S: 8.00<br>Cl: 8.84 | $n_D^{19}$ 1.5436<br>65.91<br>5.29<br>8.16<br>8.83 |
| 159 | 230 | a | 90 | $C_{25}H_{25}O_2Cl$<br>C: 76.42<br>H: 6.41<br>C: 9.02 | $n_D^{20}$ 1.5329<br>76.44<br>6.43<br>9.09 |
| 160 | 231 | a | 74 | $C_{25}H_{22}O_3NCl$<br>C: 71.51<br>H: 5.28<br>N: 3.34<br>Cl: 8.44 | $n_D^{20}$ 1.5533<br>71.54<br>5.30<br>3.31<br>8.46 |
| 161 | 232 | a | 75 | $C_{27}H_{27}O_3N$<br>C: 78.42<br>H: 6.58<br>N: 3.39 | $n_D^{20}$ 1.5239<br>78.44<br>6.61<br>3.44 |
| 162 | 233 | a | 86 | $C_{25}H_{28}O_3S$<br>C: 73.49<br>H: 6.91<br>S: 7.85 | $n_D^{20}$ 1.5567<br>73.51<br>6.94<br>7.86 |
| 163 | 234 | a | 89 | $C_{28}H_{32}O_2$<br>C: 83.96<br>H: 8.05 | $n_D^{20}$ 1.5341<br>83.99<br>8.06 |
| 164 | 235 | a | 80 | $C_{24}H_{29}O_3N$<br>C: 78.66<br>H: 6.84<br>N: 3.28 | $n_D^{20}$ 1.5226<br>78.67<br>6.90<br>3.11 |
| 165 | 236 | a | 79 | $C_{29}H_{31}O_3N$<br>C: 78.88<br>H: 7.08<br>N: 3.17 | $n_D^{20}$ 1.5451<br>78.79<br>7.06<br>3.24 |
| 166 | 237 | a | 87 | $C_{24}H_{26}O_3$<br>C: 79.53<br>H: 7.23 | $n_D^{20}$ 1.5335<br>79.56<br>7.20 |
| 167 | 238 | a | 89 | $C_{25}H_{25}O_3Cl$<br>C: 73.43<br>H: 6.16<br>Cl: 8.67 | $n_D^{19}$ 1.5427<br>73.49<br>6.20<br>8.60 |
| 168 | 239 | a | 89 | $C_{25}H_{28}O_3$<br>C: 79.75<br>H: 7.49 | $n_D^{20}$ 1.5366<br>79.72<br>7.52 |
| 169 | 240 | a | 91 | $C_{26}H_{28}O_3$<br>C: 80.38<br>H: 7.26 | $n_D^{21}$ 1.5225<br>80.33<br>7.24 |
| 170 | 241 | a | 76 | $C_{22}H_{24}O_4$<br>C: 74.98<br>H: 6.86 | $n_D^{22}$ 1.5236<br>75.02<br>6.80 |
| 171 | 242 | a | 79 | $C_{22}H_{24}O_3S$<br>C: 71.71<br>H: 6.56<br>S: 8.70 | $n_D^{20}$ 1.5475<br>71.77<br>6.52<br>8.72 |
| 172 | 243 | a | 79 | $C_{23}H_{24}O_4$<br>C: 75.80<br>H: 6.64 | $n_D^{20}$ 1.5344<br>75.76<br>6.62 |
| 173 | 244 | a | 82 | $C_{21}H_{22}O_3S$<br>C: 71.15<br>H: 6.26<br>S: 9.04 | $n_D^{19}$ 1.5226<br>71.09<br>6.22<br>9.11 |
| 174 | 245 | a | 89 | $C_{20}H_{22}O_3$<br>C: 77.37<br>H: 7.14 | $n_D^{28}$ 1.5293<br>77.29<br>7.16 |
| 175 | 246 | a | 89 | $C_{21}H_{24}O_3$<br>C: 77.75<br>H: 7.46 | $n_D^{24.5}$ 1.5276<br>77.78<br>7.44 |
| 176 | 247 | a | 86 | $C_{23}H_{26}O_3$<br>C: 78.83<br>H: 7.48 | $n_D^{28}$ 1.5483<br>78.81<br>7.40 |
| 177 | 248 | a | 90 | $C_{18}H_{22}O_3$<br>C: 75.49<br>H: 7.74 | $n_D^{24.5}$ 1.4965<br>75.53<br>7.69 |
| 178 | 249 | a | 90 | $C_{22}H_{26}O_3$<br>C: 78.07<br>H: 7.74 | $n_D^{24.5}$ 1.5248<br>78.10<br>7.74 |
| 179 | 250 | a | 85 | $C_{22}H_{28}O_2$<br>C: 81.44 | $n_D^{28}$ 1.5615<br>81.64 |

-continued

| | | | | | |
|---|---|---|---|---|---|
| | | | | H: 8.70 | 8.53 |
| | | | | $C_{19}H_{25}O_4N$ | $n_D^{25}$ 1.5380 |
| 180 | 251 | a | 91 | C: 68.86 | 68.69 |
| | | | | H: 7.60 | 7.64 |
| | | | | N: 4.23 | 4.10 |
| | | | | $C_{17}H_{23}O_4N$ | $n_D^{25}$ 1.5237 |
| 181 | 252 | a | 88 | C: 66.86 | 66.97 |
| | | | | H: 7.59 | 7.50 |
| | | | | N: 4.59 | 4.45 |
| | | | | $C_{17}H_{17}O_2Cl_5$ | $n_D^{28}$ 1.5395 |
| 182 | 253 | a | 90 | C: 47.42 | 47.88 |
| | | | | H: 3.98 | 3.70 |
| | | | | Cl: 41.17 | 41.53 |
| | | | | $C_{20}H_{22}O_3$ | $n_D^{24.5}$ 1.5088 |
| 183 | 254 | a | 85 | C: 77.37 | 77.35 |
| | | | | H: 7.14 | 7.17 |
| | | | | $C_{21}H_{28}O_2$ | $n_D^{25}$ 1.5132 |
| 184 | 255 | a | 90 | C: 80.73 | 80.70 |
| | | | | N: 9.03 | 8.98 |
| | | | | $C_{20}H_{25}O_2Cl$ | $n_D^{25}$ 1.5205 |
| 185 | 256 | a | 89 | C: 72.16 | 72.05 |
| | | | | H: 7.59 | 7.55 |
| | | | | Cl: 10.65 | 10.92 |
| | | | | $C_{20}H_{28}O_3$ | $n_D^{24.5}$ 1.5085 |
| 186 | 257 | a | 86 | C: 75.91 | 75.86 |
| | | | | H: 8.92 | 8.90 |
| | | | | $C_{23}H_{28}O_2S$ | $n_D^{23}$ 1.5370 |
| 187 | 258 | a | 90 | C: 74.96 | 74.78 |
| | | | | H: 7.66 | 7.62 |
| | | | | S: 8.70 | 8.58 |
| | | | | $C_{19}H_{26}O_2S$ | $n_D^{23}$ 1.5352 |
| 188 | 259 | a | 89 | C: 71.66 | 71.69 |
| | | | | H: 8.23 | 8.24 |
| | | | | S: 10.07 | 9.80 |
| | | | | $C_{19}H_{24}O_2S$ | $n_D^{23}$ 1.5323 |
| 189 | 260 | a | 92 | C: 72.11 | 72.15 |
| | | | | H: 7.64 | 7.68 |
| | | | | S: 10.13 | 10.05 |
| | | | | $C_{25}H_{27}O_3N$ | $n_D^{28}$ 1.5486 |
| 190 | 261 | a | 85 | C: 77.09 | 76.93 |
| | | | | H: 6.99 | 6.92 |
| | | | | N: 3.60 | 3.52 |
| | | | | $C_{23}H_{28}O_2$ | $n_D^{28}$ 1.5213 |
| 191 | 262 | a | 86 | C: 82.10 | 82.15 |
| | | | | H: 8.39 | 8.39 |
| | | | | $C_{21}H_{24}O_3$ | $n_D^{28}$ 1.5309 |
| 192 | 263 | a | 86 | C: 77.75 | 77.60 |
| | | | | H: 7.46 | 7.48 |
| | | | | $C_{22}H_{26}O_3$ | $n_D^{24}$ 1.5308 |
| 193 | 264 | a | 88 | C: 78.07 | 78.12 |
| | | | | H: 7.74 | 7.61 |
| | | | | $C_{24}H_{28}O_3$ | $n_D^{24}$ 1.5467 |
| 194 | 265 | a | 86 | C: 79.09 | 78.80 |
| | | | | H: 7.74 | 7.76 |
| | | | | $C_{19}H_{26}O_3$ | $n_D^{28}$ 1.5088 |
| 195 | 266 | a | 86 | C: 75.46 | 75.40 |
| | | | | H: 8.67 | 8.66 |
| | | | | $C_{20}H_{26}O_3$ | $n_D^{24.5}$ 1.5140 |
| 196 | 267 | a | 90 | C: 76.40 | 76.58 |
| | | | | H: 8.34 | 8.29 |
| | | | | $C_{21}H_{24}O_3$ | $n_D^{24.5}$ 1.5133 |
| 197 | 268 | a | 85 | C: 77.75 | 77.81 |
| | | | | H: 7.46 | 7.40 |
| | | | | $C_{19}H_{24}O_3$ | $n_D^{24.5}$ 1.5064 |
| 198 | 269 | a | 87 | C: 75.97 | 75.86 |
| | | | | H: 8.05 | 8.04 |
| | | | | $C_{22}H_{25}O_3Cl$ | $n_D^{24.5}$ 1.5358 |
| 199 | 270 | a | 92 | C: 70.86 | 70.66 |
| | | | | H: 6.76 | 6.73 |
| | | | | Cl: 9.51 | 9.30 |
| | | | | $C_{19}H_{25}O_2ClS$ | $n_D^{23}$ 1.5430 |
| | | | | C: 64.66 | 64.74 |
| 200 | 271 | a | 88 | H: 7.14 | 7.15 |
| | | | | Cl: 10.05 | 9.77 |
| | | | | S: 9.09 | 9.13 |
| | | | | $C_{25}H_{30}O_3$ | $n_D^{23}$ 1.5474 |
| 201 | 272 | a | 90 | C: 79.33 | 79.25 |
| | | | | H: 7.99 | 7.90 |
| | | | | $C_{21}H_{30}O_3$ | $n_D^{28}$ 1.5030 |
| 202 | 273 | a | 87 | C: 76.32 | 76.55 |
| | | | | H: 9.15 | 9.13 |
| | | | | $C_{25}H_{30}O_3$ | $n_D^{28}$ 1.5243 |
| 203 | 274 | a | 87 | C: 79.33 | 79.47 |
| | | | | H: 7.99 | 7.95 |
| | | | | $C_{24}H_{28}O_3$ | $n_D^{24}$ 1.5252 |
| 204 | 275 | a | 89 | C: 79.09 | 79.05 |
| | | | | H: 7.74 | 7.73 |
| | | | | $C_{21}H_{24}O_3$ | $n_D^{24}$ 1.5097 |
| 205 | 276 | a | 86 | C: 77.75 | 77.62 |
| | | | | H: 7.46 | 7.49 |
| | | | | $C_{25}H_{27}O_3N$ | $n_D^{24}$ 1.5470 |
| 206 | 277 | a | 89 | C: 77.09 | 77.11 |
| | | | | H: 6.99 | 6.80 |

| | | | | | |
|---|---|---|---|---|---|
| | | | | N: 3.60 | 3.53 |
| | | | | $C_{19}H_{20}O_4S$ | $n_D^{23}$ 1.5335 |
| 207 | 278 | a | 89 | C: 66.26 | 66.07 |
| | | | | H: 5.85 | 5.88 |
| | | | | S: 9.31 | 9.24 |
| | | | | $C_{23}H_{26}O_4$ | $n_D^{23}$ 1.5088 |
| 208 | 279 | a | 83 | C: 75.38 | 75.15 |
| | | | | H: 7.15 | 7.02 |
| | | | | $C_{23}H_{26}O_4$ | $n_D^{23}$ 1.5075 |
| 209 | 280 | a | 87 | C: 75.38 | 75.36 |
| | | | | H: 7.15 | 7.18 |
| | | | | $C_{20}H_{24}O_3$ | $n_D^{28.5}$ 1.5178 |
| 210 | 281 | a | 86 | C: 76.89 | 76.54 |
| | | | | H: 7.74 | 7.70 |
| | | | | $C_{21}H_{26}O_3$ | $n_D^{25}$ 1.5185 |
| 211 | 282 | a | 86 | C: 77.27 | 77.34 |
| | | | | H: 8.03 | 8.06 |
| | | | | $C_{22}H_{26}O_3$ | $n_D^{25}$ 1.5413 |
| 212 | 283 | a | 90 | C: 78.07 | 77.95 |
| | | | | H: 7.74 | 7.90 |
| | | | | $C_{17}H_{22}O_3$ | $n_D^{25}$ 1.4960 |
| 213 | 284 | a | 89 | C: 74.42 | 74.84 |
| | | | | H: 8.08 | 8.15 |
| | | | | $C_{23}H_{25}O_3N$ | $n_D^{25}$ 1.5407 |
| 214 | 285 | a | 85 | C: 76.01 | 76.10 |
| | | | | H: 6.93 | 6.88 |
| | | | | N: 3.85 | 3.62 |
| | | | | $C_{19}H_{22}O_3$ | $n_D^{28.5}$ 1.5202 |
| 215 | 286 | a | 91 | C: 76.48 | 76.41 |
| | | | | H: 7.43 | 7.55 |
| | | | | $C_{20}H_{24}O_3$ | $n_D^{28.5}$ 1.5165 |
| 216 | 287 | a | 87 | C: 76.89 | 76.71 |
| | | | | H: 7.74 | 7.85 |
| | | | | $C_{21}H_{26}O_3$ | $n_D^{23}$ 1.5153 |
| 217 | 288 | a | 88 | C: 77.27 | 77.25 |
| | | | | H: 8.03 | 8.09 |
| | | | | $C_{21}H_{26}O_3$ | $n_D^{27}$ 1.5150 |
| 218 | 289 | a | 88 | C: 77.27 | 77.45 |
| | | | | H: 8.03 | 8.01 |
| | | | | $C_{22}H_{28}O_3$ | $n_D^{27}$ 1.5134 |
| 219 | 290 | a | 92 | C: 77.61 | 77.76 |
| | | | | H: 8.29 | 8.25 |
| | | | | $C_{23}H_{28}O_3$ | $n_D^{27}$ 1.5363 |
| 220 | 291 | a | 89 | C: 78.37 | 78.43 |
| | | | | H: 8.01 | 8.08 |
| | | | | $C_{23}H_{26}O_3$ | $n_D^{25}$ 1.5345 |
| 221 | 292 | a | 89 | C: 78.83 | 78.85 |
| | | | | H: 7.48 | 7.48 |
| | | | | $C_{23}H_{24}O_3$ | $n_D^{25}$ 1.5363 |
| 222 | 293 | a | 90 | C: 79.28 | 79.20 |
| | | | | H: 6.94 | 7.02 |
| | | | | $C_{20}H_{26}O_3$ | $n_D^{28}$ 1.4999 |
| 223 | 294 | a | 86 | C: 76.40 | 76.49 |
| | | | | H: 8.34 | 8.55 |
| | | | | $C_{24}H_{26}O_3$ | $n_D^{22}$ 1.5356 |
| 224 | 295 | a | 82 | C: 79.53 | 78.91 |
| | | | | H: 7.23 | 7.28 |
| | | | | $C_{22}H_{24}O_2$ | $n_D^{19}$ 1.5238 |
| 225 | 296 | a | 89 | C: 82.46 | 82.41 |
| | | | | H: 7.55 | 7.53 |
| | | | | $C_{19}H_{22}O_3$ | $n_D^{20}$ 1.5542 |
| 226 | 297 | a | 78 | C: 76.48 | 76.55 |
| | | | | H: 7.43 | 7.37 |
| | | | | $C_{25}H_{26}O_3S$ | $n_D^{20}$ 1.5587 |
| 227 | 298 | a | 84 | C: 73.86 | 73.92 |
| | | | | H: 6.45 | 6.40 |
| | | | | S: 7.89 | 7.81 |
| | | | | $C_{23}H_{24}O_4$ | $n_D^{20}$ 1.5366 |
| 228 | 299 | a | 87 | C: 75.80 | 75.77 |
| | | | | H: 6.64 | 6.72 |
| | | | | $C_{23}H_{26}O_3$ | $n_D^{20}$ 1.5412 |
| 229 | 300 | a | 91 | C: 78.82 | 78.79 |
| | | | | H: 7.48 | 7.55 |

Most of the important intermediates of the present invention, i.e., disubstituted acetic acid, can effectively be prepared in high yields via one of the alternative procedures (A), (B) and (C) given below.

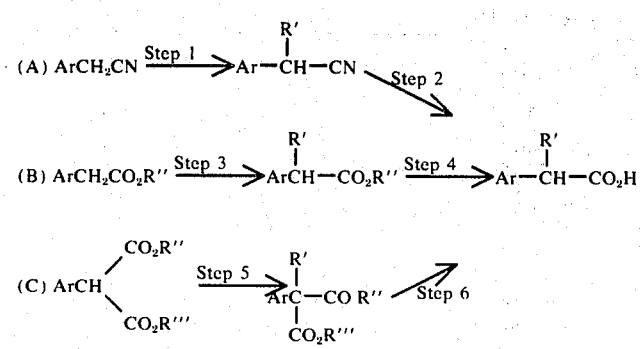

wherein Ar represents an aryl group, R' represents an alkyl, alkenyl group, R'' represents hydrogen or a lower alkyl group, and R''' represents a lower alkyl group.

Step 1: This procedure can be accomplished by alkylating the corresponding arylacetonitrile with an appropriate halide or sulfoxylate of the formula R'—X in an inert solvent (for example, ethers, tetrahydrofuran, benzene, toluene, etc. including liquid ammonia when $NaNH_2$ and the like is used as a base described below) in the presence of a base such as alkali metals, alkali metal hydrides, alkali metal amides and the like at room temperature or an elevated temperature.

Step 2: This procedure can be accomplished under the wellknown conditions commonly used for hydrolysis of a nitrile group, i.e., by heating the nitrile with a mineral acid or an alkali hydroxide.

Steps 3 and 4: This procedure can be accomplished by alkylating the corresponding phenylacetric acid or a loweralkyl ester thereof with an appropriate halide or sulfoxylate of the formula R'-X in an inert solvent in the presence of a base such as alkali metals or hydrides thereof, n-butyl lithium and the like at room temperature or an elevated temperature, and, when the loweralkyl ester is used for the alkylation, hydrolyzing the resulting ester with an appropriate acid or alkali in the usual manner.

Step 5: This procedure can be accomplished by reacting an arylmalonic acid ester (which is easily obtainable by carbalkoxylation of the corresponding arylacetic ester) with an appropriate halide or sulfoxylate of the formula R'-X in the presence of an alkali metal alkoxide or an alkali metal hydride as a base in an inert solvent or an alcohol corresponding to the alkali metal alkoxide.

STEP 6: This procedure can be accomplished under the wellknown conditions commonly used for hydrolysis of a usual ester, i.e., by hydrolyzing the ester with an acid or alkali to obtain the corresponding discarboxylic acid followed by heat-decarbonization to obtain the desired carboxylic acid, or can be accomplished by heating the diester with an alkali metal alkoxide in an alcohol whereby the diester is easily converted into a monoester by decarboxylation and hydrolyzing the monoester by the well-known procedure to obtain the corresponding carboxylic acid in high yields.

The preparation of the intermediates, carboxylic acids, can be illustrated by the following Synthesis Examples, but they are not to be construed as limiting the processes or intermediates of the present invention.

SYNTHESIS EXAMPLE 1

α-Isopropyl-4-methoxyphenylacetonitrile 14.72 g (0.1 mole) of 4-methoxyphenylacetonitrile in 10 ml of dry toluene was added to a stirred solution of sodium hydride (2.64 g, 0.11 mole) and isopropylbromide (18.45 g, 0.15 mole) in 100 ml of dry toluene and 10 ml of dry dimethylformamide which was heated at 70° C, in 30 minutes. After addition was completed, the mixture was heated at a temperature of from 80° to 85° C for 3 hours, and cooled to room temperature then poured into 200 g of ice-water.

Organic layer was separated and the aqueous layer was extracted with ether twice. Combined organic layer was washed successively with water and saturated sodium chloride solution, and dried over anhydrous sodium sulfate. The solvent was removed in vacuo and the residual oil was distilled in vacuo to afford 15.70 g (b.p. 95°–96°/0.15 mmHg, 83.0%) of α-isopropyl-4-methoxyphenylacetonitrile.

In similar manners, following α-isopropylphenylacetonitriles were obtained.

|  |  | b.p.20°C/mmH, | Yield (%) |
|---|---|---|---|
| 4-bromo-α-isopropylphenyl-acetonitrile | 1) | 90 – 93 /0.10 | 82.1 |
| 4-ethl-d- '' | 2) | 96 – 93°/0.10 | 85.1 |
| 4-isopropyl-α- '' | 3) | 100 – 102°/0.40 | 83.5 |
| 3-chloro-α- '' | 4) | 104 – 106°/0.30 | 80.2 |
| 4-fluoro-α- '' | 5) | 89 – 90°/5.0 | 80.7 |
| 3-fluoro-α- '' | 6) | 89 – 90°/5.0 | 81.1 |
| 4-thiomethyl-α- '' | 7) |  105°/0.10 | 75.1 |
| 2,4,6-trimethyl-α- '' | 8) | 87 – 88°/0.20 | 53.1 |
| 3-trifluoromethyl-α- '' | 9) | 95 – 96°/5.0 | 87.9 |
| 3,4-methylenedioxy-α- '' | 10) | 95 – 100°/0.2 | 78.2 |
| 3-phenoxy-α- '' | 11) | 147 – 148°/0.3 | 85.2 |

1. Starting 4-bromophenylacetonitrile was synthesized from 4-bromotoluene which was brominated at 180° C with bromine and converted into nitrile with potassium cyanide in $DMSO-H_2O$.

2. Ethylbenzene was chloromethylated with Kosolopoff method (JACS, 68, 1670 (1946)) and the chloride was purified by fractional distillation, then converted into nitrile in similar manner described above.

3. Isopropylbenzene was chloromethylated and converted into a nitrile.

4. Commercially available 3-chlorobenzylchloride was converted into a nitrile similarly.

5,6. 3-fluorotoluene and 4-fluorotoluene were brominated with NBS in carbon tetrachloride then converted into nitriles.

7. Thioanisole was chloromethylated with paraformaldehyde and zinc chloride in poor conversion, then converted into nitrile.

8. Mesitylene was chloromethylated and converted into a nitrile. In this case, alkylation proceeded very slowly even though an elevated temperature (110° C) and longer reaction times (15 hours) were tried.

9. 3-bromobenzotrifluoride was converted to 3-hydroxymethylbenzourifluoride via Grignard method (R. Filler and H. Novar, J.O.C., 25, 733 (1960)) and converted into a bromide (HBr-$H_2SO_4$) and a nitrile (KCN-DMSO), successively.

10. Piperonyl alcohol was converted into a chloride with thionyl chloride at 0° C, followed by KCN/DMSO to afford the nitrile.

11. m-phenoxytoluene which was obtained from m-cresol and bromotoluene was brominated at 230° C with bromine, and the corresponding bromide was converted into a nitrile similarly.

SYNTHESIS EXAMPLE 2

4-Bromo-α-isopropyl-phenylacetic acid 20 g of 4-bromo-α-isopropylphenylacetonitrile was heated with 140 ml of sulfuric acid (50V/V%) at 145° C for 6 hours. The cooled reaction mixture was poured onto 150 g of ice, and extracted with ether (100 ml × 3). The ether layers were combined and extracted with three 70 ml portions of cold 5% sodium hydroxide solution, and the aqueous extracts were acidified with concentrated hydrochloric acid, and then extracted with ether. The ether extract was washed successively with water, saturated sodium chloride solution, dried over anhydrous sodium sulfate. Removal of the solvent gave 16.9 g (78.2%) of white crystals, which were sufficiently pure for use in next step. A portion of the crystals was recrystallized from benzene, melting point: 97–98° C.

SYNTHESIS EXAMPLE 3

4-Methoxy-α-isopropylphenylacetic acid 12.8 g of 4-methoxy-α-isopropylphenylacetonitrile was heated under reflux (140° C) with 200 ml of ethyleneglycol and 40 g of 50% aqueous potassium hydroxide solution for 8 hours. The cooled reaction mixture was poured into 200 g of ice-water, which was washed with ether. The aqueous layer was acidified with concentrated hydrochloric acid, and extracted with ether (150 ml × 3). The combined ether extract was washed successively with water, saturated sodium chloride, then dried over anhydrous sodium sulfate. Removal of the solvent gave 11.30 g (80.4%) of white crystals. The acid recrystallized from benzene melted at 146°–148° C.
acid recrystallized from benzene melted at 146° – 148° C.

In similar manners following acids were prepared.

|  | Method of Hydrolysis | Yields | | N.M.R. signals (CHCl$_3$, in ppm) |
| --- | --- | --- | --- | --- |
| 3-trifluoromethyl-α-isopropyl-phenyl-acetic acid | A | 25.0 | 0.74<br>1.07<br>1.9–<br>3.22<br>7.4 –<br>10.6 | (3H, d.J=7Hz),<br>(3H, d.J=7Hz),<br>2.6 (1H, m.),<br>(1H, d.J=10Hz),<br>7.7 (4H, m.),<br>(1H, b.S) |
| 4-fluoro-α-isopropyl-phenylacetic acid | A | 85.2 | 0.69<br>1.05<br>1.9–<br>3.10<br>6.9–<br>9.70 | (3H, d.J=7Hz),<br>(3H, d.J=7Hz),<br>2.6 (1H, m.)<br>(1H, d.J=12Hz),<br>7.4 (4H, m.),<br>(1H, b.S.) |
| 4-thiomethyl-α-isopropyl-phenyl-acetic acid | B | 78.2 | 0.69<br>1.07<br>2.42<br>3.07<br>7.19<br>9.64 | (3H, d.J=6.5Hz),<br>(3H, d.J=6.5Hz),<br>(3H, S),<br>(1H, d.J=10Hz),<br>(4H, S.),<br>(1H, b.S.) |
| 2,4,6-trimethyl-α-isopropyl-phenyl-acetic acid | A | 34.5 | 0.61<br>1.15<br>1.22<br>1.32<br>2.25 –<br>3.68<br>6.82<br>9.50 | (3H, d.J=7Hz),<br>(3H, d.J=7Hz),<br>(3H, S.),<br>(6H, S.),<br>2.95 (1H, m.),<br>(1H, d.J=10Hz),<br>(2H, b.S.),<br>(1H, b.S.) |

| | Method of Hydrolysis | Yields | N.M.R. signals (CHCl$_3$, in ppm) | |
|---|---|---|---|---|
| 3-methoxy-α-isopropyl-phenylacetic acid | B | 87.2 | 0.65<br>1.05<br>1.7 –<br>3.07<br>3.75<br>6.5 –<br>6.2 | (3H, S.J=7Hz),<br>(3H, S.J=7Hz),<br>2.6 (1H, m.),<br>(1H, d.J=11Hz),<br>(3H, S.),<br>7.1 (4H, m.),<br>(1H, b.S.) |
| 4-methyl-α-isopropyl-phenylacetic acid | A | 88.2 | 0.68<br>1.05<br>1.95 –<br>2.29<br>3.05<br>7.11<br><br>9.52 | (3H, d.J=7Hz),<br>(3H, d.J=7Hz),<br>2.50 (1H, m.),<br>(3H, S.),<br>(1H, d.J=11Hz),<br>(centered, 4H,<br>AB type 8),<br>(1H, b.S.) |

Signal patterns were designated as follows.
S: signlet, d: doublet, m: multiplet, bS: broad Singlet
Hydrolysis Method A: 50% H$_2$SO$_4$, Method B: Ethyleneglycolaqueous KOH

SYNTHESIS EXAMPLE 4

Diethyl-2-phenyl-2-allyl-malonate

Diethyl-2-phenylmalonate (23.60 g, 0.10 mole, prepared from ethylphenylacetate, Org. Synth. Call, Vol. 2, 288) in 20 ml of dry benzene was added to a stirred solution of sodium hydride (2.38 g, 0.12 mole) in 150 ml of dry benzene at 30° – 40° C, and the mixture was kept at 40° C for 30 minutes. To the white enolate generated was added a solution of allyl bromide (24.2 g, 0.10 mole) in 20 ml of dry benzene at 5° C, thereafter stirring continued at room temperature for one hour.

The reaction mixture was poured into 200 ml of ice-water, and the organic layer was separated. The aqueous layer was extracted with ether (two 100 ml portions). The organic layers were combined, and washed successively with 5% hydrochloric acid, water and saturated sodium chloride solution, then dried over anhydrous sodium sulfate. The solvent was removed in vacuo, and the residual oil was distilled at reduced pressure to afford 24.27 g (87.90%, b.p. 115° – 120°/0.25 mmHg) of diethyl-2-phenyl-2-allyl-malonate.

SYNTHESIS EXAMPLE 5

Ethyl-α-allylphenylacetate

Diethyl allylphenyl malonate (20.0 g, 0.072 mole) in 250 ml of dry EtOH was heated under reflux with 7.4 g of sodium ethoxide for 5 hours.

Ethanol was removed in vacuo, and the residue was poured to 75 g of ice-water. The mixture was extracted with ether (three 50 ml portions), ether layer was washed with saturated sodium chloride solution, dried over anhydrous sodium sulfate. Removal of the solvent, and distillation at reduced pressure afforded 12.54 g (b.p. 60° – 63° /0.13 mmHg, 85.3%) of the phenyl acetate.

SYNTHESIS EXAMPLE 6

α-Allyl-phenyl acetic acid

Above ethylester was hydrolyzed with 10% potassium hydroxide in methanol at room temperature in a usual manner to give the acid (yield 94.6%, m.p. 34° C).

SYNTHESIS EXAMPLE 7

Diethyl-2-phenyl-2-propargyl malonate

In a similar manner to Example 4, the malonate was prepared in 81.7% yield (b.p. 115°– 120°/0.15 mmHg).

SYNTHESIS EXAMPLE 8

α-Propargyl phenyl acetic acid 20.0 g (0.073 mole) of diethyl-2-phenyl-2-propargyl malonate was hydrolyzed in 330 g of 5% methanolic potassium hydroxide at reflux temperature for 2 hours. Methanol was removed in vacuo, and the residue was dissolved in 150 ml of cold water, acidification with concentrated HCl caused a spontaneous decarboxylation to give the monocarboxylic acid, which was collected by ether extraction. (12.4 g, 97.6%, m.p. 90° – 93° C)

SYNTHESIS EXAMPLE 9

Although the compound which bears an isopropenyl group on α-position such as compounds No. 83, No. 85, No. 125, can be prepared in the usual esterification method using corresponding acid chloride, the double bond of the isopropenyl group readily isomerized to α-β position to make the acid or acid chloride into a mixture of double bond positions. A low yield was attained after chromatographic purification.

Following routes seemed to be better than the usual methods.

3'-Phenoxybenzyl -α-isopropenyl-4-methoxyphenylacetate (Compound No. 82)

1. To a solution of isopropylmagnesium bromide, which was prepared from 38.1 g of isopropylbromide and 7.3 g of magnesium in 90 ml of dry ether, was added a solution of 4-methoxyphenylacetic acid (16.6 g) in 100 ml of dry tetrahydrofuran at an ice-bath temperature, thereafter the solution was stirred at room temperature for 2 hours. Dry acetone (7.0 g), diluted with 20 ml of dry toluene, was added to the solution, and it was heated to reflux for 5 hours. Cooled solution was acidified with 15% sulfuric acid, the aqueous phase separated, which was extracted with ether. Combined organic layers were extracted with 10% sodium carbonate solution. Carbonate extract was acidified with concentrated hydrochloric acid and extracted with ether. Ether extract was dried over anhydrous sodium sulfate. Removement of the solvent and a recrystallization from ethyl acetate afforded 12.4 g of 4-methoxy-$\beta,\beta$-dimethylatropic acid (55.2%, m.p. 124° – 125° C).

2. To a solution of 4-methoxy-$\beta,\beta$-dimethylatropic acid (5.0 g) and triethylamine (4.5 g) in 50 ml of dimethylformamide, was added 7.0 g of 3-phenoxybenzylbromide gradually at an ice-bath temperature, and stirred overnight at room temperature. The mixture was poured into cold 10% $H_2SO_4$ and extracted with ether. The ether layer was washed with 10% sodium carbonate solution and dried over anhydrous sodium sulfate. Removement of the solvent gave 4.8 g of crude hydroxyester, which was dehydrated with $P_2O_5$ in benzene at 80° C for 13 hours. Filtration, and removement of the solvent gave crude isopropenyl-ester as a dark oil. Purification with silica-gel chromatography afforded 1.9 g of pure ester (40.5%, $n^{16}_D$ 1.5798)

SYNTHESIS EXAMPLE 10

Ethyl-2-(cyclohexane-1'-ol-1'-yl) -butyrate

This was prepared from ethyl-2-bromobutyrate (29.3 g), cyclohexanone (14.7 g) and zinc (9.51 g) in benzene (50 ml) and toluene (25 ml) under usual Reformatsky conditions (b.p. 166° – 117°/4 mmHg, yield 16.4 g, 51.0%).

SYNTHESIS EXAMPLE 11

Ethyl-2(cyclohexene-1-yl)-butyrate

Above hydroxyester (16.4 g) was heated under reflux with phosphorous pentoxide (11 g) in 60 ml of dry benzene for 3 hours. Cooled mixture was poured onto 80 ml of cold water, organic layer was separated and washed with saturated sodium chloride solution. Solvent was removed in vacuo, and the residue was distilled under reduced pressure to afford 11.6 g of pale yellow oil. (76.5%, b.p. 88° – 92°/4 mmHg)

SYNTHESIS EXAMPLE 12

Ethyl-2,3-diethyl-3-hydroxy-pentanoate

In similar manners described in Example 10, this was prepared from 3-pentanone and ethyl-2-bromobutyrate. (yield 52.8%, b.p. 113° – 121°/20 mmHg)

SYNTHESIS EXAMPLE 13

The hydroxyester obtained in Example 12, was dehydrolyzed with phosphorous pentoxide in benzene in a manner described above. (yield 68.2%, b.p. 95° – 98°/22 mmHg)

The compounds of the type designated as Compound Nos. 18, 21, 245, 246 and 248 were prepared from the corresponding carboxylic acid or an acid chloride derived therefrom which is obtained by hydrolyzing the ethyl ester prepared in the similar manner as described in Synthesis Examples 10 14 13. The hydrolysis can be effected by the conventional procedure using sodium hydroxide or potassium hydroxide in methanol at room temperature. The carboxylic acid thus obtained was found to contain a small amount of isomers with respect to double bonds (up to about 10%), but the crude carboxylic acid was subjected to esterification without isolating impurities (isomers) and the product was purified by silica gel chromatography in the final step.

The substituted ester compounds represented by the formula (I) exhibit an excellent pesticidal activity and are expected to have a repelling activity against mites as well as a synergestic activity with other biologically active agents, and can be employed in a wide variety of applications at low cost as pesticidal compositions for use in agricultural and horicultural, forest, sanitary fields as well as in a stockroom of cereals and a composition for controlling mites.

In practical use of these compounds, an appropriate amount of one or more solvents, filles, diluents, active agents, dispersing agents, surface active agents, spreaders, pressure-imparting agents, emulsifying agents and attractants can be incorporated into the ester compounds of this invention to form an emulsifiable concentrate, a wettable powder, a dust, a granule, a fine grain, a coating agent, a powder, an oil preparation, an aerosol, a mosquito coil, a smoking agent, a fumigating agent, a mosquito insence agent for electrical vaporization, and the like.

The effect of the pesticidal compositions of this invention is further illustrated by the following Experiments.

EXPERIMENTAL EXAMPLE 1

An emulsifiable concentrate was prepared by blending each of the compounds (1) to (300) of the present invention, xylol and Sorpol SM-200 (trade name; manufactured by Toho Chemical Co., Ltd.) in a proportion of 25%, 50% and 25% (by weight), respectively. 20 to 25 day-old rice plants after seeding were grown in pots and sprayed with each 300-fold dilute solution of the emulsifiable concentrates thus prepared and a 300-fold dilute solution of carbaryl 30% wettable powder diluted with water as a control commercial agent in an amount of 10 ml/pot in each case and then the pots were covered by a cylindrical metal net. 15 smaller brown planthoppers (*Delphacodes striatella* Fallen) per group were released in each of the pots treated with the carbaryl wettable powder, and compound (1) to (21) and (102) to (110), while 15 green rice leafhopper ((*Nephotettix bipuntatus cincticeps* Uhler) per group were released in each of the pots treated with the carbaryl wettable powder and compounds (22) to (101)

and (111) to (300). Observation on survival one day after the treatment revealed that each of the compounds of this invention exhibits more than 90% killing effect as in the case of carbaryl.

EXPERIMENTAL EXAMPLE 2

Of the emulsifiable concentrates prepared in Experimental Example 1, each of those prepared from the compounds of Table 1 below was diluted with water to each of test concentrations and a 200 ml portion thereof was added to a 300 ml volume beaker. 30 larvae of mosquito per group were released in each of the beaker and allowed to stand for 1 day. Survival was observed and a $LC_{50}$ (50% lethal concentration) was determined by calculating a percent killing in each case. The results obtained are also shown in Table 1. As a control, lindane emulsifiable concentrate was used.

Table 1

| Insecticidal Activity on Larvae of Mosquito (Culex pipiens) | | | |
|---|---|---|---|
| Test Emulsifiable Concentrate | $LC_{50}$ (ppm) | Test Emulsifiable Concentrate | $LC_{50}$ (ppm) |
| Compound (1) | 0.0015 | Compound (2) | 0.0034 |
| " (10) | 0.0030 | " (14) | 0.0026 |
| " (16) | 0.0014 | " (102) | 0.0095 |
| " (103) | 0.0092 | " (104) | 0.0120 |
| " (105) | 0.0105 | " (110) | 0.0125 |
| " (111) | 0.0025 | " (112) | 0.0046 |
| " (113) | 0.0053 | " (115) | 0.0050 |
| " (119) | 0.0044 | " (120) | 0.0040 |
| Compound (121) | 0.0037 | Compound (125) | 0.0032 |
| " (126) | 0.0056 | " (128) | 0.0047 |
| " (145) | 0.0039 | " (165) | 0.0012 |
| " (167) | 0.0043 | " (177) | 0.0074 |
| " (180) | 0.0072 | " (181) | 0.0820 |
| " (183) | 0.0885 | " (184) | 0.0078 |
| " (204) | 0.0075 | " (206) | 0.0032 |
| " (210) | 0.0035 | " (212) | 0.0037 |
| " (214) | 0.0127 | " (215) | 0.0132 |
| " (226) | 0.0135 | " (227) | 0.0019 |
| " (231) | 0.0014 | " (298) | 0.0097 |
| Lindane | 0.22 | | |

EXPERIMENTAL EXAMPLE 3

A 2000fold dilute solution of each of the emulsifiable concentrates prepared in Experimental Example 1 from the compounds of Table 2 below was sprayed on a 12 day-old seedling of mottled kidney beans after seeding grown in a pot in an amount of 10 ml/pot. The seedling thus treated was cut off and put in a wide opening bottle. In the same manner, an untreated seedling of mottled kidney beans in the same stage was cut off and put in another wide opening bottle. Another fresh seedling was fixed with pins bridging on the former treated seedling and the latter untreated seedling. A leaf of mottled kidney beans on which a number of spider mites (*Tetranychus telarius*) were parasitic was placed on the middle of the bridging seedling and allowed to stand for 2 days. Activity on repellency was assessed by investigating the numbers of mites swarming on the treated seedling and the untreated seedling. The assessment standards are as follows:

| — : | The ratio of the number of mites on the untreated seedling to that on the treated seedling | 1 : 1 |
|---|---|---|
| + : | " | up to 4 : 1 |
| ++ : | " | greater than 4 : 1 |

The results obtained was shown in Table 2 below.

Table 2

| Repellent Activity on Spider Mites | | | |
|---|---|---|---|
| Test Emulsifiable Concentrate | Repellency | Test Emulsifiable Concentrate | Repellency |
| Compound (1) | ++ | Compound (3) | + |
| " (4) | ++ | " (10) | ++ |
| " (18) | + | " (23) | + |
| " (29) | ++ | " (35) | + |
| " (45) | ++ | " (65) | + |
| " (73) | + | " (82) | ++ |
| " (92) | ++ | " (98) | ++ |
| " (116) | ++ | " (117) | ++ |
| Compound (118) | ++ | Compound (121) | ++ |
| " (124) | + | " (127) | ++ |
| " (130) | + | " (165) | ++ |
| " (168) | ++ | " (175) | ++ |
| " (176) | ++ | " (177) | ++ |
| " (178) | ++ | " (200) | ++ |
| " (204) | ++ | " (206) | ++ |
| " (210) | ++ | " (216) | ++ |
| " (217) | ++ | " (218) | ++ |
| " (219) | ++ | " (220) | ++ |
| " (221) | ++ | " (227) | ++ |
| " (234) | ++ | " (235) | ++ |

EXPERIMENTAL EXAMPLE 4

0.2% oil preparation was prepared from each of the compounds (1), (2), (8), (14), (22), (25), (26), (27), (51), (62), (73), (82), (86), (88) to (90), (92), (94), (96), (111), (119), (121), (165), (175), (180), (184), (185), (195), (200), (201), and (208) and allethrin as a control using deodorized kerosene. About 50 adult mosquitoes (*Culex pipiens*) were released in a (70 Cm)$^3$ volume glass box and sprayed with each of the oil preparations obtained above in an amount of 0.7 ml under a pressure of 1.5 Kg/cm$^2$. It was found that more than 80% of mosquitoes was knocked down by both allethrin and the compounds of this invention.

EXPERIMENTAL EXAMPLE 5

20 oriental house flies per group were released in a (70 cm)$^3$ volume glass box and sprayed with each of the oil preparations prepared in Experimental Example 4 from the compounds of Table 3 below and allethrin in an amount of 0.7 ml under a pressure of 1.5 Kg/cm$^2$. The test was repeated several times and the knock down of the flies was observed to determine $KT_{50}$ (50% knock-down time). The results obtained are shown in Table 3.

Table 3

Activity on Knock-Down Against Oriental House Flies

| Test Oil Preparation | | $KT_{50}$ (sec.) | Test Oil Preparation | | $KT_{50}$ (sec.) |
|---|---|---|---|---|---|
| Compound | (1) | 167 | Compound | (8) | 128 |
| " | (22) | 136 | " | (51) | 104 |
| " | (62) | 154 | " | (63) | 140 |
| " | (82) | 132 | " | (88) | 147 |
| " | (89) | 155 | " | (96) | 92 |
| " | (111) | 138 | " | (119) | 132 |
| " | (121) | 130 | " | (165) | 145 |
| " | (175) | 152 | " | (180) | 157 |
| " | (184) | 142 | " | (185) | 137 |
| Compound | (195) | 140 | Compound | (200) | 114 |
| " | (201) | 105 | " | (208) | 150 |
| Allethrin | | 186 | | | |

EXPERIMENTAL EXAMPLE 6

To each of the compounds (22), (51), (62), (63), (82), (86), (125), (150), (160), (176), (177), (178), (184), (185), (191), (195), (200), (201), (204), (208), (210), (212) and (226) was added piperonyl butoxide in an amount of 5 times that of the active ingredient, respectively to prepare an acetone solution having a given concentration. Each of the thus prepared acetone solutions was applied onto a thoracic dosal plate of oriental house flies using a microshringe to observe a synergestic effect on insecticidal activity by piperonyl butoxide. Potentiation magnification of insecticidal activity by the addition of piperonyl butoxide is shown in Table 4.

Table 4

Potentiation Effect on Insecticidal Activity by the Addition of Piperonyl Butoxide

| Test Compound | | Potentiation Magnification | Test Compound | | Potentiation Magnification |
|---|---|---|---|---|---|
| Compound | (22) | 5.0 | Compound | (51) | 7.2 |
| Compound | (62) | 5.3 | Compound | (63) | 4.8 |
| " | (82) | 6.7 | " | (86) | 4.5 |
| " | (119) | 5.5 | " | (125) | 6.0 |
| " | (150) | 4.2 | " | (160) | 7.2 |
| " | (176) | 5.2 | " | (177) | 5.8 |
| " | (178) | 5.4 | " | (184) | 5.6 |
| " | (185) | 5.0 | " | (191) | 4.3 |
| " | (195) | 5.7 | " | (200) | 7.5 |
| " | (201) | 7.0 | " | (204) | 4.7 |
| " | (206) | 5.1 | " | (208) | 5.2 |
| " | (210) | 4.8 | " | (212) | 5.0 |
| " | (226) | 4.5 | | | |

As is apparent from the above Experimental Examples the compounds of this invention exhibit an excellent biological activity on various noxious insects and mites and also are of low toxicity.

Oral toxicity to mice for representative compounds is shown in the Table below.

Table

| Test Compound | | $LD_{50}$ (mg/Kg) | Test Compound | | $LD_{50}$ (mg/Kg) |
|---|---|---|---|---|---|
| Compound | (1) | >1000 | Compound | (2) | >1000 |
| " | (8) | 750 | " | (22) | 900 |
| Compound | (62) | >1000 | Compound | (63) | >1000 |
| " | (80) | >1000 | " | (82) | >1000 |
| " | (108) | >1000 | " | (119) | >1000 |
| " | (125) | >1000 | " | (129) | >1000 |
| " | (130) | >1000 | " | (145) | >1000 |
| " | (150) | >1000 | " | (176) | >1000 |
| " | (184) | 940 | " | (206) | >1000 |

The compositions according to the present invention are very useful for controlling insanitary insects such as mosquitoes, flies and cockroaches, grain insects such as rice weevil (*Calandra oryzae*) and mites as well as agricultural noxious insects such as plant-hoppers, green rice leafhopper (*Nephotettix bipuntatus cinticeps* Uhler), cabbage army worms (*Barathra brassicae* Linne), diamond-back moths (*Plutella maculipennis* Curtis), noctuidae, cabbage worm (*Pieris rapae* Linne), rice stem boress (*Chilo suppressalis* Walker), aphids, tortrixes, leaf-miners and the like.

They are also superior whenever they may be freely used for harvested crops, horticultural application, cultures in green house, and packaging materials for foodstuffs.

In preparing the compositions according to the present invention, it is possible to obtain more excellent controlling effects by employing a combination of two or more compounds of this invention, and further, it is possible to obtain various compositions which are useful for a wide variety of applications by combining one or more compounds of this invention with other pesticidal compounds, for example, organochloric compounds such as DDT, BHC, Methoxychlor and the like; organic phosphorus compounds such as Sumithion (trade name of Sumitomo Chemical Company Limited), DDVP, diazinon, phenthion, Cyanox (trade name of Sumitomo Chemical Company Limited) and the like; carbamates such as 1-naphthyl-N-methylcarbamate, 3,4-dimethylphenyl N-methylcarbamate, 3,5-dimethylphenyl N-methylcarbamate and the like; cyclopropanecarboxylic acid esters such pyrethrin, allethrin, Neopynamin (trade name of Sumitomo Chemical Company Limited), Chrysron (trade name of Sumitomo Chemical Company Limited), 3-phenoxybenzyl chrysanthemate, 5-propargylfurfuryl chrysanthemate and their geometrical or optical isomers and the like, as well as piperonyl butoxide, sulfoxide, safroxane, isobornyl thiocyano acetate (I.B.T.A.) and octachloro dipropyl ester (S-421) which potentiate the effect of the esters synergetically; terephthalic acid, isophthalic acid and BHT which are generally used in fumigating preparations; phenol derivatives used as a stabilizer; bisphenol derivatives; arylamines such as phenyl-α-naphthylamine, phenyl-β-naphthylamine, a condensate of phenetidin and acetone and the like; other insecticidal agents or miticidal agents such as Padan, Galecron, antimicrobial agents, nematocidal agents, herbicidal agents, fertilizers and other agricultural agents. These compositions are expected to be useful for saving man power for application of these agricultural agents and for obtaining synergetic activities between the active ingredients of the composition.

The preparation of compositions and the effect of compounds of this invention are further illustrated by the following Formulations and Examples, but they are not to be construed as limiting the scope of this invention. The parts used in formulations are by weight unless otherwise indicated.

FORMULATION 1

To 20 parts of each of Compound Nos. 1 to 110 of this invention, there were added 10 parts of Sumithion L (as described previously), 10 parts of Sorpol SM-200 (as described previously), 60 parts of xylol, and the mixture was dissolved by thoroughly stirring and mixing to obtain an emulsifiable concentrate in each case.

FORMULATION 2

To 10 parts of each of Compound Nos. 111 to 192 of this invention, there were added 10 parts of Cyanox (as described previously), 10 parts of Sorpol SM-200 (as described previously) and 70 parts of xylol, and the mixture was dissolved by thoroughly stirring and mixing to obtain an emulsifiable concentrate in each case.

FORMULATION 3

To 15 parts of each of Compound Nos. 193 to 232 of this invention, there were added 30 parts of piperonyl butoxide, 15 parts of Sorpol SM-200 (as described previously) and 40 parts of xylol, and the mixture was dissolved by thoroughly stirring and mixing to obtain an emulsifiable concentrate in each case.

FORMULATION 4

To 15 parts of each of Compound Nos. 233 to 300 of this invention, there were added 20 parts of a 25% pyrethrin extract, 20 parts of piperonyl butoxide, 15 parts of Sorpol Sm-200 (as described previously) and 30 parts of xylol, and the mixture was dissolved by thoroughly stirring and mixing to obtain an emulsifiable concentrate in each case.

FORMULATION 5

0.5 parts of each of Compound Nos. 1, 10, 102, 103, 108 and 111 to 115 was dissolved in kerosene in an amount sufficient to make 100 parts thereby obtaining an oil preparation in each case.

FORMULATION 6

To 0.2 parts of each of Compound Nos. 116 to 192 of this invention, there were added 0.1 parts of allethrin α-trans chrysanthemate and 1.5 parts of safroxane, and the mixture was dissolved in kerosene to prepare 100 parts of an oil preparation in each case.

FORMULATION 7

To 0.2 parts of each of Compound Nos. 193 to 300 of this invention, there were added 0.1 parts of Neopynamine and 1.5 parts of S-421, and the mixture was dissolved in kerosene to prepare 100 parts of an oil preparation in each case.

FORMULATION 8

To 10 parts of each of Compound Nos. 1 to 110 of this invention, there were added 10 parts of 1-naphthyl-N-methylcarbamate and 5 parts of Sorpol SM-200 (as described previously) followed by mixing. 75 parts of 300-mesh talc was then added to the mixture and the resulting blend was thoroughly stirred in a triturator to obtain an wettable powder in each case.

FORMULATION 9

The active pesticidal ingredients having a composition shown in Table below were dissolved in 20 ml of methanol and the resulting solution was mixed with 100 g of a carrier for mosquito coil (a mixture of tabu powder, pyrethrum marc and wood powder in a proportion of 3:5:1, respectively), followed by blending uniformly. After methanol was evaporated, 150 ml of water was added to the blend, and the mixture was thoroughly kneaded, molded and dried to prepare a mosquito coil in each case.

| Formulations of Mosquito Coil | | |
|---|---|---|
| No. | Composition | |
| 1. | Compound No. 1 | 0.3 g |
|  | Allethrin | 0.3 g |
| 2. | Compound No. 8 | 0.3 g |
|  | Allethrin | 0.3g |
| 3. | Compound No. 22 | 0.3 g |
|  | Allethrin | 0.2 g |
|  | BHT | 0.3 g |
| 4. | Compound No. 37 | 0.3 g |
|  | Allethrin | 0.3 g |
| 5. | Compound No. 51 | 0.3 g |
|  | Allethrin α-trans chrysanthemate | 0.1 g |
|  | BHT | 0.4 g |
| 6. | Compound No. 62 | 0.2 g |
|  | 5-Propargylfurfuryl chrysanthemate | 0.2 g |
|  | BHT | 0.8 g |
| 7. | Compound No. 82 | 0.3 g |
|  | 5-Propargyl-2-methyl-3-furylmethyl chrysanthemate | 0.1 g |
|  | BHT | 0.4 g |
| 8. | Compound No. 146 | 0.3 g |
|  | Allethrin d-cis,trans chrysanthemate | 0.1 g |
|  | BHT | 0.5 g |
| 9. | Compound No. 169 | 0.3 g |
|  | Allethrin | 0.2 g |
|  | BHT | 0.5 g |
| 10. | Compound No. 184 | 0.3 g |
|  | Allethrin | 0.3 g |
|  | BHT | 0.3 g |

FORMULATION 10

The active pesticidal ingredients having a composition shown in Table below were dissolved in a mixed solvent comprising xylol and refined kerosene (1:1 by volume) to prepare 15 parts of solution and the solution was filled in an aerosol dispensing container. After a valve was mounted to the container, the aerosol dispenser was pressurized by charging 85 parts of a propellant (for example, freon, vinyl chloride monomer, luquified petroleum gas, etc.) to obtain an aerosol preparations.

| Aerosol Formulations | | |
|---|---|---|
| No. | Composition | |
| 1. | Compound No. 22 | 0.3 (parts) |
|  | 3-Phenoxybenzyl-d-cis, trans chrysanthemate | 0.1 |

Aerosol Formulations

| No. | Composition | |
|---|---|---|
| 2. | Compound No. 22 | 0.2 |
| | Neopynamin | 0.2 |
| | I.B.T.A. | 1 |
| 3. | Compound No. 62 | 0.2 |
| | Allethrin d-trans chrysanthemate | 0.2 |
| | Safroxane | 2 |
| 4. | Compound No. 62 | 0.3 |
| | DDVP | 0.3 |
| 5. | Compound No. 82 | 0.2 |
| | Sumiothin | 0.3 |
| | Neopynamin | 0.2 |
| 6. | Compound No. 82 | 0.4 |
| | Piperonyl butoxide | 2.0 |
| 7. | Compound No. 88 | 0.2 |
| | Neopynamin | 0.2 |
| | Chrysron | 0.1 |
| 8. | Compound No. 89 | 0.3 |
| | Allethrin d-trans chrysanthemate | 0.2 |
| 9. | Compound No. 96 | 0.2 (parts) |
| | Allethrin d-cis, trans chrysanthemate | 0.2 |
| | Safroxane | 2 |
| 10. | Compound No. 102 | 0.4 |
| | Neopynamin | 0.1 |
| | Piperonyl butoxide | 1.5 |
| 11. | Compound No. 103 | 0.4 |
| | Allethrin | 0.1 |
| | S-421 | 1.5 |
| 12. | Compound No. 108 | 0.4 |
| | 25% Pyrethrin extract | 0.5 |
| | Piperonyl butoxide | 1.0 |
| 13. | Compound No. 125 | 0.4 |
| | I.B.T.A. | 2 |

FORMULATION 11

The active pesticidal ingredients having a composition shown in Table below were dissolved in an appropriate amount of chloroform, and the solution was adsorbed uniformly on the surface of asbestos having a size of 2.5 cm × 1.5 cm and a thickness of 0.3 mm. Another piece of asbestos having the same size and thickness was then placed on the treated surface of the above asbestos to prepare a fibrous fumigation pesticidal composition (mat) for heating on a hot plate. As a fibrous carrier, those having the same effect as that of asbestos such as a pulp board, etc. may also be used in place of asbestos.

Formulation of Mat for Heating on Hot Plate

| No. | Composition | |
|---|---|---|
| 1. | Compound No. 51 | 0.05 g |
| | Allethrin | 0.02 g |
| | Piperonyl butoxide | 0.07 g |
| 2. | Compound No. 63 | 0.07 g |
| | Allethrin d-trans chrysanthemate | 0.01 g |
| | Piperonyl butoxide | 0.1 g |
| 3. | Compound No. 80 | 0.5 g |
| | 5-Propargyl furylmethyl chrysanthemate | 0.02 g |
| | Piperonyl butoxide | 0.15 g |
| | BHT | 0.1 g |
| 4. | Compound No. 82 | 0.04 g |
| | Allethrin | 0.04 g |
| | Piperonyl butoxide | 0.08 g |
| | BHT | 0.1 g |
| 5. | Compound No. 88 | 0.05 g |
| | 5-Propargyl-2-methyl-3-furyl-methyl chrysanthemate | 0.02 g |
| | Piperonyl butoxide | 0.15 g |
| 6. | Compound No. 103 | 0.05 g |
| | Allethrin | 0.02 g |
| | Piperonyl butoxide | 0.15 g |
| 7. | Compound No. 107 | 0.05 g |
| | 5-Phenoxybenzyl chrysanthemate | 0.03 g |
| 8. | Compound No. 125 | 0.05 g |

Formulation of Mat for Heating on Hot Plate

| No. | Composition | |
|---|---|---|
| | Allethrin | 0.01 g |

FORMULATION 12

To 1 part of each of Compound Nos. 22, 51, 62, 63, 83, 86, 94, 103, 108 and 125 of this invention was added 5 parts of piperonyl butoxide and the mixture was dissolved in 20 parts of acetone. After 94 parts of 300-mesh diatomaceous earth was added, the resulting blend was thoroughly stirred and mixed in a triturator, and acetone was removed by evaporation to obtain a powder in each case.

EXAMPLE 1

10 third inster larvae of tabacco cutworm (*Spodoptera lituna* Fabricius) were placed in a glass tray having a high side-wall and a diameter of 14 cm, and a 1 ml of a 200-fold dilute solution of each of the emulsifiable concentrates obtained in Formulations 1 and 3 diluted with water was sprayed on the larvae by a sprayer and the larvae thus treated were then transferred into a glass tray containing feeds followed by allowing to stand. Two days after the treatment, greater than 80% of the larvae was found to be killed in each case.

EXAMPLE 2

In an area of the radish field in 5–6 leaf stage, a number of green peach aphid (*Myzus persicae* Sulza) was atomized with a 200-fold dilute solution of each of the emulsifiable concentrates obtained in Formulations 1, 2 and 4 diluted with water at a level of 424 l/acre. Investigation two days after treatment revealed that the density of aphids is reduced to less than 1/10 the density before treatment in each case.

EXAMPLE 3

A piece of plywood board (15 cm × 15 cm) was applied with a 200-fold dilute solution of each of the emulsifiable concentrates obtained in Formulations 1 and 2 diluted with water in an amount of 50 ml/m$^2$ followed by being dried. The adult german cockroaches (*Blattella germanica* Linne) were then brought into contact with the plywood board thus treated for 1 hour, and it was found that more than 80% cockroaches was killed three days after contacting with the board.

EXAMPLE 4

A field of egg-plant (ripe plant) growing a number of larvae of potato lady beetle (*Epilachna sparsa orientalis* Dieke) was atomized with a 200-fold dilute solution of each of the emulsifiable concentrates obtained in Formulation 1 in an amount of 424 l/acre. Investigation on knock-down thirty minutes after the treatment revealed that 90% larvae fell to the ground. A further investigation on density of larvae 24 hours after the treatment revealed that almost 100% larvae had been controlled as compared with the density of larvae before the treatment.

EXAMPLE 5

Fourty-five day-old rice plants after seeding were grown in Wagner pots (1/50000) and sprayed with a 400-fold dilute solution of each of the wettable powders obtained in Formulation 8 in an amount of 10 ml/pot. The pots were then covered with a cylindrical metal net and about 20 larvae of leaf hopper (*Cicadula sexnotata*) were released therein. In each case, more than 80% larvae were found to be killed one day after the release.

EXAMPLE 6

Each of the dusts obtained in Formulation 12 was placed uniformly at the bottom of glass trays having a diameter of 14 cm and a high side-wall in an amount of 2 g/m$^2$ and butter was applied to the glass wall except for about 1 cm portion of the bottom. 10 adult german cockroaches per group were then released in the glass trays and, after contacting 30 minutes, the larvae were transferred to a fresh glass container. In each case, more than 80% of the larvae was found to be killed three days after the treatment.

EXAMPLE 7

Each of the oil preparations obtained in Formulation 5 was atomized using Campel's turn table apparatus [Soap and Sanitary Chemicals, Vol. 14, No. 6, 119 (1938)] in an amount of 5 ml. 20 seconds after atomizing, the shutter was opened and 100 adult oriental house flies (*Musca domestica vicina* Maquant) per group were exposed to the falling atomized fumes for a period of 10 minutes. The flies thus treated were then fed and followed by allowing to stand. More than 80% of the flies were found to be killed in each case.

EXAMPLE 8

Each of the oil preparations obtained in Formulation 7 was sprayed in a (70 cm)$^3$ volume glass box containing about 50 adult oriental house flies in an amount of 0.7 ml under a pressure of 1.5 Kg/cm$^2$ and it was found that more than 80% of the flies was knocked down in 10 minutes after the treatment in each case.

EXAMPLE 9

About 50 adult mosquitoes (*Culex pipiens*) per group were released in a (70 cm)$^3$ volume glass box and sprayed with each of the oil preparations obtained in Formulation 6 in an amount of 0.7 ml under a pressure of 1.5 Kg/cm$^2$. It was found that more than 80% of the flies was knocked down in 10 minutes after the treatment in each case.

EXAMPLE 10

A nylon net of about 15 mesh was sprayed on the lower part of a glass cylinder having a diameter of 20 cm and a height of 20 cm and butter was applied on the upper part of the glass cylinder in a width of about 3 cm. Then 20 adult german cockroaches were released therein. The glass cylinder containing the cockroaches was plied on another glass cylinder of the same size, and further another glass cylinder having a diameter of 20 cm and a height of 40 cm was placed thereon. 0.5 ml of each of the oil preparations obtained in Formulation 7 was sprayed from the upper cylinder using a glass atomizer under a pressure of 0.75 Kg/cm$^2$ and then sealed followed by allowing to stand. It was found that more than 90% of the cockroaches were knocked down in 30 minutes after the treatment and that more than 90% of the cockroaches were killed 3 days after the treatment.

EXAMPLE 11

Insecticidal activity of each of the aerosols obtained in Formulation 10 on oriental house flies was treated by an aerosol test method using a Peet grady chamber [a method reported in Soap and Chemical Specialities Bluebook (1965)]. The test results revealed that knock-down of more than 80% of the flies was observed in 15 minutes after the treatment and more than 70% of the flies was killed one day after the treatment in each case.

EXAMPLE 12

About 50 adult mosquitoes (*Culex pipiens*) were released in a (70 cm)$^3$ volume glass box and a mosquito coil both ends thereof having been ignited, was placed in the center of the box bottom. After 20 minutes more than 80% of the flies were found to be knocked down.

EXAMPLE 13

About 50 adult mosquitoes (*Culex pipiens*) were released in a (70 cm)$^3$ volume glass box and a heating mat obtained in Formulation 11 fixed on an electrothermic plate was placed in the glass box followed by heating to smoke. Within 20 minutes, more than 90% of the mosquitoes was found to be knocked down.

While the invention has been described in detail and with reference to specific embodiments thereof, it will be apparent to one skilled in the art that various changes and modifications can be made therein without departing from the spirit and scope thereof.

What is claimed is:

1. A compound of the formula

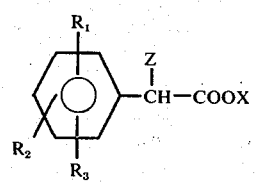

wherein R$_1$ is a member selected from the group consisting of hydrogen, methoxy, methylsulfinyl, allyl, methylthio, trifluoromethyl, nitro, methoxycarbonyl, ethoxy, methyl, chlorine, propyl, butyl, bromine, fluorine, iodine, ethyl, ethoxycarbonyl or methoxymethyl; R$_2$ is a member selected from the group consisting of hydrogen, methyl, methoxy, chlorine or bromine, or R$_1$ and R$_2$ are attached to adjacent carbon atoms and are bonded to one another to form methylenedioxy or tetramethylene; R$_3$ is hydrogen or methyl; Z is a member selected from the group consisting of methyl, ethyl, propyl, butyl, isopropenyl, cyclopropylmethyl, bromoethyl, cyclohexyl, propargyl or trifluoromethyl and X is a member selected from the group consisting of:

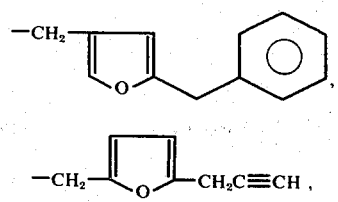

-continued

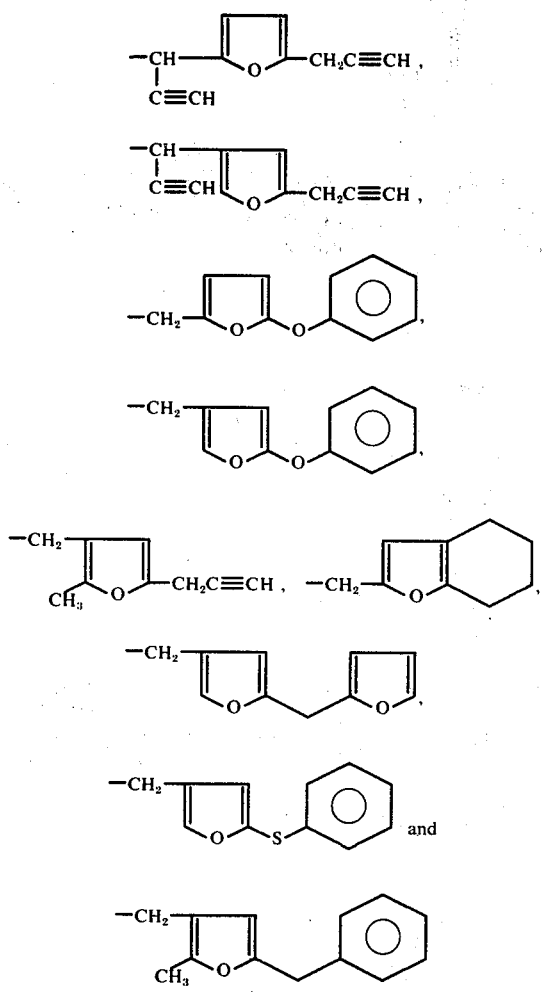

2. A phenylacetate compound of the formula wherein R'₁ represents a straight or branched chain alkyl having 1 to 4 carbon atoms, halogen or alkoxy having 1 to 4 carbon atoms; R'₂ represents hydrogen or forms together with R'₁ when said R'₂ and R'₁ are attached to adjacent carbon atoms, methylenedioxy; and X' represents 3. A phenylacetate compound of the formula wherein B represents a halogen atom, a lower alkyl group or methoxy.

4. A compound of the formula

5. A compound of the formula

6. A compound of the formula

7. A compound of the formula

8. A compound of the formula;

wherein $R_3$ is a member selected from the group consisting of hydrogen, methyl, allyl, methoxycarbonyl and acetyl; $R_4$ is hydrogen; Z is a member selected from the group consisting of ethyl, propyl and allyl; and X is a member selected from the group consisting of

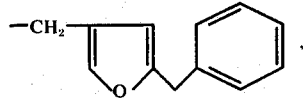, and

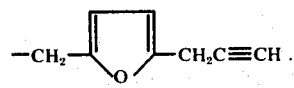.

9. A compound of the formula;

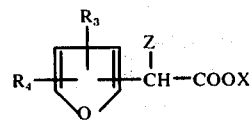

wherein $R_3$ is a member selected from the group consisting of hydrogen, methyl, allyl, methoxycarbonyl and butanoyl; $R_4$ is hydrogen; Z is ethyl or propyl; X is a member selected from the group consiting of

, and

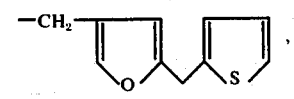,

10. A compound of the formula;

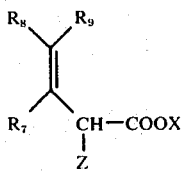

wherein $R_7$ is a member selected from the group consisting of hydrogen, methyl and ethyl; $R_8$ is hydrogen or methyl; $R_9$ is methyl; Z is $C_1$–$C_3$ alkyl; and X is a member selected from the group consisting of —CH$_2$—[furan]—CH$_2$C≡CH    and —CH$_2$—[furan]—[phenyl], 11. A compound of the formula;

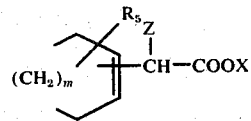

wherein $R_5$ is hydrogen or methyl; $m$ is an integer of 1 or 2; Z is a member selected from the group consisting of methyl, propyl, allyl and propargyl; X is a member selected from the group consisting of —CH$_2$—[furan]—[phenyl]    and —CH$_2$—[furan with CH$_3$]—CH$_2$C≡CH.

* * * * *

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

Column 1, delete formulae (II) through (V) and insert the following therefor:

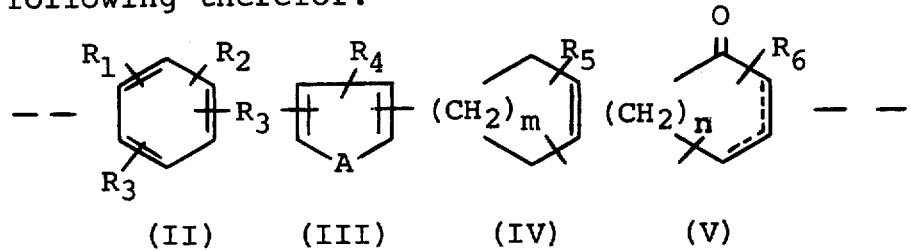

(II)　　(III)　　(IV)　　(V)

UNITED STATES PATENT AND TRADEMARK OFFICE
CERTIFICATE OF CORRECTION

PATENT NO.   : 3,996,244
DATED        : December 7, 1976
INVENTOR(S)  : Keimei FUJIMOTO et al It is certified that error appears in the above-identified patent and that said Letters Patent are hereby corrected as shown below:

(continued)

Column 7, between lines 11 and 15, delete the formula after "and" and insert the following:

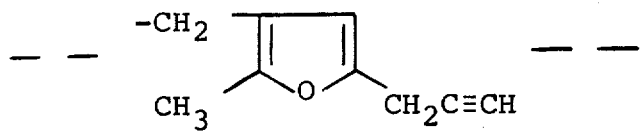

Column 7, beneath "6. compounds of the formula:" delete the formula and insert the following therefor:

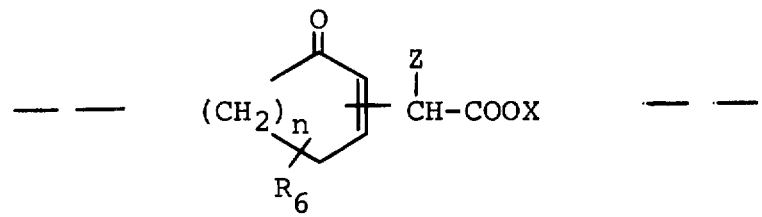

Column 7, lines 43-49, delete the formula and insert the following therefor:

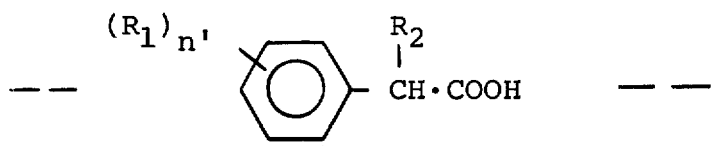

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

(continued)

Column 12, compound No. 3, change to read:

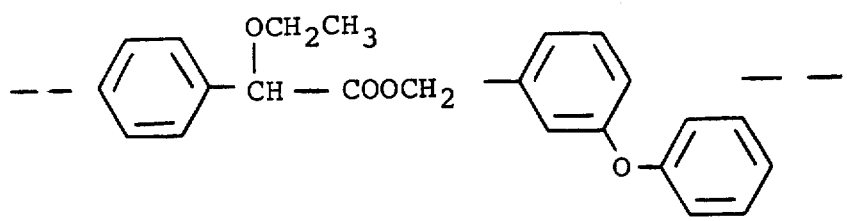

Column 12, compound No. 6, change to read:

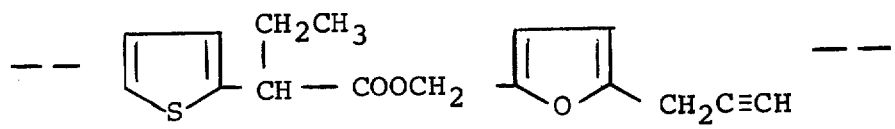

Column 13, compound No. 10, change to read:

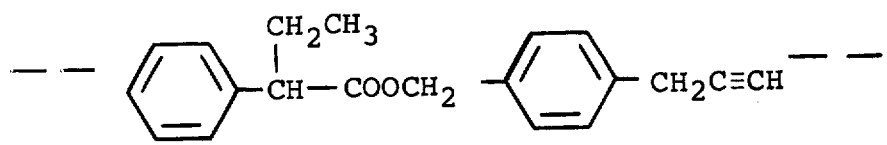

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

(continued)

Column 15, compound No. 20, change to read:

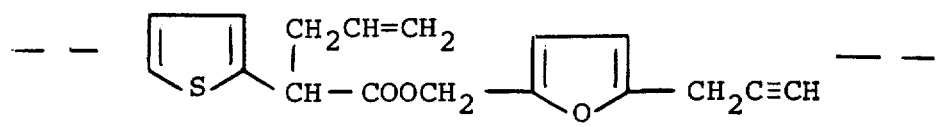

Column 17, compound No. 27, change to read:

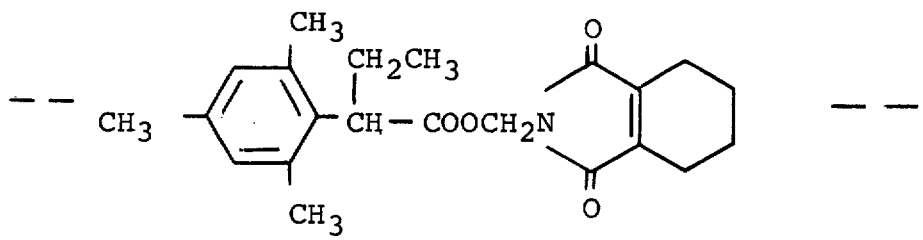

Column 23, compound No. 52, change to read:

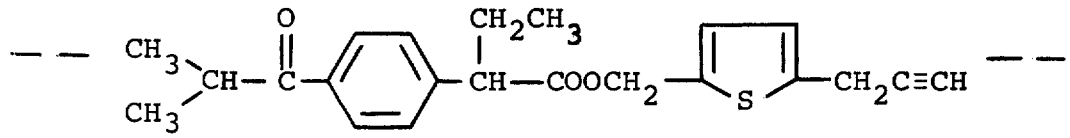

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

(continued)

Column 27, compound No. 64, change to read:

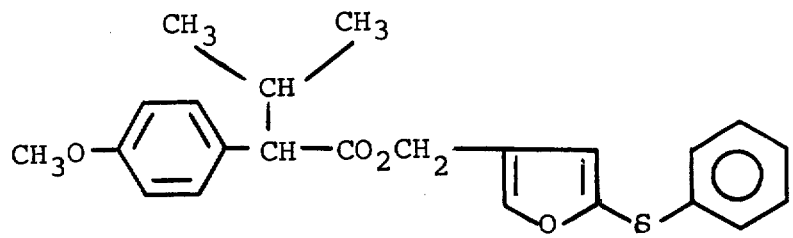

Column 27, compound No. 66, change to read:

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

(continued)

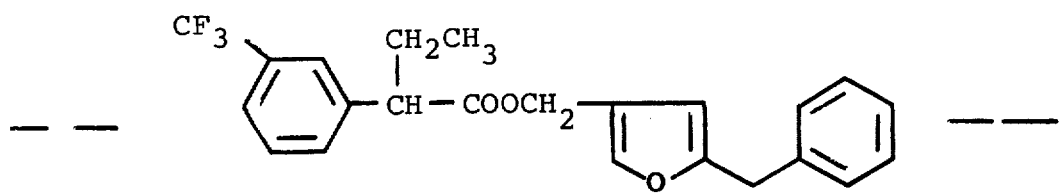

Column 35, compound No. 101, change to read:

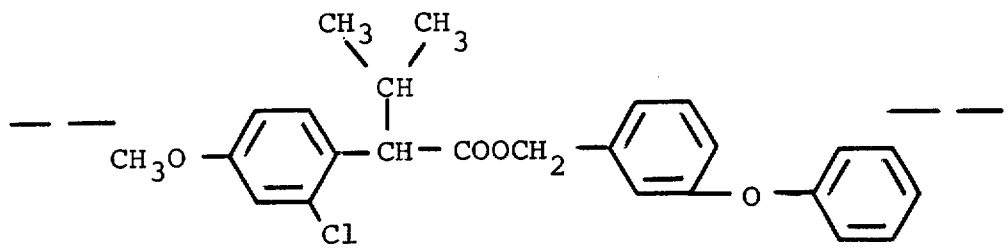

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

(continued)

Column 47, under the column designated "Z" change "$CH_2=CH-CH_2=$" to -- $CH_2=CH-CH_2-$ --

Column 48, the 6th compound under column designated "O-X" change to read:

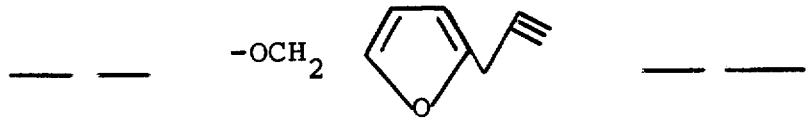

Column 50, the compound opposite compound 8, change to read:

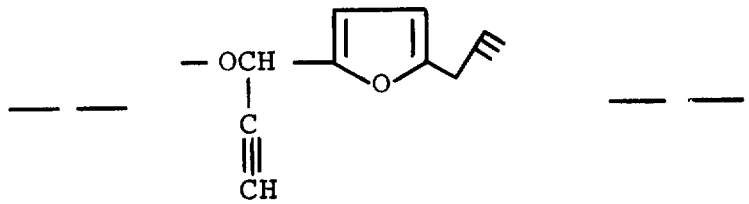

Column 50, the compound opposite compound 10, change to read:

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

(continued)

Column 50, the compound opposite compound 19, change to read:

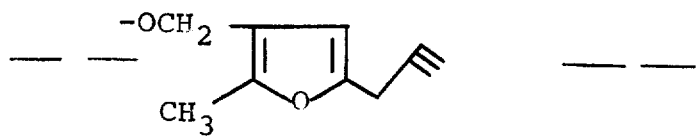

Column 52, the compound opposite compound 20, change to read:

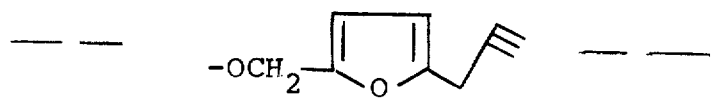

Column 52, the compound opposite compound 28, change to read:

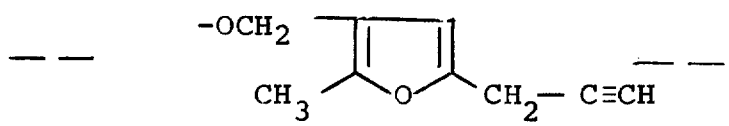

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

(continued)

Column 53, the compound listed at the right of compound 45, change to read:

Column 54, the compound opposite compound 51 change to read:

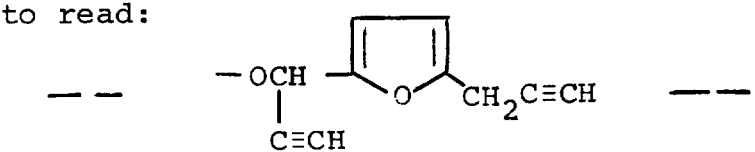

Column 54, the compound opposite compound 52 change to read:

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

(continued)

Column 56, the compound opposite compound 67, change to read:

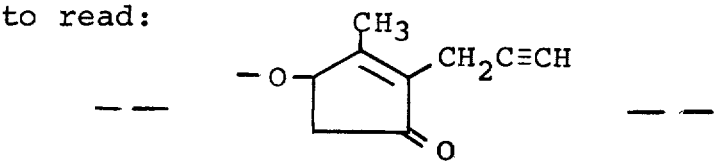

Column 56, the compound opposite compound 69, change to read:

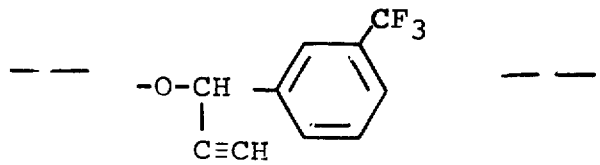

Column 58, the compound opposite compound 129, change to read:

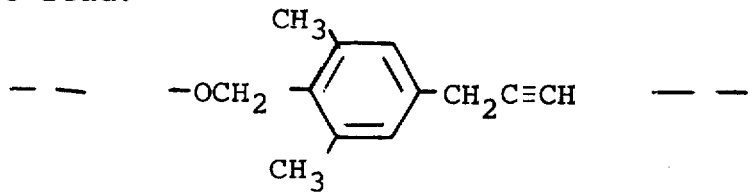

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

(continued)

Column 60, the compound opposite compound 132, change to read:

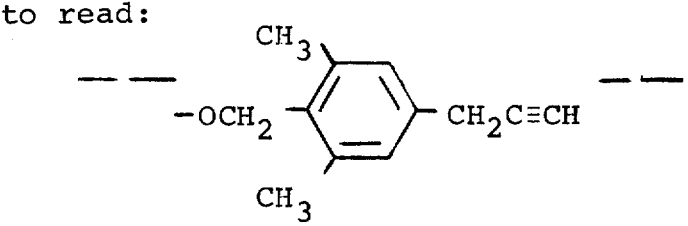

Column 60, the compound opposite compound 141, change to read:

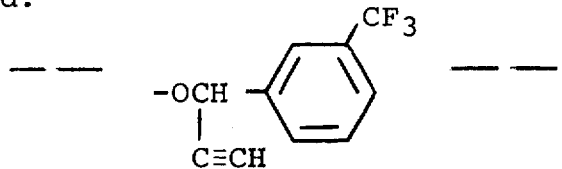

Column 62, the compound opposite compound 146, change to read:

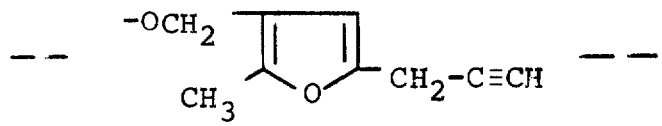

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

(continued)

Column 62, the compound opposite compound 147, change to read:

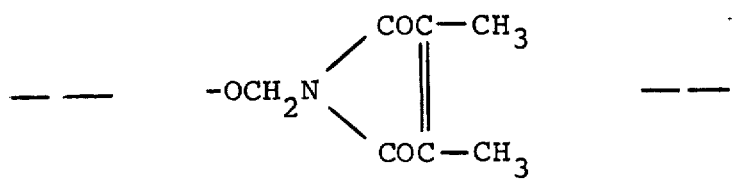

Column 62, the compound opposite compound 151, change to read:

Column 82, the compound opposite compound 266, change to read:

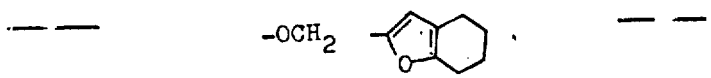

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above—identified patent and that said Letters Patent are hereby corrected as shown below:

(continued)

Column 86, the compound opposite compound 281, change to read:

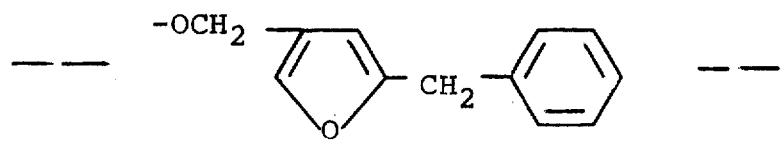

Column 86, the compound opposite compound 286, change to read:

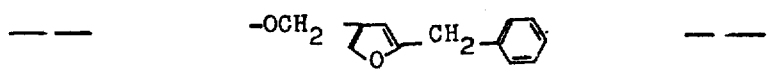

IN THE CLAIMS:

Claim 2, change the formula appearing at line 60 to the following:

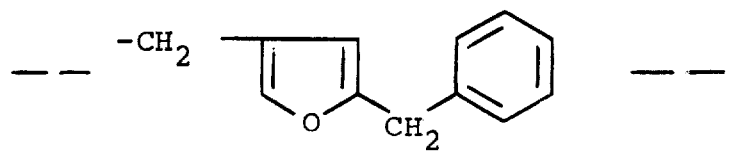

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above—identified patent and that said Letters Patent are hereby corrected as shown below:

(continued)

Claim 7, change the formula therein to the following:'

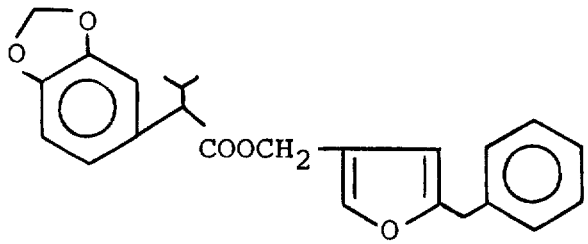

Signed and Sealed this

Fourteenth Day of March 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO ET AL It is certified that error appears in the above—identified patent and that said Letters Patent are hereby corrected as shown below:

IN THE SPECIFICATION:

Column 4, in the compounds listed on the left thereof, change

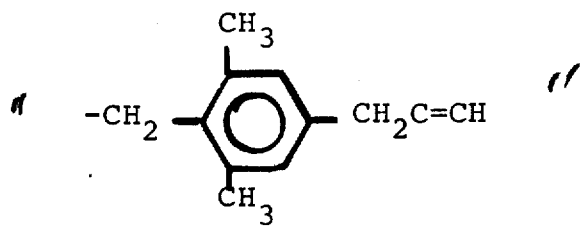

to the following

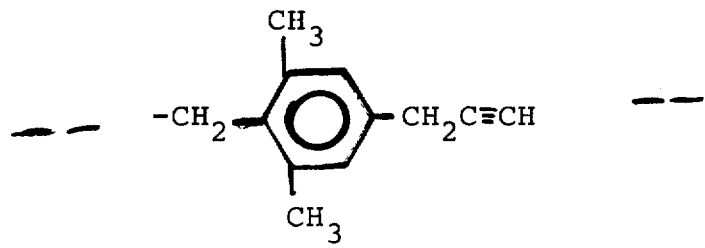

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO ET AL It is certified that error appears in the above-identified patent and that said Letters Patent are hereby corrected as shown below:

continued

Column 23, compound No. 53, change to read:

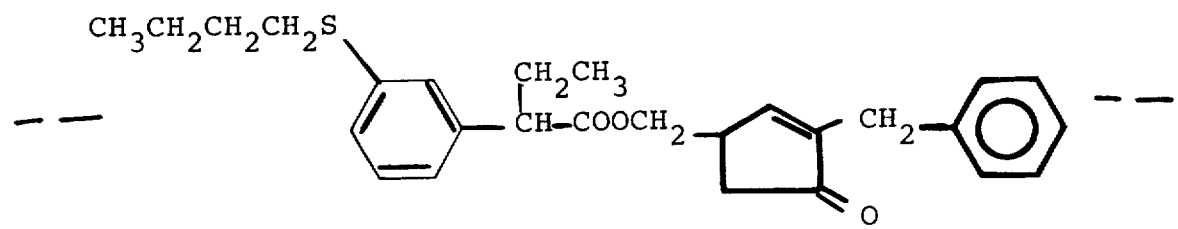

Column 35, compound No. 103, change to read:

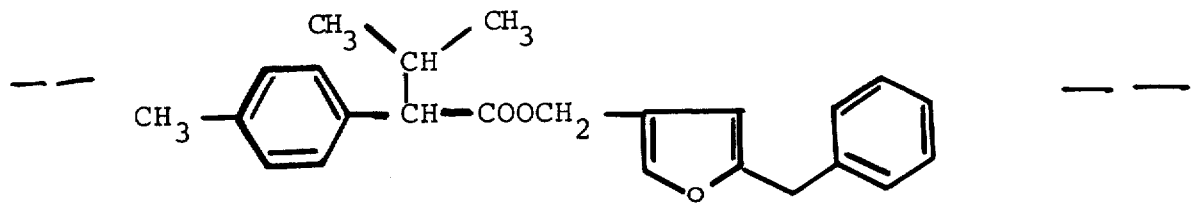

UNITED STATES PATENT AND TRADEMARK OFFICE
CERTIFICATE OF CORRECTION

PATENT NO. : 3,996,244
DATED : December 7, 1976
INVENTOR(S) : Keimei FUJIMOTO et al It is certified that error appears in the above-identified patent and that said Letters Patent are hereby corrected as shown below:

continued

Column 54, the compound opposite compound 37 change to read:

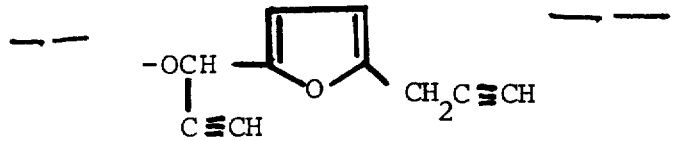

Signed and Sealed this

Twenty-second Day of August 1978

[SEAL]

Attest:

RUTH C. MASON
Attesting Officer

DONALD W. BANNER
Commissioner of Patents and Trademarks